US009517001B2

(12) United States Patent
Chiba et al.

(10) Patent No.: US 9,517,001 B2
(45) Date of Patent: Dec. 13, 2016

(54) CAPSULE ENDOSCOPE SYSTEM

(71) Applicant: OLYMPUS CORPORATION, Tokyo (JP)

(72) Inventors: Atsushi Chiba, Hachioji (JP); Hironobu Takizawa, Hino (JP); Ryoji Sato, Tokyo (JP); Hironao Kawano, Machida (JP); Kazuhiko Takahashi, Hachioji (JP); Takuto Ikai, Higashimurayama (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 15/053,084

(22) Filed: Feb. 25, 2016

(65) Prior Publication Data

US 2016/0166133 A1    Jun. 16, 2016

Related U.S. Application Data

(63) Continuation of application No. PCT/JP2014/072235, filed on Aug. 26, 2014.

(30) Foreign Application Priority Data

Aug. 28, 2013 (JP) .................................. 2013-177229
Aug. 28, 2013 (JP) .................................. 2013-177230

(51) Int. Cl.
*A61B 1/04* (2006.01)
*A61B 1/00* (2006.01)
(Continued)

(52) U.S. Cl.
CPC ........... *A61B 1/041* (2013.01); *A61B 1/00006* (2013.01); *A61B 1/00045* (2013.01);
(Continued)

(58) Field of Classification Search
CPC ............ A61B 1/00006; A61B 1/00045; A61B 1/00158; A61B 1/041; A61B 5/073; A61B 5/1116; A61B 5/1121; A61B 34/20; A61B 34/10; A61B 17/00234; A61B 34/25; A61B 2034/107; A61B 2018/00982; A61B 6/5247; A61B 8/5223; A61B 1/04; A61B 90/10; A61B 2576/00; A61B 8/5261; A61B 5/062; A61B 6/5229; A61B 5/004; A61B 5/742; A61B 2034/101
See application file for complete search history.

(56) References Cited

U.S. PATENT DOCUMENTS 7,343,036 B2   3/2008 Kleen et al.
7,922,652 B2   4/2011 Yagi et al.
(Continued)

FOREIGN PATENT DOCUMENTS

JP   S60-217326 A   10/1985
JP   H11-104072 A    4/1999
(Continued)

OTHER PUBLICATIONS

International Search Report dated Dec. 9, 2014 issued in PCT/JP2014/072235.
(Continued)

*Primary Examiner* — John P Leubecker
*Assistant Examiner* — Arnaldo Torres Diaz
(74) *Attorney, Agent, or Firm* — Scully, Scott, Murphy & Presser, P.C.

(57) ABSTRACT

A capsule endoscope system includes: a capsule endoscope configured to be introduced into a subject; a guiding unit that generates a magnetic field to guide the capsule endoscope; a guidance magnetic field control unit that switches between ON and OFF of the magnetic field; a body posture discrimi-
(Continued)

nating unit that discriminates a body posture of the subject; a model extracting unit that extracts a body posture model according to the body posture of the subject, from among prepared body posture models, and extracts an organ model according to the body posture of the subject, from among prepared organ models; and a display control unit configured to: superimpose the organ model according to the body posture of the subject, on the extracted body posture model when the magnetic field is ON; and display the extracted body posture model and to hide the organ model when the magnetic field is OFF.

11 Claims, 41 Drawing Sheets

(51) Int. Cl.
*A61B 5/07* (2006.01)
*A61B 5/11* (2006.01)
(52) U.S. Cl.
CPC .......... *A61B 1/00158* (2013.01); *A61B 5/073* (2013.01); *A61B 5/1116* (2013.01); *A61B 5/1121* (2013.01)

(56) References Cited

U.S. PATENT DOCUMENTS

| | | | |
|---|---|---|---|
| 8,214,017 | B2 | 7/2012 | Sato et al. |
| 8,439,822 | B2 | 5/2013 | Shigemori et al. |
| 2009/0227864 | A1* | 9/2009 | Sato ............... A61B 1/0005 600/424 |
| 2009/0299142 | A1 | 12/2009 | Uchiyama et al. |
| 2010/0010304 | A1* | 1/2010 | Kawano ........... A61B 1/00039 600/117 |
| 2010/0010305 | A1* | 1/2010 | Kawano ............ A61B 1/0005 600/118 |
| 2010/0010306 | A1* | 1/2010 | Kawano ........... A61B 1/00039 600/118 |
| 2011/0245731 | A1 | 10/2011 | Chiba et al. |
| 2012/0203068 | A1 | 8/2012 | Sato et al. |
| 2013/0006054 | A1* | 1/2013 | Kawano ............ A61B 1/0005 600/118 |
| 2013/0038711 | A1* | 2/2013 | Sato ............... A61B 1/00048 348/68 |
| 2013/0257865 | A1 | 10/2013 | Kobayashi |
| 2013/0303847 | A1* | 11/2013 | Sitti ............... A61B 1/00158 600/104 |
| 2014/0155709 | A1* | 6/2014 | Ikai ............... A61B 1/00006 600/302 |
| 2015/0138329 | A1* | 5/2015 | Braun .............. A61B 5/6861 348/71 |

FOREIGN PATENT DOCUMENTS

| | | |
|---|---|---|
| JP | 2003-225195 A | 8/2003 |
| JP | 2004-321796 A | 11/2004 |
| JP | 2007-319327 A | 12/2007 |
| JP | 2009-213613 A | 9/2009 |
| JP | 2010-017555 A | 1/2010 |
| JP | 2010-240000 A | 10/2010 |
| JP | 2013-027697 A | 2/2013 |
| JP | 2013-085593 A | 5/2013 |
| JP | 2013-128847 A | 7/2013 |
| WO | WO 2005/077253 A1 | 8/2005 |
| WO | WO 2008/062594 A1 | 5/2008 |
| WO | WO 2008/099851 A1 | 8/2008 |
| WO | WO 2011/055579 A1 | 5/2011 |
| WO | WO 2011/061968 A1 | 5/2011 |

OTHER PUBLICATIONS

Japanese Office Action dated Oct. 27, 2015 issued in JP 2015-511846.
Japanese Office Action dated Jun. 16, 2015 issued in JP 2015-511846.

* cited by examiner

ST1

ST2

ST3

ST4

IMAGING DIRECTION

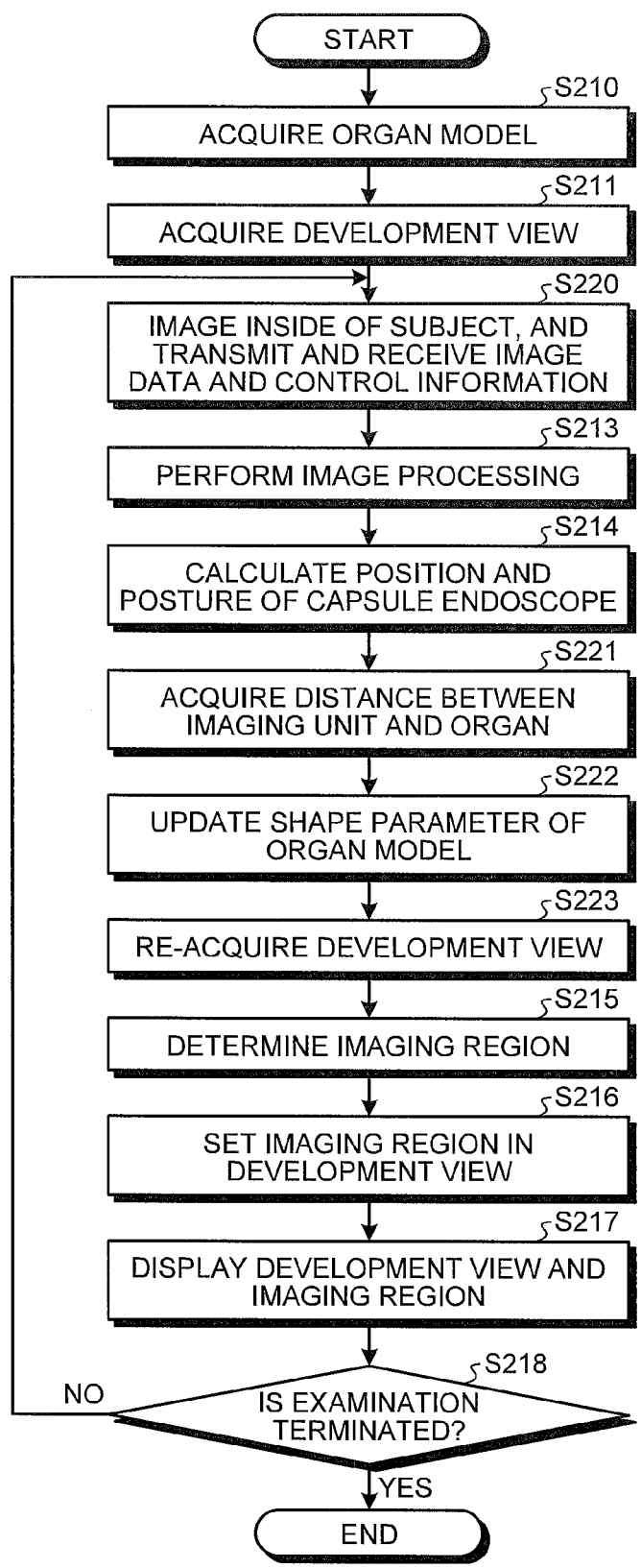

CAPSULE ENDOSCOPE SYSTEM

CROSS-REFERENCE TO RELATED APPLICATIONS

This application is a continuation of PCT international application Ser. No. PCT/JP2014/072235 filed on Aug. 26, 2014 which designates the United States, incorporated herein by reference, and which claims the benefit of priority from Japanese Patent Application No. 2013-177229 and Japanese Patent Application No. 2013-177230, filed on Aug. 28, 2013, incorporated herein by reference.

BACKGROUND

1. Technical Field

The disclosure relates to a capsule endoscope system that causes a capsule endoscope to be introduced into a subject and observes an inside of the subject.

2. Related Art

In the field of endoscopes, capsule endoscopes which can be introduced into a digestive tract of a subject such as a patient have been developed (for example, see Japanese Patent Application Laid-open No. 2009-213613, International Publication Pamphlet No. WO 2008/062594, and International Publication Pamphlet No. WO 2011/061968). The capsule endoscopes are devices having an imaging function and a wireless communication function inside a capsule-shaped casing. The capsule endoscopes sequentially image an inside of an organ of the subject to acquire image signals while moving inside the digestive tract by peristaltic movement after swallowed through a mouse of the subject, and wirelessly transmit the image signals to a receiving device outside the subject. The image signals received in the receiving device is taken into an image display device, and predetermined image processing is applied. Accordingly, an image inside the organ (may also referred to as in-vivo image) is displayed as a still image or a moving image. A user such as a doctor observes the in-vivo image displayed on an image display device as described above, and diagnoses a state of the organ of the subject.

In recent years, systems having a function to guide a capsule endoscope introduced into a subject by magnetic force (hereinafter, referred to as magnetic guidance) has been proposed. For example, Japanese Patent Application Laid-open No. 2009-213613 discloses a capsule guidance system in which a permanent magnet (hereinafter, may also referred to as in-vivo permanent magnet) is provided inside the capsule endoscope, and a magnetic guidance device including a magnetic field generating unit is installed outside the subject, and which guides the capsule endoscope into a position desired by the user by causing a magnetic field formed by the magnetic field generating unit to act on the in-vivo permanent magnet. In such a system, the user can magnetically guide the capsule endoscope into a desired position and direction by operating an operating unit provided in the magnetic guidance device to change the magnetic field while referring to an in-vivo image displayed on the image display device.

Further, a capsule endoscope that has a liquid such as water introduced into a stomach of the subject, and images an inside of the stomach in a state where the capsule endoscope floats in the liquid is also known. For example, International Publication Pamphlet No. WO 2008/062594 discloses a capsule endoscope configured to stand in a state of floating in a liquid (an imaging direction becomes a vertical direction), and which can image upper and lower portions of a liquid surface.

Further, when operating an endoscope introduced into a subject, it is important to grasp which body part in the subject from which direction the capsule endoscope is currently observing. As a technology for grasping body parts for observation, for example, Japanese Patent Application Laid-open No. 60-217326 discloses a technology for displaying an endoscope graphic and an observation position mark together with a side surface image and a developed image of a stomach. Japanese Patent Application Laid-open No. 2003-225195 discloses a technology for displaying a shape of an organ, which is an object into which an inserting unit of a flexible endoscope is inserted, together with a bent state of the inserting unit. Japanese Patent Application Laid-open No. 2007-319327 discloses a technology for recording a gaze of the user (observer) and an operation record of a GUI in time series, and identifying an observed region by the user from the records, in observation work. Japanese Patent Application Laid-open No. 2004-321796 discloses a technology for recording an in-vivo image, and a position and a direction of the capsule endoscope at the time of imaging the in-vivo image, and displaying a pseudo three-dimensional display of a surrounding region of the capsule endoscope based on the aforementioned records.

SUMMARY

In some embodiments, a capsule endoscope system includes: a capsule endoscope configured to be introduced into an inside of a subject and to image the inside of the subject; a guiding unit configured to generate a magnetic field to guide the capsule endoscope; a guidance magnetic field control unit configured to switch between ON and OFF of the magnetic field generated by the guiding unit; a body posture discriminating unit configured to discriminate a body posture of the subject; a model extracting unit configured to extract a body posture model according to the body posture of the subject discriminated by the body posture discriminating unit, from among prepared body posture models, and to extract an organ model according to the body posture of the subject discriminated by the body posture discriminating unit, from among prepared organ models correlated with the body posture of the subject; and a display control unit configured to: distinguish between ON and OFF of the magnetic field generated by the guiding unit, based on switching by the guidance magnetic field control unit; superimpose the organ model according to the body posture of the subject extracted by the model extracting unit, on the body posture model extracted by the model extracting unit to produce a superimposed image, and to display the superimposed image when the magnetic field generated by the guiding unit is distinguished to be ON; and display the body posture model extracted by the model extracting unit and to hide the organ model when the magnetic field generated by the guiding unit is distinguished to be OFF.

The above and other features, advantages and technical and industrial significance of this invention will be better understood by reading the following detailed description of presently preferred embodiments of the invention, when considered in connection with the accompanying drawings.

BRIEF DESCRIPTION OF THE DRAWINGS

FIG. 40 is a flowchart illustrating a movement of the capsule endoscope system according to the sixth embodiment of the present invention;

DETAILED DESCRIPTION

Figure 1:
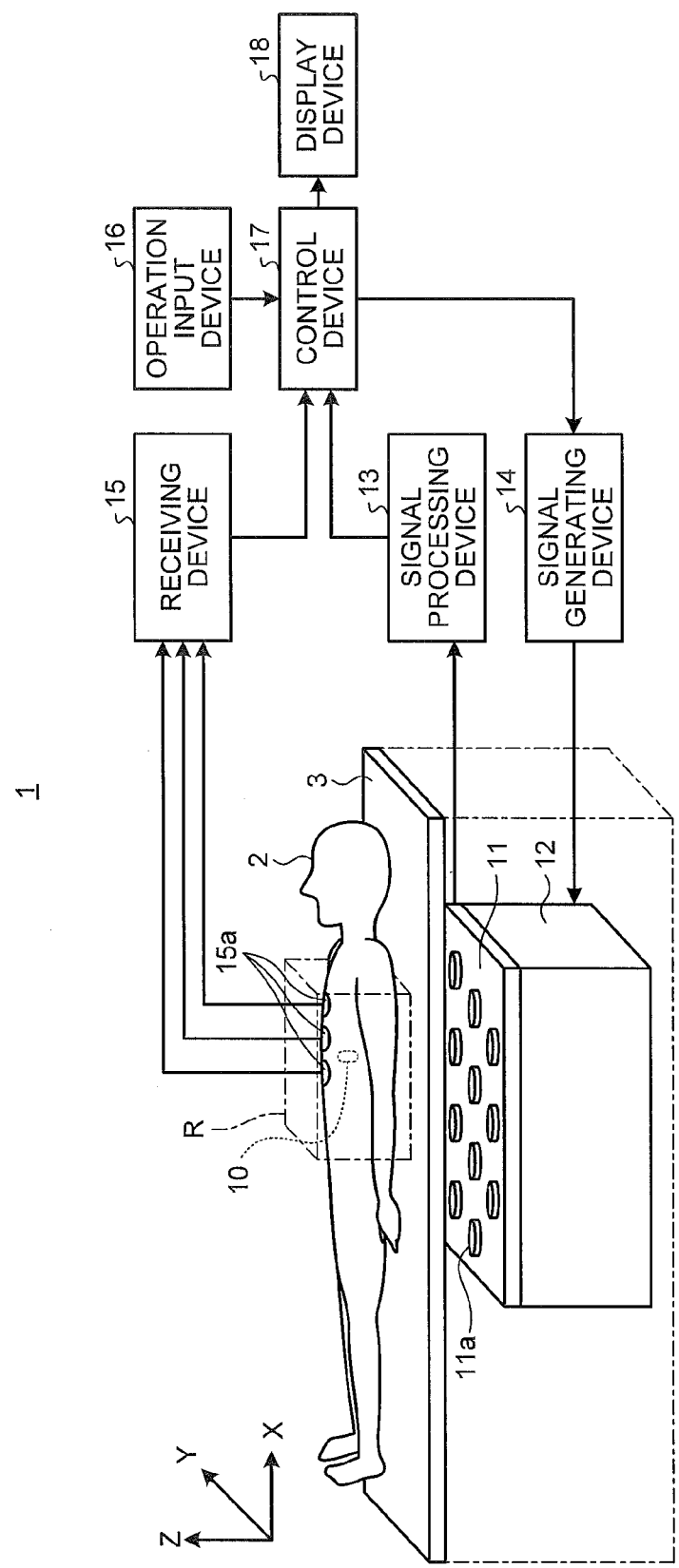
FIG. 1 is a diagram illustrating a configuration example of a capsule endoscope system according to a first embodiment of the present invention.

Hereinafter, a capsule endoscope system according to some embodiments of the present invention will be described with reference to the drawings. Note that, in the description below, an example of a capsule endoscope orally introduced into a subject, and which performs imaging while floating in a liquid stored in a stomach of the subject will be described. However, the present invention is not limited by the embodiments. That is, the present invention can be used in various capsule endoscopes such as a capsule endoscope that images an inside of a digestive tract while moving from an esophagus to an anus of the subject by peristaltic movement, and a capsule endoscope inserted through the anus together with an isotonic solution. Further, in the description below, the drawings merely schematically illustrate shapes, sizes, and positional relationships to the extent that details of the present invention can be understood. Therefore, the present invention is not limited only to the shapes, the sizes, and the positional relationships exemplarily illustrated in the drawings. The same reference signs are used to designate the same elements throughout the drawings.

First Embodiment

FIG. 1 is a diagram illustrating a configuration example of a capsule endoscope system according to a first embodiment of the present invention. As illustrated in FIG. 1, a capsule endoscope system 1 according to the first embodiment includes a capsule endoscope 10 introduced into a digestive tract of a subject 2, and wirelessly transmits an image signal acquired by imaging an inside of the subject 2, a position detection device 11 and a magnetic field generating device 12 provided below a bed 3 where the subject 2 is placed, a signal processing device 13 that processes the signal output from the position detection device 11, a signal generating device 14 that generates a signal for moving the magnetic field generating device 12, a receiving device 15 that receives the image signal wirelessly transmitted from the capsule endoscope 10, an operation input device 16 for guiding and operating the capsule endoscope 10, a control device 17 that performs processing for displaying an image in the subject 2 (hereinafter, referred to as in-vivo image) based on the image signal received by the receiving device 15, and a display device 18 that displays the in-vivo image and other information.

The bed 3 is placed such that an upper surface (a placing surface of the subject 2) becomes parallel to a horizontal plane (a plane perpendicular to a gravity direction). Hereinafter, a longitudinal direction of the bed 3 is an X direction, a short direction of the bed 3 is a Y direction, and a vertical direction (gravity direction) is a Z direction.

Figure 2:
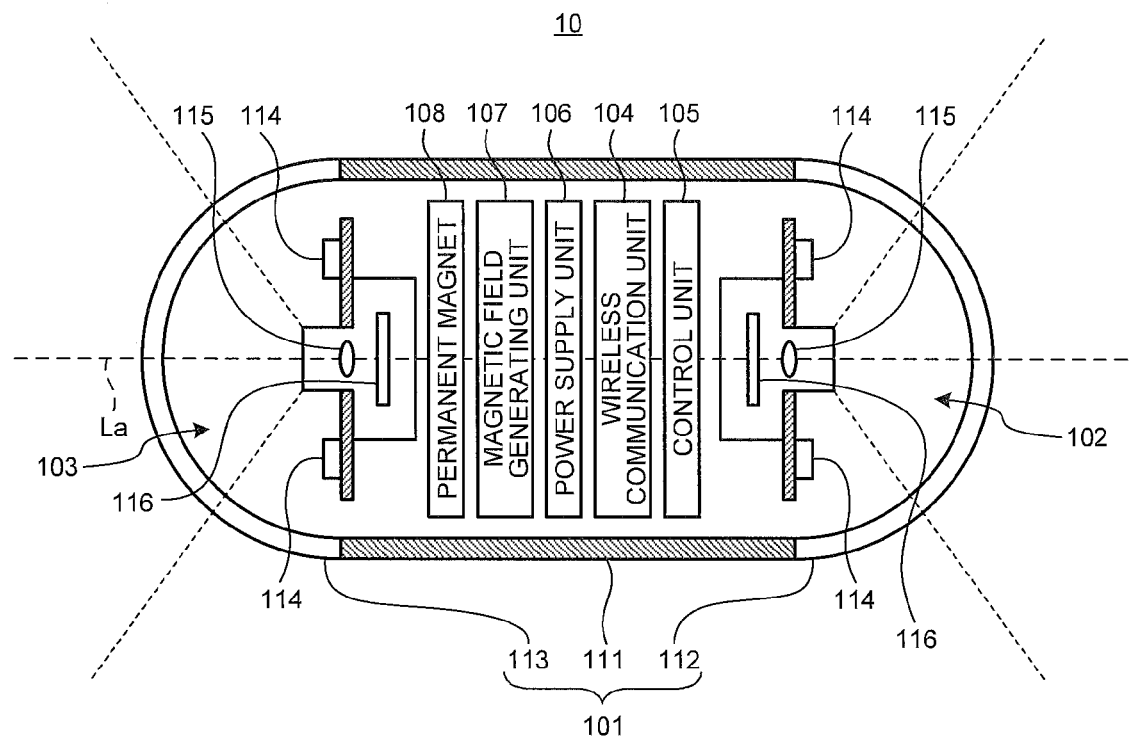
FIG. 2 is a schematic diagram illustrating an example of an internal structure of a capsule endoscope system illustrated in FIG. 1.

FIG. 2 is a schematic diagram illustrating an example of an internal structure of the capsule endoscope 10. As illustrated in FIG. 2, the capsule endoscope 10 includes a capsule-shaped casing 101 as an outer casing configured to be introduced into an organ of the subject 2, imaging units 102 and 103 that image an object and generate an image signal, a wireless communication unit 104 that wirelessly transmits the image signal generated by the imaging units 102 and 103 to an outside, a control unit 105 that controls respective configuration units of the capsule endoscope 10, a power supply unit 106 that supplies power to the respective configuration units of the capsule endoscope 10, a magnetic field generating unit 107 that generates alternating magnetic field for detection of the position of the capsule endoscope 10, and a permanent magnet 108 that enables magnetic guidance by the magnetic field generating device 12.

The capsule-shaped casing 101 is an outer casing configured to be introduced into an organ of the subject 2, and made of a tubular casing 111 and dome-shaped casings 112 and 113, and is realized such that both-side opening ends of the tubular casing 111 are blocked with the dome-shaped casings 112 and 113. The dome-shaped casings 112 and 113 are dome-shaped optical members transparent for light in a predetermined wavelength band such as visible light. Further, the tubular casing 111 is a colored casing approximately opaque for visible light. The capsule-shaped casing 101 formed of these tubular casing 111 and dome-shaped casings 112 and 113 liquid-tightly includes the imaging units 102 and 103, the wireless communication unit 104, the control unit 105, the power supply unit 106, the magnetic field generating unit 107, and the permanent magnet 108, as illustrated in FIG. 2.

Each of the imaging units 102 and 103 includes an illuminating unit 114 such as an LED, an optical system 115 such as a condenser lens, and an image sensor 116 such as a CMOS image sensor or a CCD. The illuminating unit 114 emits illumination light such as white light to an imaging visual field of the image sensor 116, and illuminates the object in the imaging visual field over the dome-shaped casings 112 and 113. The optical system 115 collects reflected light from the imaging visual field to an imaging surface of the image sensor 116 and focuses an object image. The image sensor 116 receives the reflected light from the imaging visual field collected on the imaging surface, and performs photoelectric conversion of a received photo signal, thereby to generate an image signal that indicates the object image of the imaging visual field, that is, an in-vivo image of the subject 2.

As illustrated in FIG. 2, when the capsule endoscope 10 is a pantoscopic capsule endoscope that images the front and the rear of a long axis La, these imaging units 102 and 103 are arranged such that optical axes thereof are approximately parallel to or approximately accord with the long axis La that is a central axis of the capsule-shaped casing 101 in the longitudinal direction, and imaging visual fields face mutually opposite directions. That is, the imaging units 102 and 103 are mounted such that the imaging surface of the image sensor 116 becomes perpendicular to the long axis La.

The wireless communication unit 104 wirelessly and sequentially transmits the image signals generated by the imaging units 102 and 103 through an antenna (not illustrated) to an outside. To be specific, the wireless communication unit 104 acquires the image signal generated by the imaging units 102 and 103 from the control unit 105, and applies signal processing such as modulation to the image signal to generate a wireless signal. The wireless communication unit 104 transmits the wireless signal to the receiving device 15 provided outside the subject 2.

The control unit 105 controls operations of the imaging units 102 and 103 and the wireless communication unit 104, and controls input/output of signals among these configuration units. To be specific, the control unit 105 acquires the image signal and applies predetermined signal processing to the image signal every time the image sensor 116 generates the image signal, and further controls the wireless communication unit 104 to wirelessly and sequentially transmit the image signal to an outside in a time series.

The power supply unit 106 is a storage unit such as a button-type battery or a capacitor, and includes a switch unit such as a magnetic switch or an optical switch. The power supply unit 106 switches ON/OFF states of the power supply with the magnetic field applied from an outside, and appropriately supplies the power in the storage unit to the respective configuration units (the imaging units 102 and 103, the wireless communication unit 104, the control unit 105, and the magnetic field generating unit 107) of the capsule endoscope 10 in the ON state. Further, the power supply unit 106 stops the power supply to the respective configuration units of the capsule endoscope 10 in the OFF state.

The magnetic field generating unit 107 forms a part of a resonance circuit, includes a transmitting coil that generates the magnetic field when a current flows, and a capacitor that forms the resonance circuit together with the transmitting coil, and generates an alternating magnetic field having a predetermined frequency on receipt of the power supply from the power supply unit 106.

The permanent magnet 108 is fixed to and arranged in the capsule-shaped casing 101 such that a magnetizing direction has an inclination with respect to the long axis La. In the first embodiment, the permanent magnet 108 is arranged such that the magnetizing direction becomes perpendicular to the long axis La. The permanent magnet 108 is moved following the magnetic field applied from an outside, and as a result, magnetic guidance of the capsule endoscope 10 by the magnetic field generating device 12 described below is realized.

Figure 3:
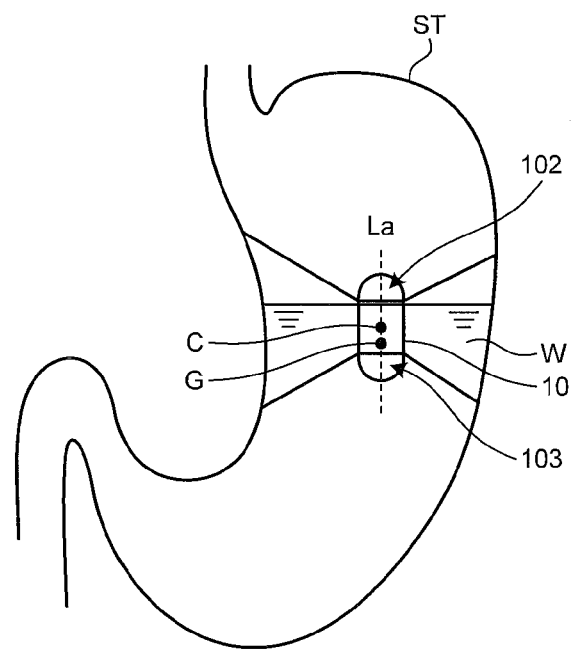
FIG. 3 is a schematic diagram illustrating a state in which a liquid and the capsule endoscope are introduced into an organ of a subject.

FIG. 3 is a schematic diagram illustrating a state in which a liquid W and the capsule endoscope 10 are introduced in an organ (stomach ST) of the subject 2. Note that FIG. 3 illustrates a state in which the magnetic field for controlling a position and a posture of the capsule endoscope 10 is not applied to the permanent magnet 108 in the capsule endoscope 10.

The capsule endoscope 10 exemplarily illustrated in the first embodiment is designed to flow in the liquid W. Further, the center of gravity G of the capsule endoscope 10 is set to come to a position shifted from a geometric center C of the capsule endoscope 10 along the long axis La of the capsule endoscope 10. The center of gravity G is set to a position on the long axis La, and a position deviating from the geometric center C of the capsule-shaped casing 101 toward a side of the imaging unit 103, by adjustment of arrangement of the respective configuration units such as the power supply unit 106 and the permanent magnet 108. Accordingly, the capsule endoscope 10 floats in the liquid W in a state where the own long axis La becomes approximately parallel to the vertical direction (that is, the gravity direction). In other words, the capsule endoscope 10 floats in the liquid W in a state where a straight line connecting the geometric center C and the center of gravity G stands upright. The capsule endoscope 10 causes the imaging visual field of one imaging unit 102 to face vertically upward, and the imaging visual field of the other imaging unit 103 to face vertically downward in such a upright posture. Note that the liquid W is a liquid non-toxic to human bodies, such as water or saline.

Note that only one of the imaging units 102 and 103 may be provided in the capsule endoscope 10. In this case, the imaging direction of when the capsule endoscope 10 floats in the liquid W can be set to a vertically upward or downward direction by adjustment of the position of the center of gravity G.

By causing the magnetic field from an outside to act on the permanent magnet 108 of the capsule endoscope 10 floating as described above, the position of the capsule endoscope 10, the inclination with respect to the vertical direction of the long axis La, and rotation (swing) of the long axis La with respect to the vertical axis that passes the center of gravity G can be controlled.

Referring to FIG. 1 again, the position detection device 11 includes a plurality of sensing coils 11a arranged on a panel forming a planar shape, and each of which receives the alternating magnetic field generated from the magnetic field generating unit 107 of the capsule endoscope 10 and outputs a detection signal. Each sensing coil 11a is made of a coil spring-type cylindrical coil. Such a position detection device 11 is arranged near the subject 2 in an examination. In the first embodiment, the position detection device 11 is arranged below the bed 3.

The signal processing device 13 takes in detection signals output from the sensing coils 11a of the position detection device 11, adjusts waveforms of the detection signals by filter processing, then applies amplification and A/D conversion processing, and outputs the processed signals to the control device 17 as position detection signals of the capsule endoscope 10. In the first embodiment, these position detection device 11, signal processing device 13, and position calculation unit 132 describe below constitute a detecting unit that detects the position and the posture of the capsule endoscope 10.

Note that a method of detecting the position applicable to the capsule endoscope system 1 is not limited to the above-described method of detecting the alternating magnetic field, and various known methods are applicable. For example, the capsule endoscope 10 in the subject 2 may be estimated based on reception intensity distribution of the image signals received by a plurality of antennas 15a. In this case, it becomes unnecessary to provide the magnetic field generating unit 107 in the capsule endoscope 10.

The magnetic field generating device 12 generates a magnetic field for controlling at least one of the position and the posture of the capsule endoscope 10 introduced into the subject 2. To be specific, the magnetic field generating device 12 includes a plurality of electromagnets, and traps the permanent magnet 108 of the capsule endoscope 10 with a synthetic magnetic field of the magnetic fields generated from the electromagnets according to the signal generated by the signal generating device 14. At this time, the magnetic fields generated from the electromagnets are adjusted and the synthetic magnetic field is changed, so that the capsule endoscope 10 can be guided to the position and the posture desired by the user.

The signal generating device 14 generates a drive signal for driving the electromagnets included in the magnetic field generating device 12 under control of the control device 17 (a guidance magnetic field control unit 151 describe below). In the first embodiment, these magnetic field generating device 12 and signal generating device 14 constitute a guiding unit that guides the capsule endoscope 10 in the subject 2. Further, hereinafter, a region of the capsule endoscope 10 guidable with the magnetic field generated by the magnetic field generating device 12 is referred to as guidance region R.

Note that the configuration of the guiding unit applicable to the capsule endoscope system 1 is not limited to the configuration made of the above-described magnetic field generating device 12 and signal generating device 14. Various known configurations are applicable. For example, a permanent magnet (hereinafter, in-vitro permanent magnet)

and a driving unit that moves and rotates the in-vitro permanent magnet may be provided in place of the magnetic field generating device 12. In this case, the in-vitro permanent magnet is moved and rotated while the permanent magnet 108 of the capsule endoscope 10 is trapped with the magnetic field generated by the in-vitro permanent magnet, so that the position and the posture of the capsule endoscope 10 can be controlled.

The receiving device 15 includes a plurality of antennas 15a that receives the wireless signal transmitted from the capsule endoscope 10 introduced into the subject 2. These antennas 15a are housed in a pad, and the pad is stuck to a predetermined position of a body surface of the subject 2. Alternatively, a jacket to which the plurality of antennas 15a is attached (antenna jacket) may be worn by the subject 2. The receiving device 15 sequentially takes in the wireless signal from the capsule endoscope 10, the signal having been received by the antennas 15a, and performs predetermined signal processing such as demodulation processing for the signal taken in from the antenna having the highest received field intensity, thereby to obtain a digital image signal (image data) regarding the subject 2, and outputs the digital image signal to the control device 17.

The operation input device 16 is an input device used when the user such as a doctor performs various input operations, and is configured from a console that includes a keyboard, a mouse, a touch panel, a joystick, and various buttons and switches. The operation input device 16 outputs a signal according to an operation made from an outside, such as an input operation by the user, to the control device 17.

Figure 4A:
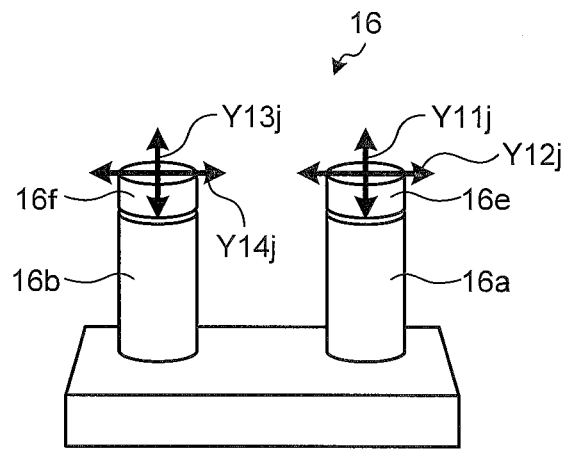
FIGS. 4A and 4B are schematic diagrams illustrating a configuration example of an operation input device illustrated in FIG. 1.
Figure 4B:
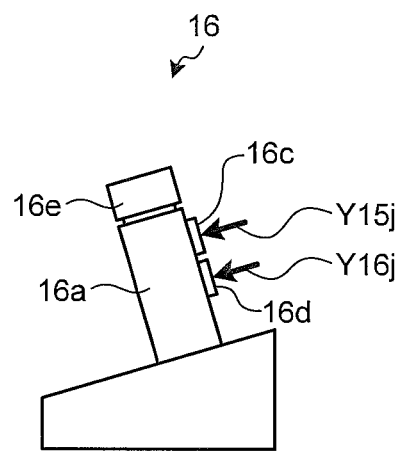

FIGS. 4A and 4B are schematic diagrams illustrating an example in which the operation input device 16 for magnetically guiding the capsule endoscope 10 introduced into the subject 2 is configured from two joysticks 16a and 16b. These joysticks 16a and 16b output signals according to an operation made from an outside to the control device 17, as guidance instruction information for magnetically guiding the capsule endoscope 10 and setting information for setting a predetermined observation mode to the capsule endoscope 10. Here, the guidance instruction information includes information related to a movement to change the position of the capsule endoscope 10, information related to a movement to change an inclined angle (an angle with respect to the vertical axis) of the capsule endoscope 10, information related to a movement to change azimuth angles (angles around the vertical axis) of the visual fields (the imaging units 102 and 103 illustrated in FIG. 2) of the capsule endoscope 10, and the like. Further, the observation mode includes a floating mode for observation of the inside of the subject 2 in a state where the capsule endoscope 10 floats in the liquid W (see FIG. 2) introduced into the subject 2, an underwater mode for observation of the inside of the subject 2 in a state where the capsule endoscope 10 is sunk near a bottom portion of the liquid W, and the like.

Figure 5:
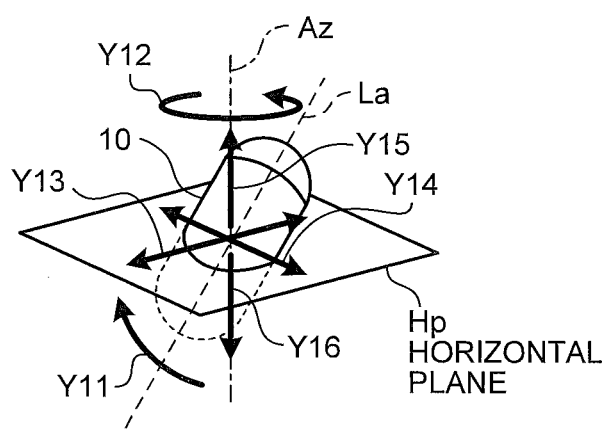
FIG. 5 is a schematic diagram illustrating movements of the capsule endoscope according to operations to parts of the operation input device illustrated in FIGS. 4A and 4B.

FIG. 4A is a front view of the joysticks 16a and 16b, and FIG. 4B is a right side view of the joystick 16a. Further, FIG. 5 is a schematic diagram illustrating movements of the capsule endoscope 10 according to operations to parts of the joysticks 16a and 16b. As illustrated in FIG. 4A, the joysticks 16a and 16b have a configuration that enables tilting operations in an up and down direction and in a right and left direction.

As illustrated in FIG. 4B, an up button 16c and a down button 16d are provided on a back surface of the joystick 16a. The up button 16c outputs the guidance instruction information to the control device 17 by being pressed, the guidance instruction information instructing upward guidance of the capsule endoscope 10. Accordingly, an up movement to proceed upward along a vertical axis Az illustrated in FIG. 5 like the arrow Y15 is instructed. Meanwhile, the down button 16d outputs the guidance instruction information to the control device 17 by being pressed, the guidance instruction information instructing downward guidance of the capsule endoscope 10. Accordingly, a down movement to proceed downward along the vertical axis Az illustrated in FIG. 5 like the arrow Y16 is instructed.

A capture button 16e is provided on an upper portion of the joystick 16a. The capture button 16e captures the in-vivo image on the display device 18 by being pressed. Further, an approach button 16f is provided on an upper portion of the joystick 16b. The approach button 16f outputs the guidance instruction information to the control device 17 by being pressed, the guidance instruction information guiding the capsule endoscope 10 to cause the imaging unit 102 side or the imaging unit 103 side of the capsule endoscope 10 to come closer to an imaging target of the imaging unit 102 or 103.

As illustrated in FIG. 4A, a tilting direction of the joystick 16a in the up and down direction illustrated by the arrow Y11j corresponds to a tilting guiding direction in which a distal end of the capsule endoscope 10 shakes its head to pass through the vertical axis Az, like the arrow Y11 of FIG. 5. A tilting direction of the joystick 16a in the right and left direction illustrated by the arrow Y12j corresponds to a rotation guiding direction in which the capsule endoscope 10 is rotated around the vertical axis Az, like the arrow Y12 of FIG. 5.

A tilting direction of the joystick 16b in the up and down direction illustrated by the arrow Y13j corresponds to a horizontal backward guiding direction or a horizontal forward guiding direction in which the capsule endoscope 10 proceeds in a direction into which the long axis La of the capsule endoscope 10 is projected on a horizontal plane Hp, like the arrow Y13 of FIG. 5. A tilting direction of the joystick 16b in the right and left direction illustrated by the arrow Y14j corresponds to a horizontal right guiding direction or a horizontal left guiding direction in which the capsule endoscope 10 proceeds perpendicularly to a direction into which the long axis La is projected on the horizontal plane Hp, like the arrow Y14 of FIG. 5.

The control device 17 takes in the image data output from the receiving device 15 and applies predetermined image processing to the image data to generate the in-vivo image, and takes in the position detection output from the signal processing device 13 to detect the position and the posture of the capsule endoscope 10 in the subject 2, and displays the in-vivo image, and the position and the posture of the capsule endoscope 10 in the display device 18 in a predetermined format. Further, the control device 17 outputs a control signal to the signal generating device 14 according to the signal input from the operation input device 16, thereby to generate the magnetic field for guiding the capsule endoscope 10 from the magnetic field generating device 12. Such a control device 17 is configured from a workstation, a personal computer, or the like.

Figure 6:
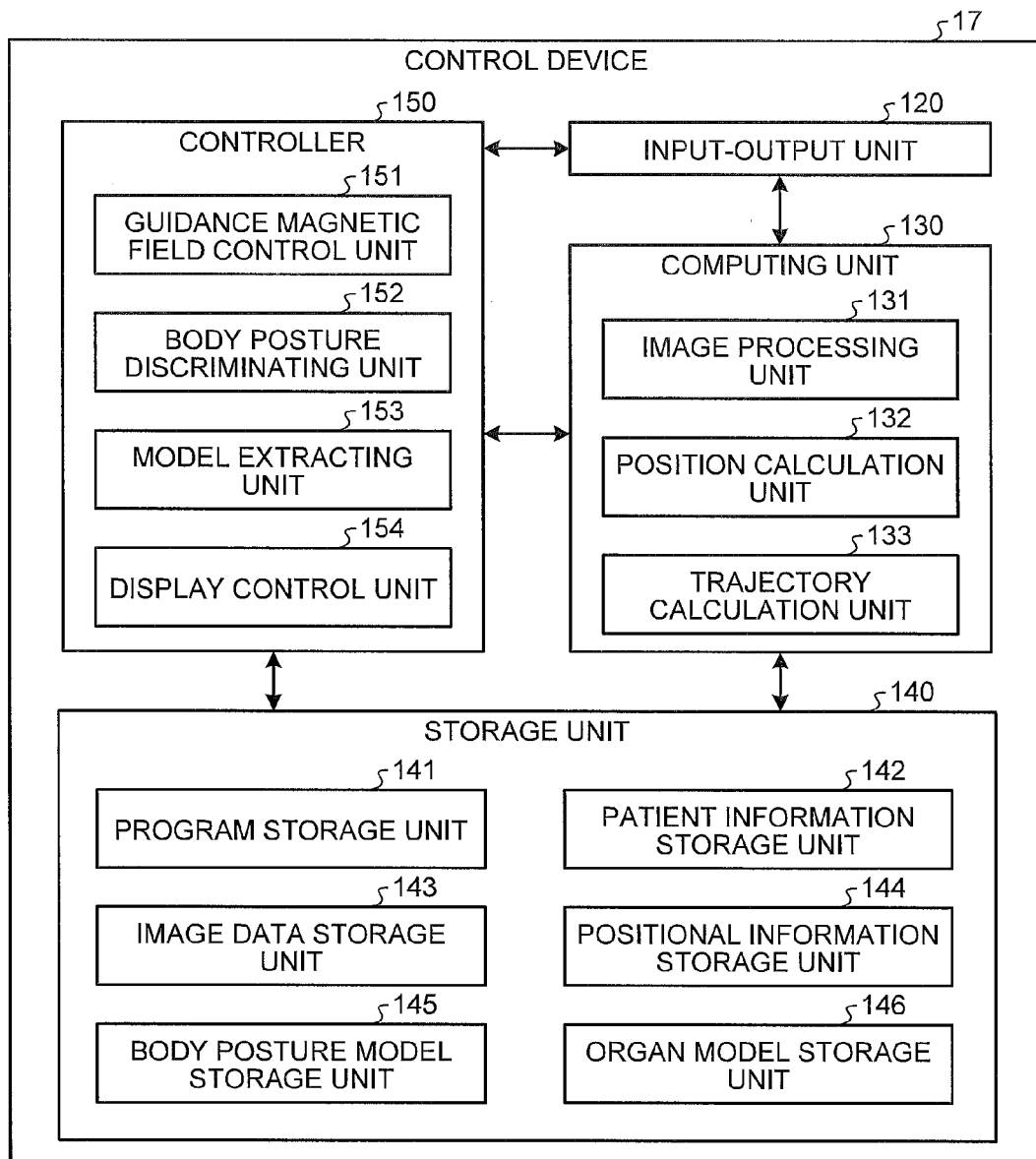
FIG. 6 is a block diagram illustrating a configuration example of a control device illustrated in FIG. 1.

FIG. 6 is a block diagram illustrating a configuration example of the control device 17. As illustrated in FIG. 6, the control device 17 includes an input-output unit 120, a computing unit 130, a storage unit 140, and a controller 150.

The input-output unit 120 is an external interface that performs input/output of information with external devices. The input-output unit 120 receives various data and command signals output from the external devices such as the signal processing device 13, the receiving device 15, and the operation input device 16 and outputs the received data and command signals to the computing unit 130 or the controller 150, and outputs various data and control signals output from the computing unit 130 or the controller 150 to the external devices such as the signal generating device 14 and the display device 18.

The computing unit 130 is realized by hardware such as a CPU, and applies a predetermined calculation process to the various data input to the control device 17 by reading various programs stored in a program storage unit 141 described below. To be specific, the computing unit 130 includes an image processing unit 131, a position calculation unit 132, and a trajectory calculation unit 133.

The image processing unit 131 generates image data for display by applying image processing to the image data taken in from the receiving device 15, such as white balance processing, demosaicing, color conversion, density conversion (gamma conversion or the like), smoothing (noise removal or the like), sharpening (edge enhancement or the like).

The position calculation unit 132 calculates the position and the posture of the capsule endoscope 10 in the subject 2 based on the position detection signal taken in from the signal processing device 13, and generates position information that indicates the position and the posture of the capsule endoscope 10.

The trajectory calculation unit 133 calculates a trajectory of the capsule endoscope 10 in the subject 2 based on the position information generated by the position calculation unit 132.

The storage unit 140 is realized by a semiconductor memory such as a flash memory, a RAM, or a ROM, a recording medium such as an HDD, an MO, a CD-R, or a DVD-R, and a writing/reading device. The storage unit 140 includes the program storage unit 141 that stores programs for causing the control device 17 to be operated and execute various functions and various types of information, a patient information storage unit 142 that stores information related to the subject 2 that is a patient, an image data storage unit 143 that stores the image data for display generated by the image processing unit 131, a position information storage unit 144 that stores the position information generated by the position calculation unit 132, a body posture model storage unit 145, and an organ model storage unit 146.

Figure 7A:
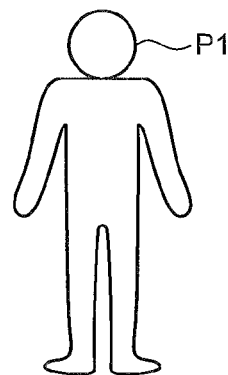
FIGS. 7A to 7D are schematic diagrams illustrating examples of body posture models stored in a body posture model storage unit illustrated in FIG. 6.
Figure 7B:
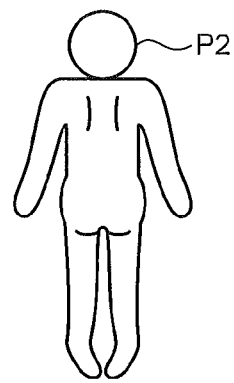
Figure 7C:
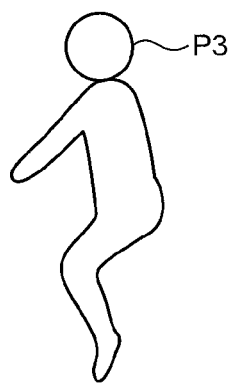
Figure 7D:
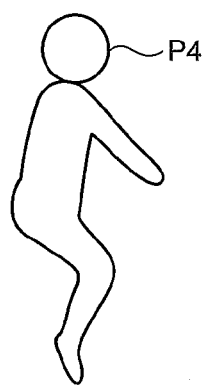

The body posture model storage unit 145 stores image data of a plurality of body posture models that schematically illustrate the body postures taken by the subject 2 according to an instruction of the user such as a doctor in an examination with the capsule endoscope 10. FIGS. 7A to 7D are schematic diagrams illustrating examples of the body posture models. A body posture model P1 illustrated in FIG. 7A is a model in which the subject 2 in supine position is projected on a horizontal plane. A body posture model P2 illustrated in FIG. 7B is a model in which the subject 2 in prone position is projected on a horizontal plane. A body posture model P3 illustrated in FIG. 7C is a model in which the subject 2 in decubitus left position is projected on a horizontal plane. A body posture model P4 illustrated in FIG. 7D is a model in which the subject 2 in decubitus right position is projected on a horizontal plane.

Figure 8A:
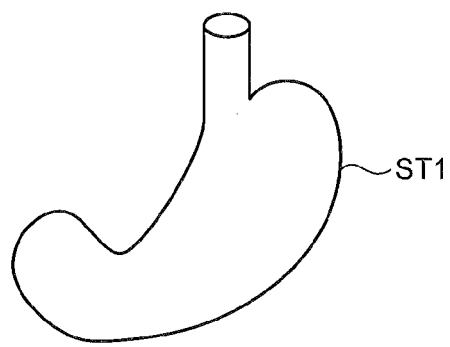
FIGS. 8A to 8D are schematic diagrams illustrating examples of organ models stored in an organ model storage unit illustrated in FIG. 6.
Figure 8B:
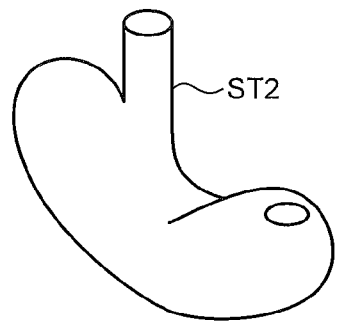
Figure 8C:
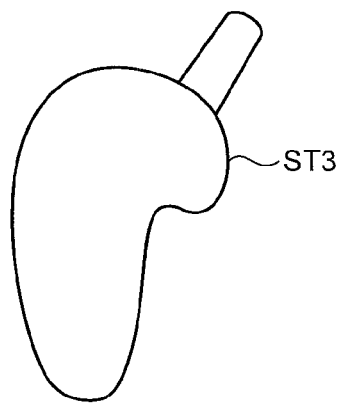
Figure 8D:
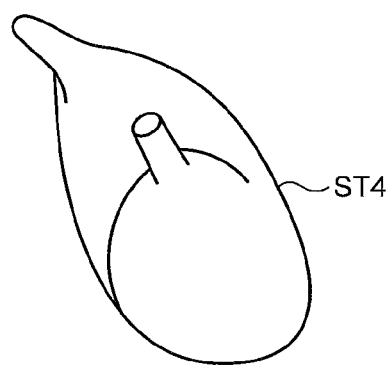

The organ model storage unit 146 stores image data of a plurality of organ models that schematically illustrate an organ to be examined by the capsule endoscope 10. Note that, in the first embodiment, the organ to be examined by the capsule endoscope 10 is a stomach as an example. FIGS. 8A to 8D are schematic diagrams illustrating examples of the organ models. An organ model ST1 illustrated in FIG. 8A is a model in which the stomach in supine position is projected on a horizontal plane. An organ model ST2 illustrated in FIG. 8B is a model in which the stomach in prone position is projected on a horizontal plane. An organ model ST3 illustrated in FIG. 8C is a model in which the stomach in decubitus left position is projected on a horizontal plane. An organ model ST4 illustrated in FIG. 8D is a model in which the stomach in decubitus right position is projected on a horizontal plane. The image data of these organ models ST1 to ST4 are stored in association with the image data of the body posture models stored in the body posture model storage unit 145 for each body posture.

The controller 150 is realized by hardware such as a CPU, and transfers commands and data to respective units that constitute the control device 17, and integrally controls the operation of the entire control device 17, according to various signals input to the control device 17, by reading the various programs stored in the program storage unit 141.

To be specific, the controller 150 includes the guidance magnetic field control unit 151 that controls the signal generating device 14 based on the guidance instruction information input from the operation input device 16, a body posture discriminating unit 152 that discriminates the body posture of the subject 2, a model extracting unit 153 that respectively extracts the body posture model and the organ model according to the body posture discriminated by the body posture discriminating unit 152 from the plurality of body posture models stored in the body posture model storage unit 145 and the plurality of organ models stored in the organ model storage unit 146, and a display control unit 154 that controls a display operation in the display device 18.

The guidance magnetic field control unit 151 calculates a guiding direction and a guidance amount of the capsule endoscope 10 according to the operation to the operation input device 16 based on the guidance instruction information input from the operation input device 16, outputs a control signal corresponding to the guiding direction and the guidance amount to the signal generating device 14, and generates a signal for driving the magnetic field generating device 12. When the operation input device 16 is made of the joysticks 16a and 16b illustrated in FIG. 4, for example, control as follows is performed.

When the guidance instruction information corresponding to the tilting operation of the arrow Y11$j$ (see FIG. 4) of the joystick 16a is input from the operation input device 16 to the control device 17, the guidance magnetic field control unit 151 calculates the guiding direction of the distal end of the capsule endoscope 10 on an absolute coordinate system according to the tilting direction of the joystick 16a based on the guidance instruction information and calculates the guidance amount according to the tilting operation of the joystick 16a, and outputs the control signal corresponding to the guiding direction and the guidance amount.

When the guidance instruction information corresponding to the tilting operation of the arrow Y12$j$ (see FIG. 4) of the joystick 16a is input from the operation input device 16 to the control device 17, the guidance magnetic field control unit 151 calculates the guiding direction of the distal end of the capsule endoscope 10 on the absolute coordinate system according to the tilting direction of the joystick 16a based on the guidance instruction information and calculates the guidance amount according to the tilting operation of the joystick 16a, and outputs the control signal corresponding to the guiding direction and the guidance amount.

When the guidance instruction information corresponding to the tilting operation of the arrow Y13j (see FIG. 4) of the joystick 16b is input from the operation input device 16 to the control device 17, the guidance magnetic field control unit 151 calculates the guiding direction and the guidance amount of the distal end of the capsule endoscope 10 on the absolute coordinate system according to the tilting direction of the joystick 16b based on the guidance instruction information, and outputs the control signal corresponding to the guiding direction and the guidance amount.

When the guidance instruction information corresponding to the tilting operation of the arrow Y14j (see FIG. 4) of the joystick 16b is input from the operation input device 16 to the control device 17, the guidance magnetic field control unit 151 calculates the guiding direction and the guidance amount of the distal end of the capsule endoscope 10 on the absolute coordinate system according to the tilting direction of the joystick 16b based on the guidance instruction information, and outputs the control signal corresponding to the guiding direction and the guidance amount.

When the guidance instruction information corresponding to a pressing operation of the arrow Y15j or Y16j (see FIG. 4) of the up button 16c or the down button 16d is input from the operation input device 16 to the control device 17, the guidance magnetic field control unit 151 calculates the guiding direction and the guidance amount of the distal end of the capsule endoscope 10 on the absolute coordinate system according to the pressed button based on the guidance instruction information, and outputs the control signal corresponding to the guiding direction and the guidance amount.

The body posture discriminating unit 152 discriminates the body posture of the subject 2 based on the signal input from the operation input device 16. Further, the body posture discriminating unit 152 transmits the information that indicates the discriminated body posture to the storage unit 140 to store the information in association with the image data generated by the image processing unit 131.

The model extracting unit 153 extracts the body posture model according to the discrimination result by the body posture discriminating unit 152 from the plurality of body posture models stored in the body posture model storage unit 145, and extracts the organ model associated with the extracted body posture model from the plurality of organ models stored in the organ model storage unit 146.

The display control unit 154 displays the in-vivo image based on the image data for display generated by the image processing unit 131, and the related information such as the patient information, the position information, and the information that indicates the body posture of the subject 2, in the display device 18 in a predetermined format during the examination with the capsule endoscope 10. Further, the display control unit 154 displays the in-vivo image based on the image data stored in the image data storage unit 143 and the related information, in the display device 18 in a predetermined format, when the user such as a doctor diagnoses the in-vivo image obtained by the examination. In this case, higher-definition display device than the display device 18 used during the examination may be used.

The display device 18 is configured from a liquid crystal display or an organic electro luminescence (EL) display.

Figure 9:
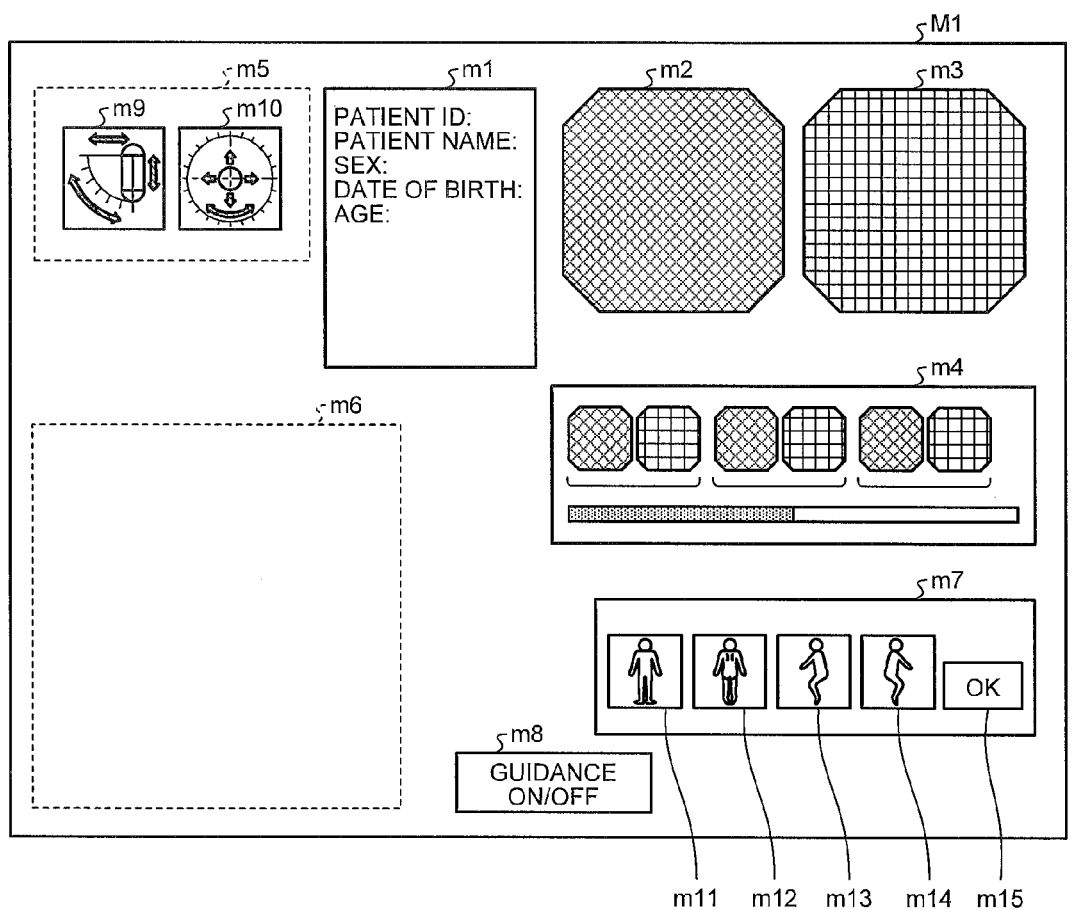
FIG. 9 is a schematic diagram illustrating an example of a screen on a display device.

FIG. 9 is a schematic diagram illustrating an example of a screen on the display device 18 under control of the display control unit 154. As illustrated in FIG. 9, a screen M1 includes a patient information display region m1 in which the patient information such as a patient ID, a patient name, a sex of the patient, a date of birth, and an age, two in-vivo image display regions m2 and m3 that are regions in which the in-vivo images acquired by the imaging units 102 and 103 are respectively displayed, a captured image display region m4 in which the in-vivo image captured with the pressing operation to the capture button 16e is displayed, an operation information display region m5 in which the operation information for the capsule endoscope 10 is displayed, a body posture information display region m6 in which the body posture information of the subject 2 is displayed, a body posture button display region m7 for allowing the user to input the body posture of the subject 2, and a guidance ON/OFF button m8 for allowing the user to input a switching instruction of ON/OFF of the guidance function to the capsule endoscope 10.

The operation information display region m5 is a region in which a posture view m9 that indicates the posture of the capsule endoscope 10 in a vertical plane and a posture view m10 that indicates the posture in a horizontal plane. In the posture views m9 and m10, a plurality of directions into which the capsule endoscope 10 can be guided is illustrated by arrows. When the operation input to guide the capsule endoscope 10 into any direction is given, a display color of the arrow corresponding to the input direction, of the arrows, is changed. Accordingly, the guiding operation by the user is assisted.

The posture of the capsule endoscope 10 displayed in the posture views m9 and m10 indicates the posture corresponding to the guidance instruction information input from the operation input device 16. Here, the guidance instruction information input from the operation input device 16 is reflected in the control signal that controls the magnetic field generating device 12 that generates the magnetic field that guides the capsule endoscope 10 and the signal generating device 14. Therefore, the posture of the capsule endoscope 10 displayed in the posture views m9 and m10 can be considered to be nearly the same as the actual posture of the capsule endoscope 10 in the subject 2.

The body posture information display region m6 is a region in which the body posture information that is information indicating the body posture of the subject 2 and the state of the organ in that body posture. To be specific, the body posture model and the organ model extracted by the model extracting unit 153 are displayed on the body posture information display region m6.

Icons m11 to m14 corresponding to the body posture models P1 to P4 (see FIGS. 7A to 7D) and an OK button m15 are displayed on the body posture button display region m7. When any of the icons m11 to m14 is selected with a predetermined pointer operation (for example, a click) using the operation input device 16 (for example, a touch panel or a mouse) on the screen M1, and the OK button m15 is further pressed after the selection, a body posture selection signal that indicates the body posture corresponding to the selected icon is input to the controller 150.

Note that a special input button for allowing the user to select the body posture of the subject 2 may be provided in the operation input device 16 instead of providing the body posture button display region m7 on the screen M1.

The guidance ON/OFF button m8 is used when the user inputs a command to start (resume) or terminate (interrupt) the guidance of the capsule endoscope 10. Every time the guidance ON/OFF button m8 is pressed once with the predetermined pointer operation using the operation input device 16 (for example, a touch panel or a mouse) on the screen M1, a guidance ON/OFF switching signal that switches ON and OFF of the guidance function is input to the controller 150. During ON of the guidance function by the guidance ON/OFF switching signal, the magnetic guidance of the capsule endoscope 10 using the operation input device 16 is available.

Note that a special switch or button for allowing the user to switch ON/OFF of the guidance function of the capsule endoscope 10 may be provided in the operation input device 16 instead of providing the guidance ON/OFF button m8 on the screen M1.

The user operates the operation input device 16 while referring to such a screen M1, thereby to cause the capsule endoscope 10 to image a desired region in the subject 2. Note that, as illustrated in FIG. 2, in the case where the capsule endoscope 10 includes the two imaging units 102 and 103, a display for identifying the imaging unit that is intended to be guided and operated by the user may be added on the screen M1. For example, when the user intends to guide and operate the imaging unit 102, it is favorable to surround the in-vivo image display region m2 where the in-vivo image imaged by the imaging unit 102 is displayed, with a frame, or to display texts such as "during guiding operation" near the in-vivo image display region m2.

Figure 10:
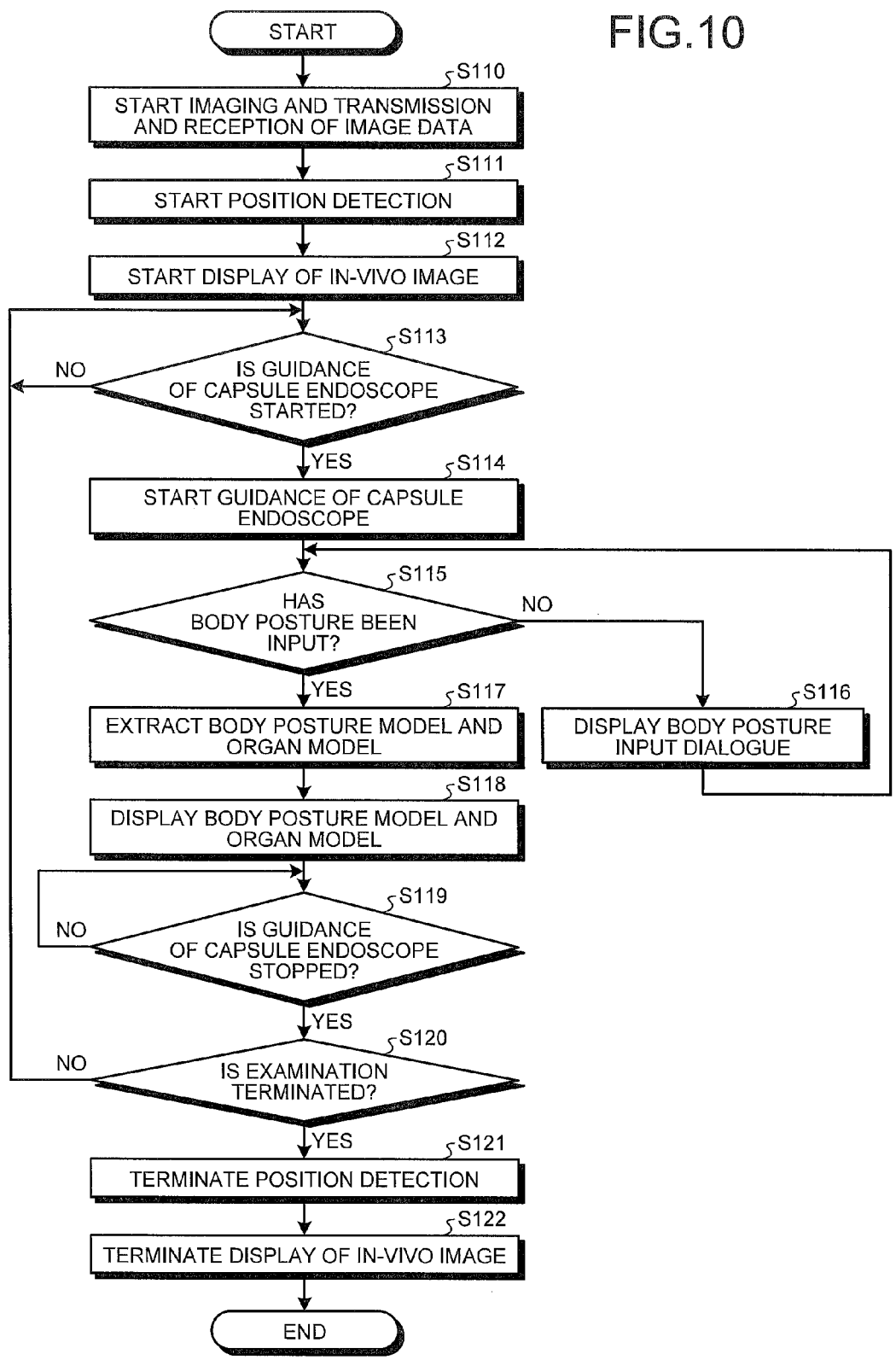
FIG. 10 is a flowchart illustrating a movement of the capsule endoscope system illustrated in FIG. 1.

Next, the operation of the capsule endoscope system 1 illustrated in FIG. 1 will be described with reference to FIG. 10. First, the user introduces the liquid W (see FIG. 3) to the subject 2, prior to the examination with the capsule endoscope 10.

In step S110, when the power supply of the capsule endoscope 10 is turned ON, the capsule endoscope 10 starts imaging, and starts wireless transmission of the image signal. Further, the receiving device 15 starts reception of the image signal wirelessly transmitted from the capsule endoscope 10. In response to that, the image processing unit 131 of the control device 17 takes in the digital image signal (image data) output from the receiving device 15 and applies the predetermined image processing, thereby to generate the image data for display that indicates the in-vivo image. The image data for display is sequentially stored in the image data storage unit 143. The user such as a doctor instructs the subject 2 to swallow the capsule endoscope 10 in this state.

In step S111, the capsule endoscope system 1 starts position detection of the capsule endoscope 10. To be specific, the position detection device 11 detects the alternating magnetic field generated by the magnetic field generating unit 107 of the capsule endoscope 10 and outputs the detection signal, and the signal processing device 13 takes in the detection signal and applies the predetermined signal processing, thereby to generate the digital position detection signal (position detection data). The position calculation unit 132 of the control device 17 calculates the position and posture of the capsule endoscope 10 based on the position detection data, and sequentially stores the position and the posture in the position information storage unit 144 as the position information.

In step S112, the display control unit 154 of the control device 17 causes the display device 18 to start display of the in-vivo image in the format of the screen M1 illustrated in FIG. 9, for example, using the image data for display sequentially generated by the image processing unit 131.

In step S113, the controller 150 determines whether the guidance ON/OFF switching signal according to the pointer operation to the guidance ON/OFF button m8 on the screen M1 has been input, as the command to start (or resume) the guidance of the capsule endoscope 10. When the command to start (or resume) the guidance of the capsule endoscope 10 is not input (No in step S113), the controller 150 stands by until the start (or resuming) of the guidance is instructed.

When the command to start (or resume) the guidance of the capsule endoscope 10 has been input (Yes in step S113), the controller 150 starts the magnetic guidance of the capsule endoscope 10 (step S114). That is, the guidance magnetic field control unit 151 generates the control signal based on the input guidance instruction information and outputs the control signal to the signal generating device 14. In response to that, the signal generating device 14 drives the magnetic field generating device 12 to generate the magnetic field. Accordingly, the magnetic guidance of the capsule endoscope 10 according to the operation to the operation input device 16 is realized.

In following step S115, the controller 150 determines whether the body posture of the subject 2 has been input. When the body posture selection signal corresponding to any of the icons m11 to m14 has been input according to the pointer operation to the screen M1, the controller 150 determines that the body posture has been input (Yes in step S115).

When the body posture is not input even when a predetermined time has passed after the start of the guidance of the capsule endoscope 10 (No in step S115), the display control unit 154 causes the display device 18 to display a body posture input dialogue for prompting the user to input the body posture (step S116).

Figure 11:
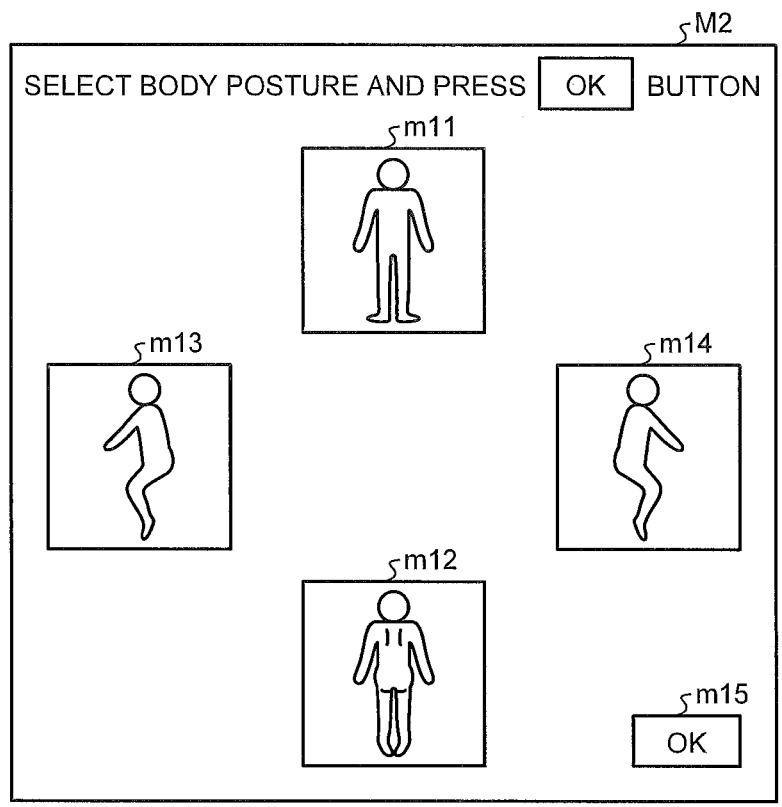
FIG. 11 is a schematic diagram illustrating an example of a body posture input dialogue.

FIG. 11 is a schematic diagram illustrating an example of a body posture input dialogue. A body posture input dialogue M2 illustrated in FIG. 11 includes a text message such as "please select body posture and press OK button", the icons m11 to m14 corresponding to the body posture models P1 to P4, and the OK button m15. Any of the icons m11 to m14 is selected with the pointer operation to the body posture input dialogue M2, and the OK button m15 is pressed, so that the body posture selection signal that indicates the body posture corresponding to the selected icon is input to the controller 150.

Figure 12:
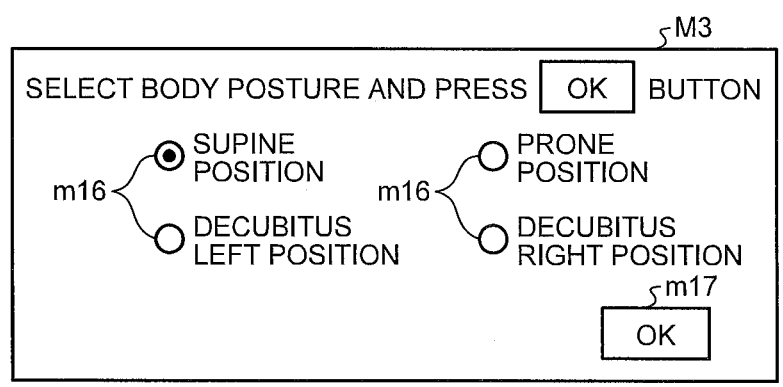
FIG. 12 is a schematic diagram illustrating another example of the body posture input dialogue.

FIG. 12 is a schematic diagram illustrating another example of the body posture input dialogue. A body posture input dialogue M3 illustrated in FIG. 12 includes a text message such as "please select body posture and press OK button", texts that indicates the body posture such as "supine", "prone", "decubitus left", and "decubitus right", radio buttons m16 displayed near the texts of the body postures, and an OK button m17. Any of the radio buttons m16 is selected with the pointer operation to the body posture input dialogue M3 and the OK button m17 is pressed, so that the body posture selection signal that indicates the body posture corresponding to the selected radio button m16 is input to the controller 150. FIG. 12 illustrates a state where the supine is selected.

When a special input button that allows the user to select the body posture is provided in the operation input device 16, for example, a text message such as "please input body posture" may just be displayed in the body posture input dialogue. Following that, the operation of the capsule endoscope system 1 is returned to step S115.

When the body posture of the subject 2 is input (Yes in step S115), the model extracting unit 153 extracts the body posture model according to the input body posture (body posture selection signal) from the plurality of body posture models stored in the body posture model storage unit 145, and extracts the organ model corresponding to the extracted body posture model from the plurality of organ models stored in the organ model storage unit 146 (step S117).

In following step S118, the display control unit 154 causes the display device 18 to display the body posture model and the organ model extracted by the model extracting unit 153.

Figure 13:
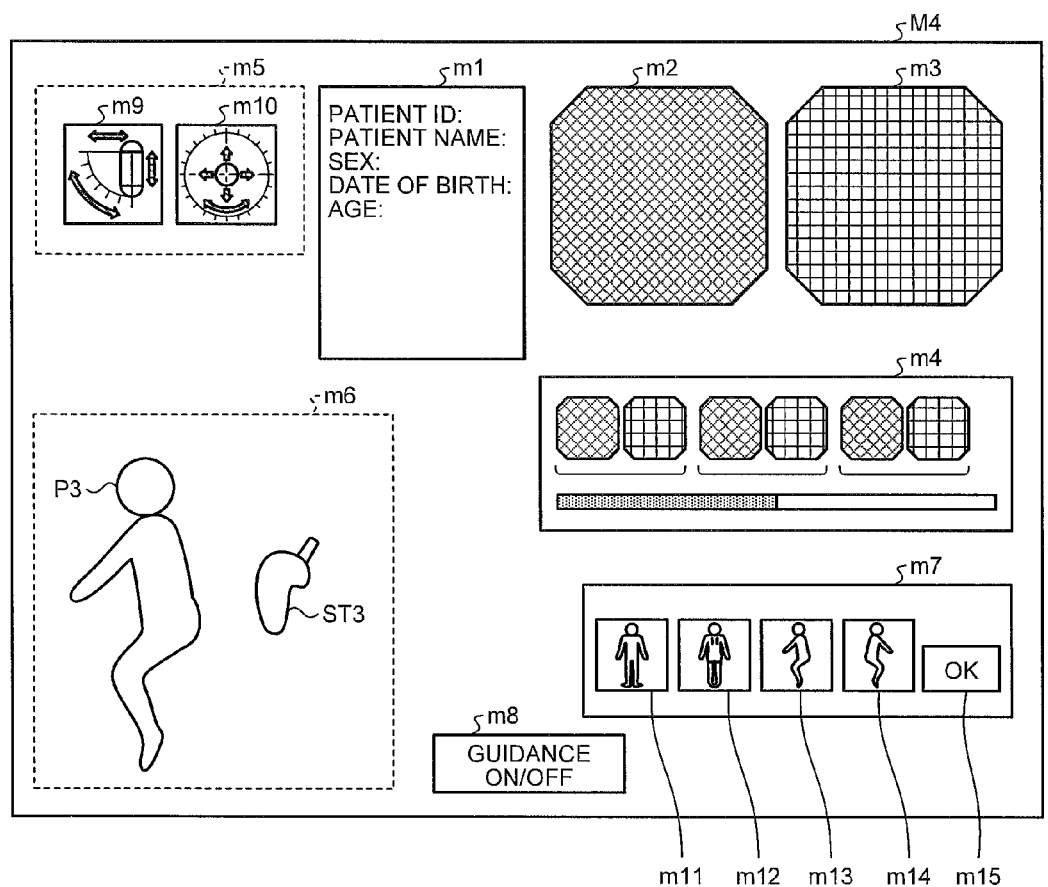
FIG. 13 is a schematic diagram illustrating an example of a screen on which a body posture model and an organ model are displayed.

FIG. 13 is a schematic diagram illustrating the screen on which the body posture model and the organ model are displayed, and illustrates an example of displaying a body posture model P3 of the decubitus left and the organ model ST3 side by side in the body posture information display region m6 on the screen M4. The user can easily grasp the positional relationship between the visual fields of the imaging units 102 and 103 of the capsule endoscope 10 guided and operated by him/her using the operation input device 16 and the organ, by reference to the body posture model P3 and the organ model ST3 displayed as illustrated. Note that the arrangement of the body posture model P3 and the organ model ST3 is not limited to the example illustrated in FIG. 13 as long as the user can see both the model and organ at the same time in the arrangement. To be specific, both the model and organ may be superimposed and displayed. In this case, the user can more easily grasp relationships of a relative position and direction between the body posture model and the organ model.

In following step S119, the controller 150 determines whether the command to stop the guidance of the capsule endoscope 10 has been input. Here, when changing the body posture of the subject 2, the user instructs the subject 2 to change the body posture after stopping the guidance function of the capsule endoscope 10 once, then turns ON the guidance function of the capsule endoscope 10.

When the guidance ON/OFF switching signal has been input according to the pointer operation to the guidance ON/OFF button m8 on the screen M1, for example, the controller 150 determines that the command to stop the guidance has been input (Yes in step S119). Meanwhile, when the guidance ON/OFF switching signal is not input, the controller 150 determines that stop of the guidance has not been instructed (No in step S119). In this case, the controller 150 continues the guidance of the capsule endoscope 10 according to the operation to the operation input device 16 until the stop of the guidance is instructed.

When the command to stop the guidance of the capsule endoscope 10 has been input (Yes in step S119), the controller 150 then determines whether to terminate the examination with the capsule endoscope 10 (step S120). When the operation to terminate the examination has been input by the user, or when an output of the image signal from the receiving device 15 is stopped (that is, the wireless transmission of the image signal from the capsule endoscope 10 is stopped), for example, the controller 150 determines to terminate the examination (Yes in step S120).

When the examination with the capsule endoscope 10 is not terminated (No in step S120), the operation of the capsule endoscope system 1 is returned to step S113.

Meanwhile, when the examination with the capsule endoscope 10 is terminated (Yes in step S120), the control device 17 stops the operation of the signal processing device 13, and terminates the detection of the position of the capsule endoscope 10 (step S121).

In following step S122, the control device 17 terminates the display of the in-vivo image in the display device 18. Following that, the operation of the capsule endoscope system 1 is terminated.

As described above, according to the first embodiment, even if the body posture of the subject 2 is changed, the user can easily grasp the positional relationship between the capsule endoscope 10 operated through the operation input device 16, and the subject 2 and the organ, and the imaging direction, by reference to the body posture model and the organ model displayed on the display device 18. Especially, the body posture models P1 to P4 and the organ models ST1 to ST4 are models in which the subject 2 and the organ are projected on the horizontal plane. Therefore, the user can grasp the states of the subject 2 and the organ with a sense similar to a case where the user views the subject 2 from above the bed 3 in a bird's eye manner. Therefore, the user can accurately perform the guiding operation of the capsule endoscope 10, and cause the capsule endoscope 10 to image the desired region in the subject 2 and perform the observation.

Further, according to the first embodiment, when the guidance function of the capsule endoscope 10 is turned ON, the body posture input dialogue is displayed on the display device 18. Therefore, forgetting of input of the body posture by the user can be prevented. Therefore, the body posture model that indicates the actual body posture of the subject 2 and the corresponding organ model can be displayed on the display device 18 during the examination on a constant basis. Further, the accurate information that indicates the body posture of the subject 2 can be associated with the image data. Therefore, the user can accurately grasp the positional relationship between the capsule endoscope 10, and the subject 2 and the organ of when the in-vivo image is imaged, and the imaging direction, by reference to the body posture information, when the user diagnoses the in-vivo image.

Modification 1

Next, a modification 1 of the first embodiment of the present invention will be described.

In the first embodiment, the user inputs the body posture of the subject 2. However, the body posture of the subject 2 may be automatically discriminated. To be specific, as a specific configuration example, a triaxial acceleration sensor is attached to a pad for an antenna 15a, the pad being to be stuck to the subject 2, and a body posture discriminating unit 152 discriminates a body posture of a subject 2 based on a direction of acceleration detected with the triaxial acceleration sensor, that is, a gravity direction. In this modification 1, steps S115 and S116 of FIG. 10 are omitted, and in step S117, a body posture model and an organ model are extracted based on the automatically discriminated body posture.

Second Embodiment

Next, a second embodiment of the present invention will be described.

A configuration of a capsule endoscope system according to the second embodiment is similar to the first embodiment (see FIG. 1), and is different from the first embodiment in a display format of body posture information displayed on a display device 18. To be specific, in the second embodiment, the display format of the body posture information is changed depending on whether magnetic guidance of a capsule endoscope 10 is being performed or not.

Figure 14:
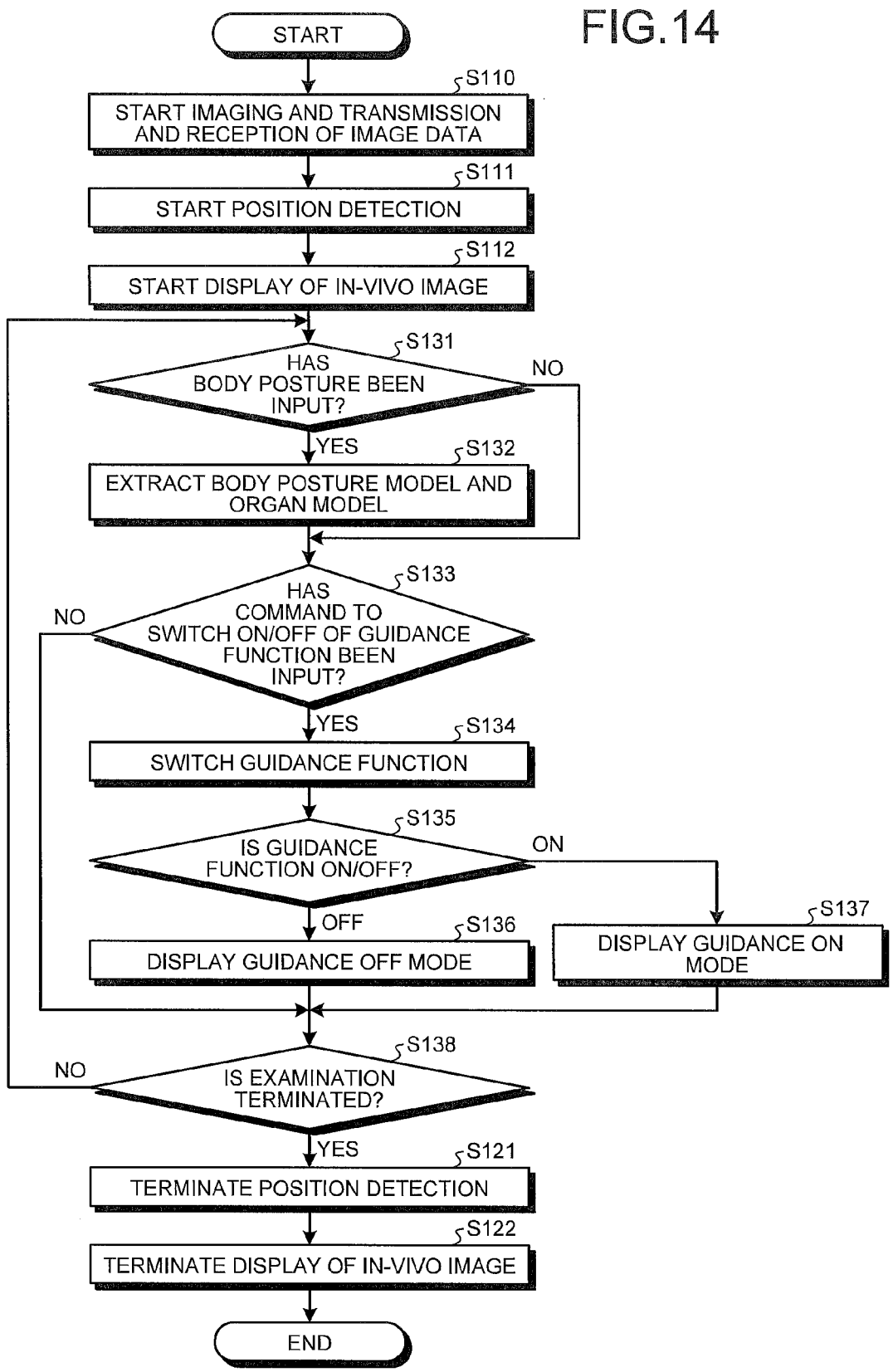
FIG. 14 is a flowchart illustrating a movement of a capsule endoscope system according to a second embodiment of the present invention.

An operation of a capsule endoscope system according to the second embodiment will be described with reference to FIG. 14. Note that steps S110 to S112 illustrated in FIG. 14 are similar to those in the first embodiment (see FIG. 10).

In step S131 following step S112, a controller 150 determines whether a body posture of a subject 2 has been input. When a body posture selection signal according to any of icons m11 to m14 has been input according to a pointer operation on a screen M1, for example, the controller 150 determines that the body posture has been input (Yes in step S131).

When the body posture of the subject 2 has been input (Yes in step S131), a model extracting unit 153 extracts a body posture model according to the input body posture (body posture selection signal) from a plurality of body posture models stored in a body posture model storage unit 145, and extracts an organ model corresponding to the extracted body posture model from a plurality of organ models stored in an organ model storage unit 146 (step S132). Meanwhile, when the body posture of the subject 2 is not input (No in step S131), an operation of a control device 17 proceeds to step S133.

In step S133, the controller 150 determines whether a guidance ON/OFF switching signal according to the pointer operation to the guidance ON/OFF button m8 illustrated in FIG. 9 has been input as a command to switch ON/OFF of a guidance function of the capsule endoscope 10. When the command to switch ON/OFF of the guidance function is not input (No in step S133), the operation of the control device 17 proceeds to step S138.

When the command to switch ON/OFF of the guidance function (Yes in step S133), a guidance magnetic field control unit 151 switches ON/OFF of the guidance function (step S134). That is, when the guidance function has been OFF until then, the guidance magnetic field control unit 151 starts reception of an input of a guidance instruction information output from an operation input device 16, generates a control signal based on the guidance instruction information, and outputs the control signal to the signal generating device 14. Accordingly, the magnetic guidance of the capsule endoscope 10 is started. Meanwhile, when the guidance function has been ON until then, the guidance magnetic field control unit 151 stops reception of the input of a guidance instruction information output from the operation input device 16.

In following step S135, a display control unit 154 distinguishes whether the guidance function is in the ON state or in the OFF state.

When the guidance function is in the OFF state (OFF in step S135), the display control unit 154 causes the display device 18 to display the body posture information of the subject 2 in a display format of the guidance OFF mode (step S136).

Figure 15A:
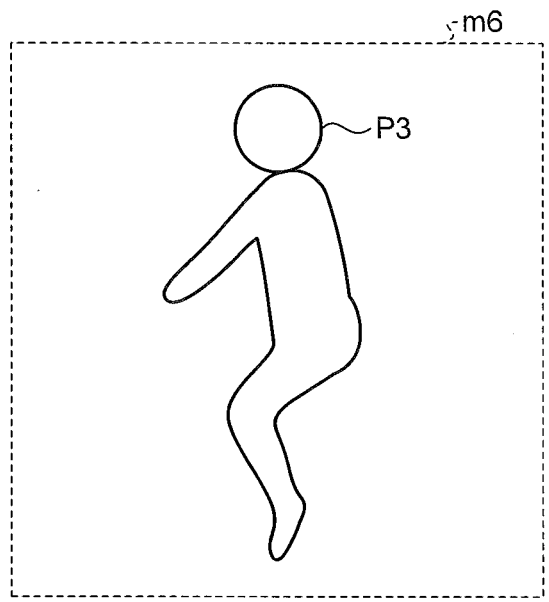
FIGS. 15A and 15B are schematic diagrams illustrating display examples of body posture information in the second embodiment.

FIG. 15A is a schematic diagram illustrating a display example of the body posture information in the guidance OFF mode. In the guidance OFF mode, the display control unit 154 displays only the body posture model extracted by the model extracting unit 153 in the body posture information display region m6 (see FIG. 9). FIG. 15A illustrates an example in which a body posture model P3 in decubitus left position is displayed.

Meanwhile, when the guidance function is in the ON state (ON in step S135), the display control unit 154 causes the display device 18 to display the body posture information of the subject 2 in a display format of the guidance ON mode (step S137).

Figure 15B:
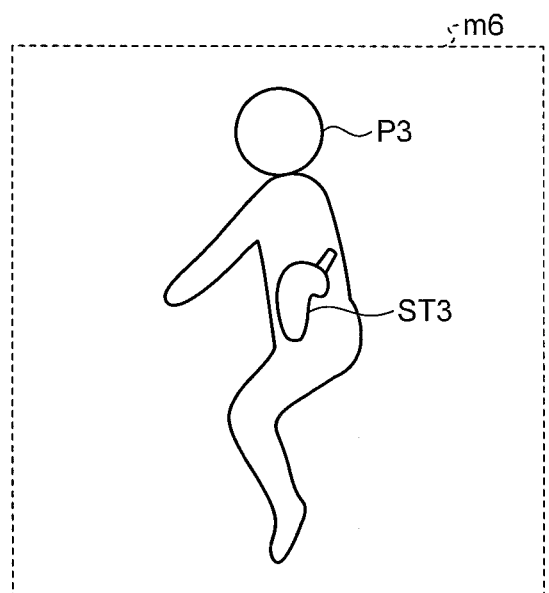

FIG. 15B is a schematic diagram illustrating a display example of the body posture information in the guidance ON mode. In the guidance ON mode, the display control unit 154 superimposes the organ model on the body posture model extracted by the model extracting unit 153 and displays the superimposed image in the body posture information display region m6 (see FIG. 9). FIG. 15B illustrates an example in which an organ model ST3 is superimposed on the body posture model P3 in decubitus left position.

In step S138, the controller 150 determines whether to terminate the examination with the capsule endoscope 10. When an input of image data from a receiving device 15 is stopped (that is, wireless transmission of the image data from the capsule endoscope 10 is stopped), for example, the controller 150 determines to terminate the examination (Yes in step S138).

When the examination with the capsule endoscope 10 is not terminated (No in step S138), the operation of the capsule endoscope system 1 is returned to step S131.

Meanwhile, when the examination with the capsule endoscope 10 is terminated (Yes in step S138), the operation of the capsule endoscope system 1 proceeds to step S121. Steps S121 and S122 are similar to those in the first embodiment (see FIG. 10).

As described above, according to the second embodiment, when the guidance function is OFF, only the body posture model is displayed in the body posture information display region m6, the user can grasp the entire state related to the subject 2 and the capsule endoscope 10 before performing the guiding operation of the capsule endoscope 10. Meanwhile, when the guidance function is ON, the organ model is superimposed on the body posture model and the superimposed image is displayed in the body posture information display region m6. Therefore, the user can intensively grasp information necessary for guiding operation such as the state of the organ according to the body posture of the subject 2 and a relative relationship between the organ and the subject 2 during the guiding operation of the capsule endoscope 10.

Note that, even in the second embodiment, the body posture of the subject 2 may be automatically discriminated, similarly to the modification 1. In this case, step S131 of FIG. 14 is omitted, and the body posture model and the organ model are extracted based on the automatically discriminated body posture in step S132.

Modification 2-1

Next, a modification 2-1 of the second embodiment of the present invention will be described.

The display formats of the body posture information in the guidance OFF mode and in the guidance ON mode are not limited to the display formats exemplarily illustrated in FIGS. 15A and 15B. FIGS. 16A, 16B, 17A and 17B are schematic diagrams illustrating display examples of body posture information in a modification 2-1.

Figure 16A:
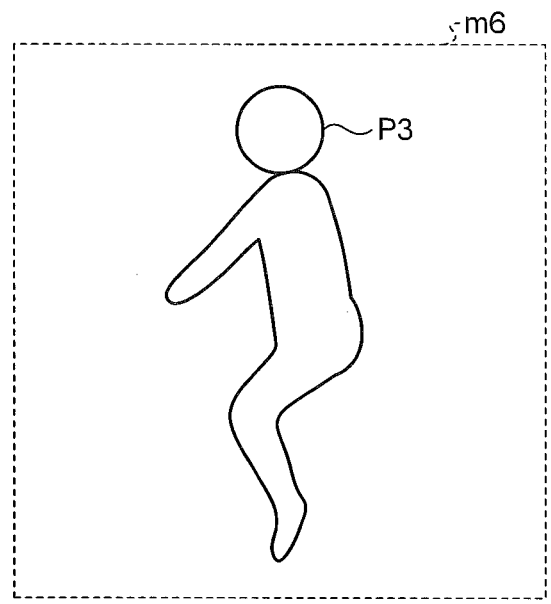
FIGS. 16A and 16B are schematic diagrams illustrating display examples of body posture information in a modification 2-1.
Figure 16B:
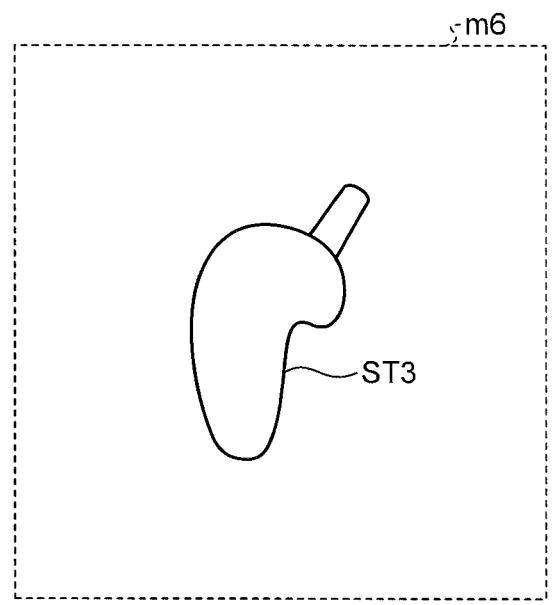

For example, in a guidance OFF mode, only a body posture model (for example, a body posture model P3) may be displayed, as illustrated in FIG. 16A. In a guidance ON mode, only an organ model (for example, an organ model ST3) may be displayed, as illustrated in FIG. 16B. In this case, a user can grasp an entire state related to a subject 2 and a capsule endoscope 10 before performing a guiding operation of the capsule endoscope 10. Further, the user can intensively grasp information necessary for the guiding operation (a state of an organ according to a body posture of the subject 2) while performing the guiding operation of the capsule endoscope 10.

Figure 17A:
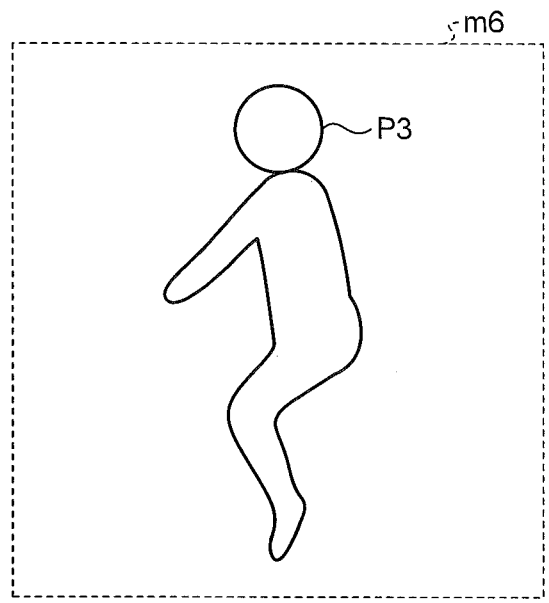
FIGS. 17A and 17B are schematic diagrams illustrating another display examples of the body posture information in modification 2-1.
Figure 17B:
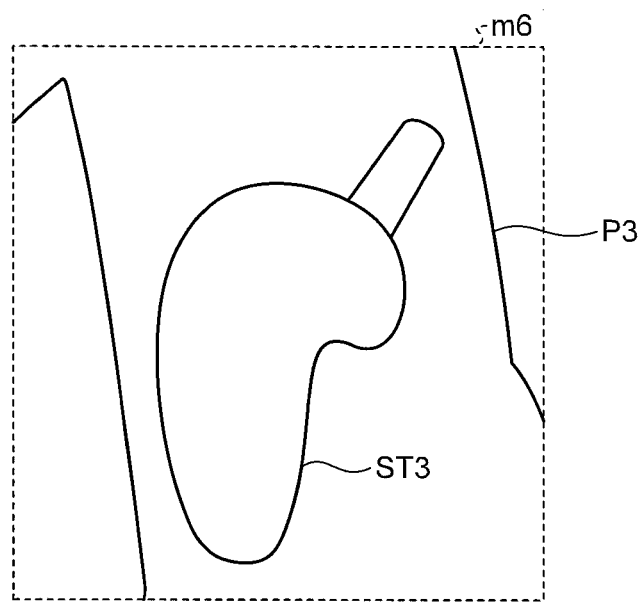

Further, in the guidance OFF mode, only the body posture model (for example, the body posture model P3) is displayed, as illustrated in FIG. 17A. In the guidance ON mode, the organ model (for example, the organ model ST3) may be superimposed on the body posture model (for example, the body posture model P3), and the superimposed image may be further enlarged and displayed, as illustrated in FIG. 17B. In this case, the user can totally grasp the state of the body posture of the subject 2 before performing the guiding operation of the capsule endoscope 10. Further, the user can easily and intensively grasp the information necessary for the guiding operation such as the state of the organ according to the body posture of the subject 2 and the relative relationship between the organ and the subject 2 while performing the guiding operation of the capsule endoscope 10.

Further, when the guiding operation is performed in an underwater mode in which an inside of the subject 2 is observed in a state where the capsule endoscope 10 is sunk in a liquid W (see FIG. 3) introduced into the subject 2, the body posture model and the organ model may be further enlarged and displayed than in a floating mode, in the guidance ON mode.

Third Embodiment

A third embodiment of the present invention will be described.

Figure 18:
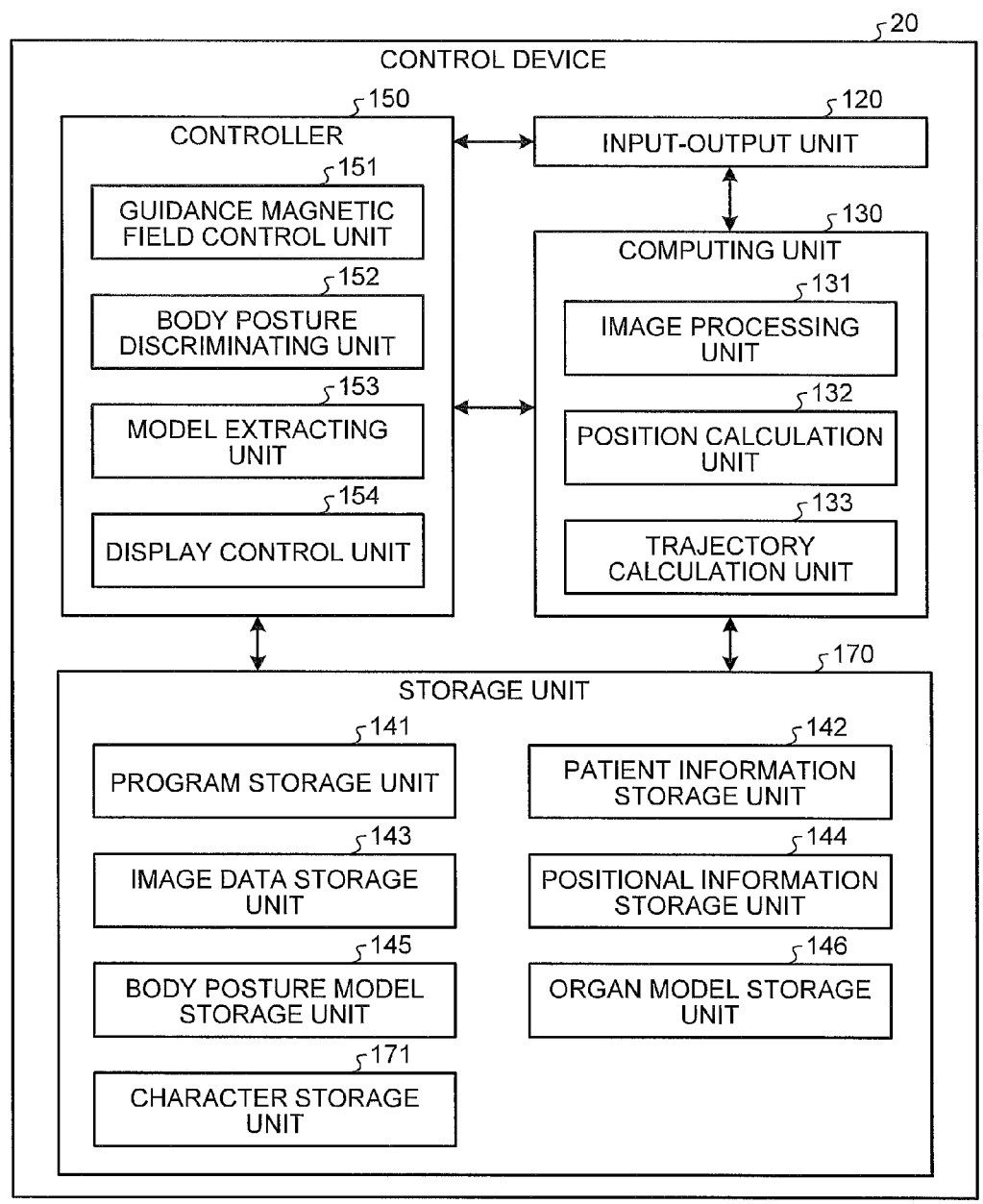
FIG. 18 is a block diagram illustrating a configuration of a control device included in a capsule endoscope system according to a third embodiment of the present invention.

FIG. 18 is a block diagram illustrating a configuration of a control device included in a capsule endoscope system according to the third embodiment of the present invention. A control device 20 illustrated in FIG. 18 includes a storage unit 170 in place of the storage unit 140 in comparison with the control device 17 illustrated in FIG. 6. Configurations of respective units of the control device 20 other than the storage unit 170 are similar to those in the first embodiment. Further, configurations of respective units of the capsule endoscope system other than the control device 20 are also similar to those in the first embodiment (see FIG. 1).

The storage unit 170 further includes a character storage unit 171 that stores image data of a schematic image of the capsule endoscope 10 (hereinafter, the schematic image is referred to as character), in comparison with the storage unit 140 illustrated in FIG. 6.

Figure 19:
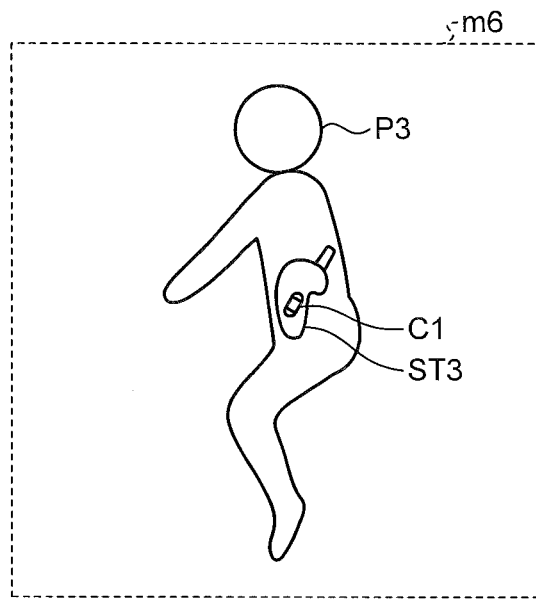
FIG. 19 is a schematic diagram illustrating a display example of body posture information in the third embodiment.

An operation of the capsule endoscope system according to the third embodiment is similar to that of the first embodiment (see FIG. 10) and the second embodiment (see FIG. 14) as a whole, and is different from the first and second embodiments in a display format of body posture information displayed in a body posture information display region m6 (see FIG. 9) in step S118 (see FIG. 10) or step S137 (see FIG. 14). That is, in the third embodiment, as illustrated in FIG. 19, a character C1 of the capsule endoscope 10 is superimposed on a body posture model or an organ model extracted by a model extracting unit 153, and the superimposed image is displayed. Note that FIG. 19 illustrates an example in which an organ model ST3 and the character C1 are superimposed on a body posture model P3 in decubitus left position.

To be specific, a display control unit 154 calculates coordinates on the body posture model (or the organ model) corresponding to a guidance target position of the capsule endoscope 10 based on operation instruction information input from an operation input device 16, and displays the character C1 on the calculated coordinates. The direction of the character C1 at this time is determined according to a guidance target posture of the capsule endoscope 10 based on the operation instruction information input from the operation input device 16.

As described above, the character C1 of the capsule endoscope 10 is superimposed on the body posture model and the organ model and the superimposed image is displayed, whereby a user can easily grasp a relative relationship between the position and an imaging direction of the capsule endoscope 10, and the body posture and the organ of the subject 2, and can easily estimate a body part being imaged by the capsule endoscope 10.

Modification 3-1

Next, a modification 3-1 of the third embodiment of the present invention will be described.

In the third embodiment, the display control unit 154 determines the coordinates and the direction in which the character C1 is displayed, based on the guidance instruction information input from the operation input device 16. However, the coordinates and the direction of the character C1 may be determined based on a position and a posture of a capsule endoscope 10 detected in step S111 of FIG. 10.

Modification 3-2

Next, a modification 3-2 of the third embodiment of the present invention will be described.

Figure 20:
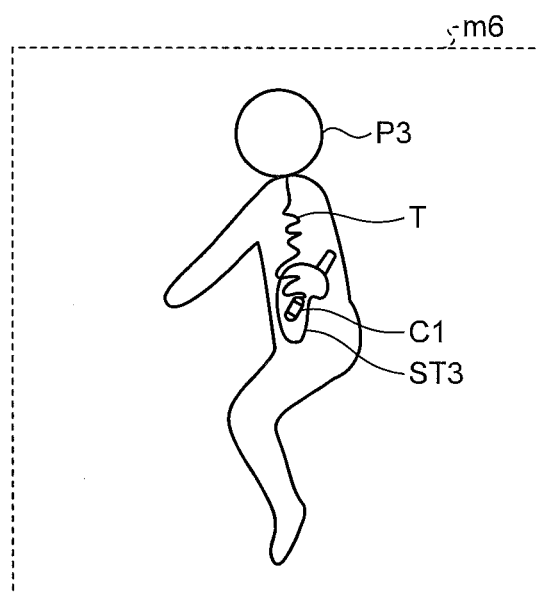
FIG. 20 is a schematic diagram illustrating a display example of body posture information in a modification 3-2.

FIG. 20 is a schematic diagram illustrating a display example of body posture information in the modification 3-2. As illustrated in FIG. 20, a trajectory T of a capsule endoscope 10 may be displayed in a body posture information display region m6 together with the body posture model or an organ model and a character C1. In this case, a display control unit 154 determines display coordinates of the trajectory T on the body posture model based on the trajectory calculated by a trajectory calculation unit 133. Note that FIG. 20 illustrates an example in which an organ model ST3, the character C1, and the trajectory T are superimposed on a body posture model P3 in decubitus left position.

Modification 3-3

Next, a modification 3-3 of the third embodiment of the present invention will be described.

Figure 21:
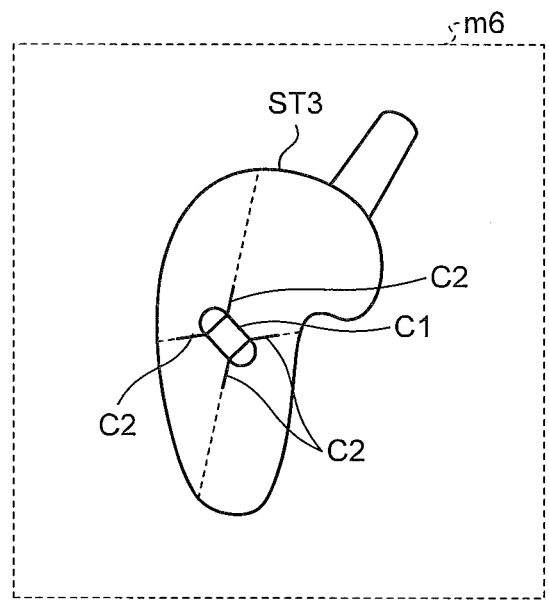
FIG. 21 is a schematic diagram illustrating a display example of body posture information in a modification 3-3.

FIG. 21 is a schematic diagram illustrating a display example of body posture information in the modification 3-3. As illustrated in FIG. 21, a mark C2 that expresses a viewing angle of a capsule endoscope 10 may be displayed in a body posture information display region m6. In this case, a display control unit 154 determines display coordinates of the mark C2 based on guidance target position and posture of the capsule endoscope 10 based on guidance instruction information input from an operation input device 16, and viewing angles of imaging units 102 and 103 included in the capsule endoscope 10. Alternatively, the display coordinates of the mark C2 may be determined based on a position and a posture of the capsule endoscope 10 calculated by a position calculation unit 132. According to the modification 3-3, a user can easily estimate a body part and a range being imaged by the capsule endoscope 10. Note that FIG. 21 illustrates an example in which a character C1 and the mark C2 are superimposed on an organ model ST3 in decubitus left position.

Modification 3-4

Next, a modification 3-4 of the third embodiment of the present invention will be described.

Figure 22:
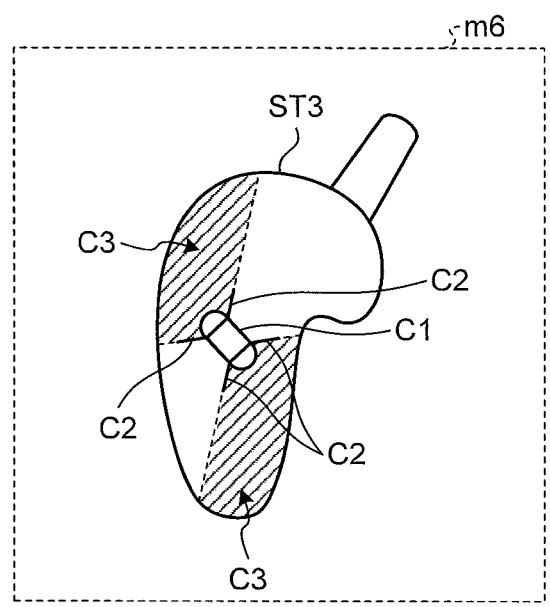
FIG. 22 is a schematic diagram illustrating a display example of body posture information in a modification 3-4.

FIG. 22 is a schematic diagram illustrating a display example of body posture information in the modification 3-4. As illustrated in FIG. 22, a region C3 corresponding to a region (imaging range) included in a viewing angle of a capsule endoscope 10 may be displayed in a different color from other regions, in an organ model ST3 displayed in a body posture information display region m6. Accordingly, a user can more easily estimate a body part and a range being imaged by the capsule endoscope 10. Note that FIG. 22 illustrates an example in which a character C1 and a mark C2 are superimposed on the organ model ST3 in decubitus left position, and illustrates the difference of the color of the region C3 by application of hatching.

Modification 3-5

Next, a modification 3-5 of the third embodiment of the present invention will be described.

A size of a character C1 superimposed on a body posture model or an organ model may be changed according to a region where a capsule endoscope 10 is guided or a position of the capsule endoscope 10 in a vertical direction. Note that the region where the capsule endoscope 10 is guided or the position of the capsule endoscope 10 in the vertical direction may be acquired from guidance instruction information input from an operation input device 16, or may be acquired from position information calculated by a position calculation unit 132.

Figure 23:
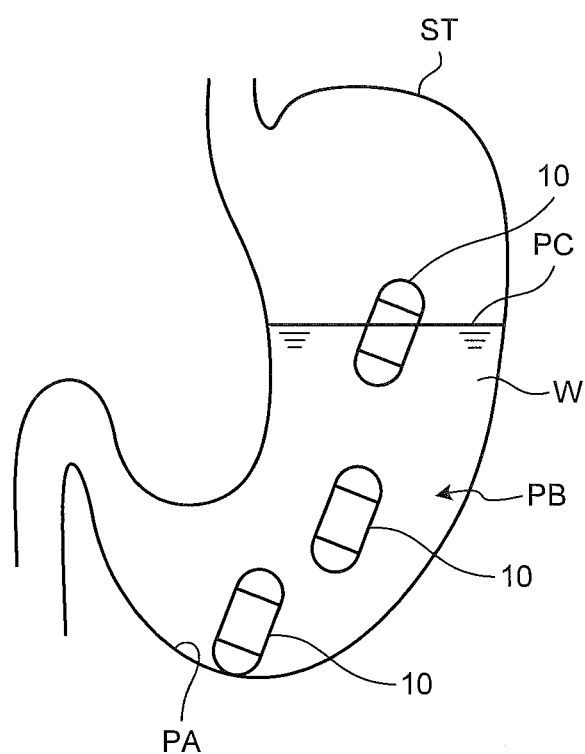
FIG. 23 is a schematic diagram illustrating a cross section of an organ (stomach) to be observed by a capsule endoscope.

FIG. 23 is a schematic diagram illustrating a cross section of an organ (stomach ST) to be observed by the capsule endoscope 10. Further, FIGS. 24A to 24C are schematic diagrams illustrating display examples of body posture information in the modification 3-5, and illustrates an example in which an organ model ST3 and the character C1 are superimposed on a body posture model P3 in decubitus left position.

Figure 24A:
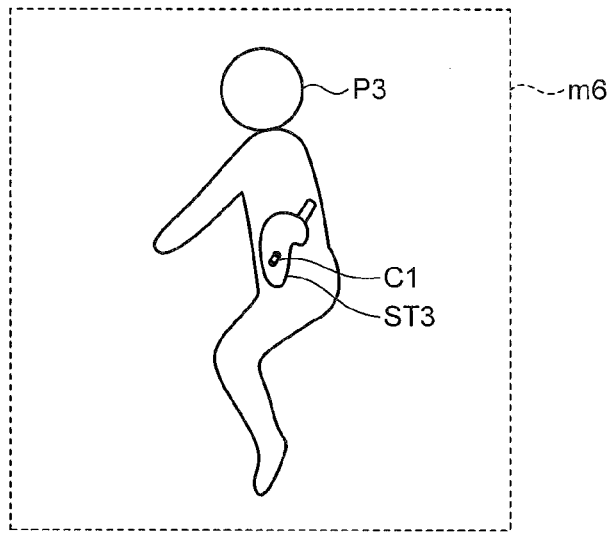
FIGS. 24A to 24C are schematic diagrams illustrating display examples of body posture information in a modification 3-5.
Figure 24B:
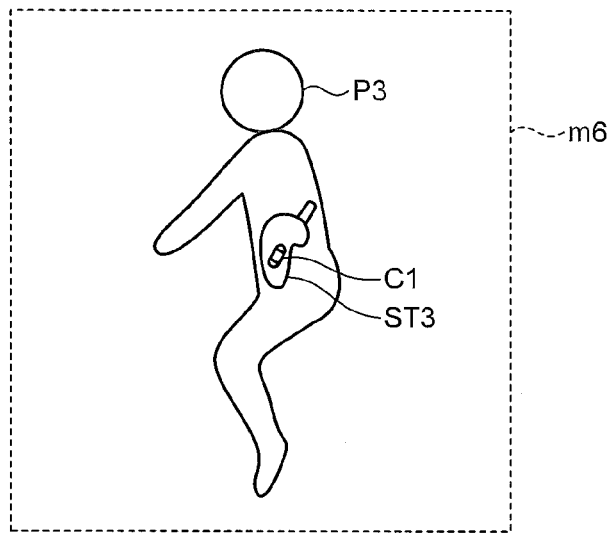
Figure 24C:
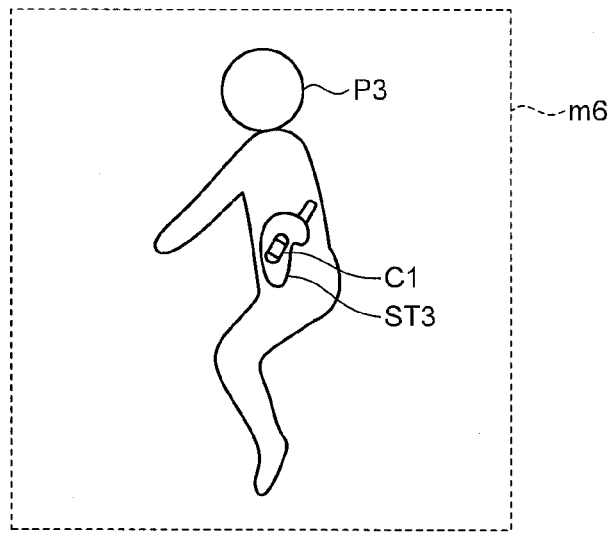

As illustrated in FIG. 23, when the capsule endoscope 10 is guided near a bottom (liquid bottom PA) of a liquid W introduced into a stomach ST, the character C1 is displayed in a smallest size, as illustrated in FIG. 24A. When the capsule endoscope 10 is guided in a liquid PB, as illustrated in FIG. 24B, the character C1 is displayed in a larger size than FIG. 24A. When the capsule endoscope 10 is guided near a liquid surface PC, the character C1 is displayed in a still larger size than FIG. 24B.

Alternatively, when the capsule endoscope 10 is located near the liquid bottom PA, the size of the character C1 may be minimized, and the size of the character C1 may be steplessly made larger as the position of the capsule endoscope 10 in the vertical direction becomes higher (closer to the liquid surface PC).

As described above, perspective is caused as the size of the character C1 is changed. Therefore, a user can intuitively grasp the position of the capsule endoscope 10 in the subject 2.

Note that, in the modification 3-5, the size of the body posture model or the organ model is made constant, and the size of the character C1 is changed. However, in contrast, the size of the character C1 may be constant and the size of the body posture model or the organ model may be changed. In this case, the size of the body posture model or the organ model is maximized when the capsule endoscope 10 is located near the liquid bottom PA of the liquid W, and the size of the body posture model or the organ model is made smaller as the capsule endoscope 10 gets closer to the liquid surface PC.

Modification 3-6

Next, a modification 3-6 of the third embodiment of the present invention will be described.

FIGS. 25A, 25B, 26A and 26B are schematic diagrams illustrating display examples of body posture information in the modification 3-6. In the above-described second embodiment, the display format of the body posture information in the body posture information display region m6 is changed according to ON/OFF of the guidance function. However, when a character C1 of a capsule endoscope 10 is displayed in a body posture information display region m6 like the third embodiment, a display format may be further changed according to whether the capsule endoscope 10 exists inside a guidance region R (see FIG. 1). Determination of whether the capsule endoscope 10 exists inside the guidance region R is performed by a controller 150 based on position information generated by a position calculation unit 132.

Figure 25A:
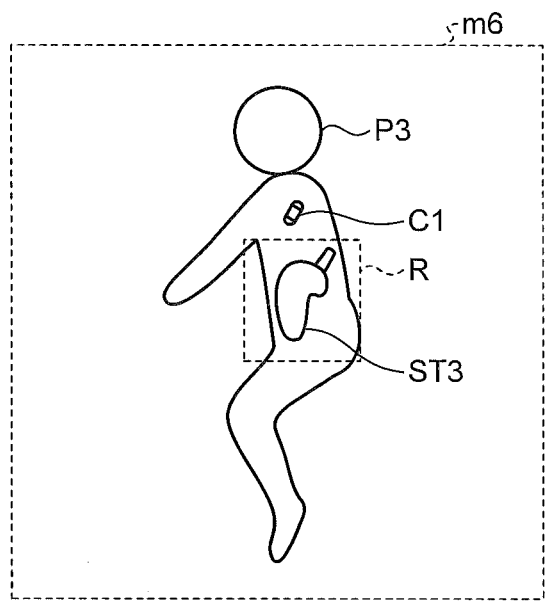
FIGS. 25A and 25B are schematic diagrams illustrating display examples of body posture information in a modification 3-6.
Figure 25B:
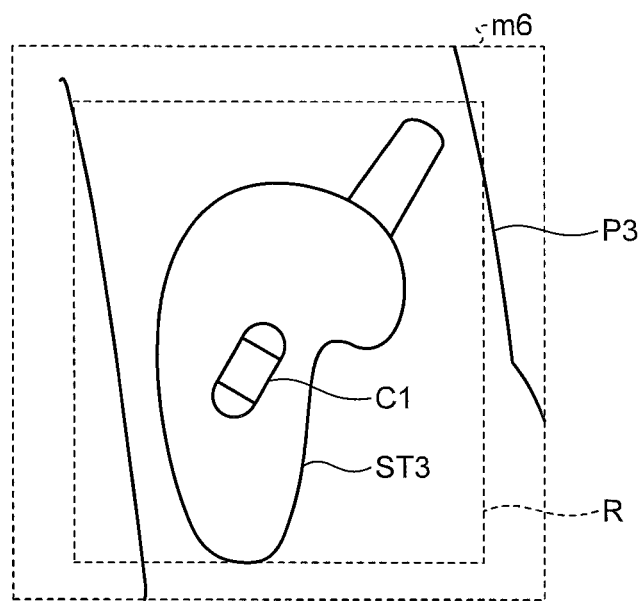

For example, when a guidance function is OFF, only a body posture model is displayed in the body posture information display region m6 regardless of the position of the capsule endoscope 10. Further, when the guidance function is ON and the capsule endoscope 10 exists outside the guidance region R, the entire body posture model (for example, a body posture model P3) is displayed, and an organ model (for example, an organ model ST3) and the character C1 are superimposed on the body posture model, and the superimposed image is displayed, as illustrated in FIG. 25A. Accordingly, the user can grasp a relative positional relationship between an entire subject 2 and the capsule endoscope 10. Meanwhile, when the guidance function is ON and the capsule endoscope 10 exists inside the guidance region R, the body posture model P3, the organ model ST3, and the character C1 are enlarged and displayed around a vicinity of the character C1, as illustrated in FIG. 25B. Accordingly, the user can recognize that guidance of the capsule endoscope 10 becomes available, and accurately grasp the relative positional relationship between the organ and the character C1, and an imaging direction, thereby to perform a guiding operation of the capsule endoscope 10.

Figure 26A:
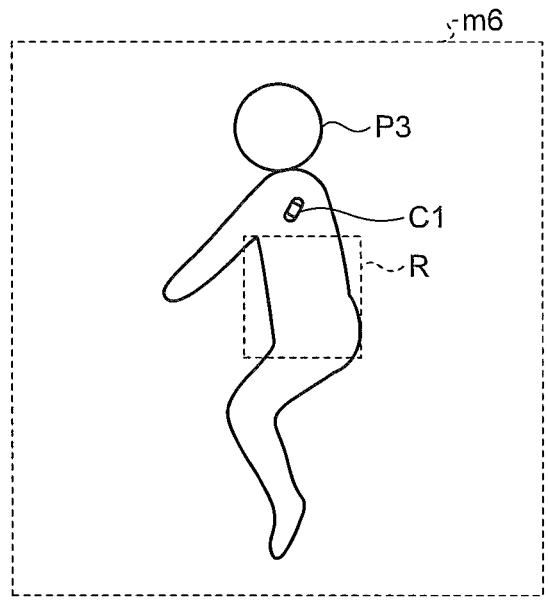
FIGS. 26A and 26B are schematic diagrams illustrating other display examples of the body posture information in the modification 3-6.
Figure 26B:
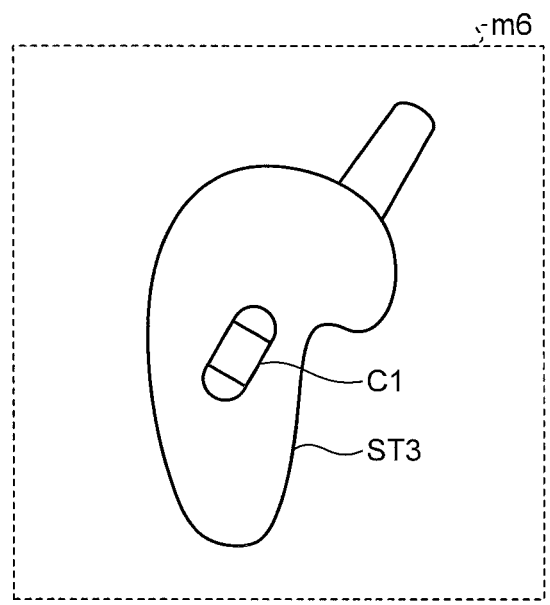

Alternatively, when the guidance function is ON and the capsule endoscope 10 is located outside the guidance region R, only the character C1 is superimposed on the body posture model (for example, the body posture model P3) and the superimposed image is displayed on the body posture information display region m6, as illustrated in FIG. 26A. Accordingly, the user can grasp the relative positional relationship between the entire subject 2 and the capsule endoscope 10. Meanwhile, when the guidance function is ON and the capsule endoscope 10 is located inside the guidance region R, the character C1 is superimposed on the organ model (for example, the organ model ST3), and the superimposed image is enlarged and displayed, as illustrated in FIG. 26B. Accordingly, the user can recognize that the guidance of the capsule endoscope 10 becomes available, and accurately grasp the relative positional relationship between the organ and the character C1 and the imaging direction, thereby to perform the guiding operation of the capsule endoscope 10.

Modification

Next, a modification of the first to third embodiments of the present invention will be described.

In the first to third embodiments, one set of the plurality of organ models according to the body posture of the subject 2 has been prepared. However, a plurality of sets of organ models having different sizes and shapes may be prepared. To be specific, a plurality of sets of organ models according to characteristics of patient such as sexes, ages, and physical constitutions is stored in an organ model storage unit 146 in advance.

In displaying an organ model in a body posture information display region m6, a display control unit 154 selects one set of organ models from the plurality of sets of organ models based on patient information, and extracts an organ model according to a body posture of a subject 2 from among the selected organ models.

Alternatively, a user may be able to select a desired set from among the plurality of sets of organ models stored in the organ model storage unit 146 in advance. Further, the user may be able to perform fine adjustment such as enlargement or reduction of organ models included in the set selected by the user.

According to the present modification, a relative size of the organ model to be superimposed is changed with respect to a body posture model and a character of a capsule endoscope 10. Therefore, the user can easily estimate a relative positional relationship between the capsule endoscope 10, and the subject 2 and the organ.

Further, in the first to third embodiments, the organ model extracted by the model extracting unit 153 is displayed in the body posture information display region m6 in a predetermined direction. However, as another modification, the organ model may be rotated and displayed according to a traveling direction of the capsule endoscope 10.

Fourth Embodiment

Next, a fourth embodiment of the present invention will be described.

Figure 27:
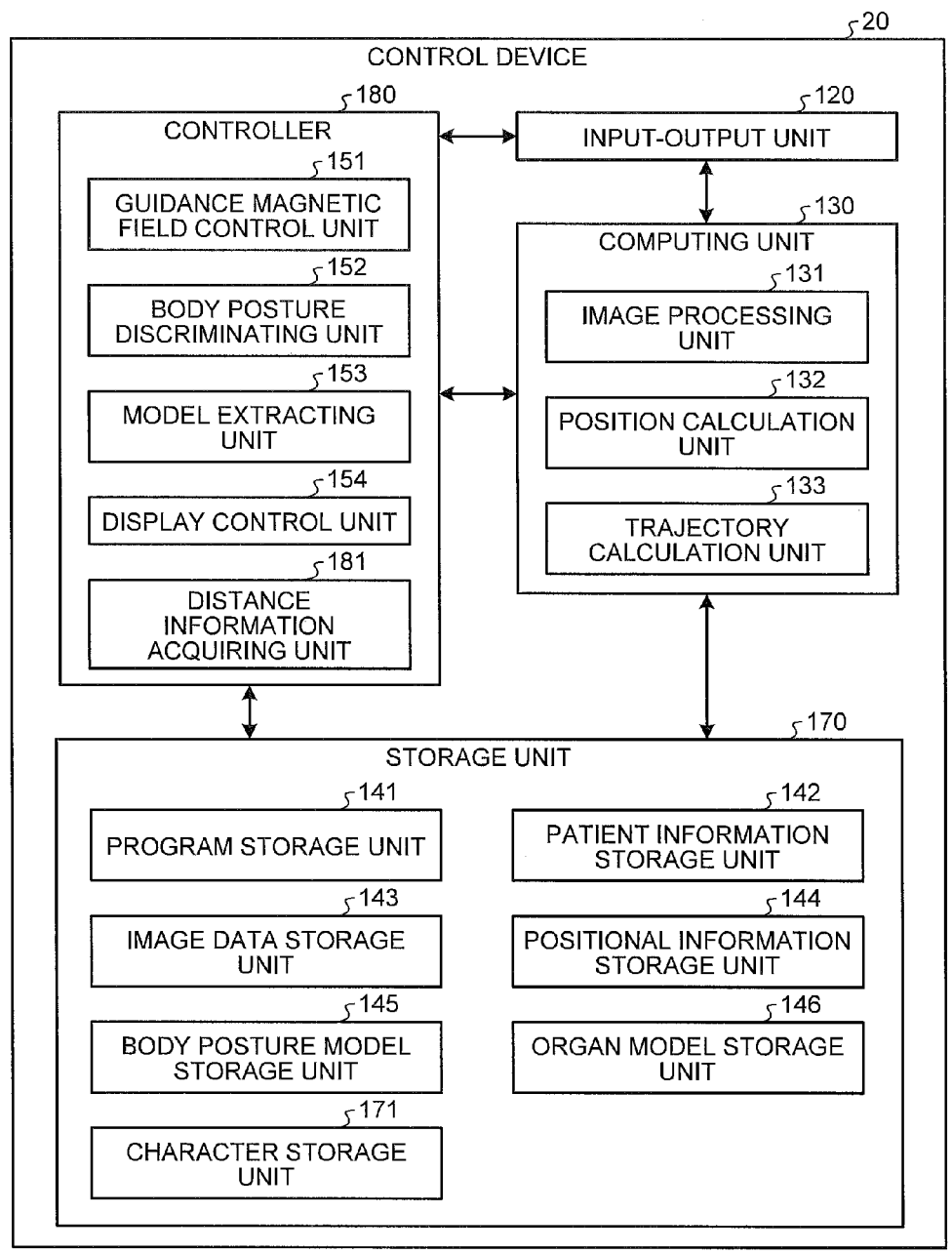
FIG. 27 is a block diagram illustrating a configuration of a control device included in a capsule endoscope system according to a fourth embodiment of the present invention.
Figure 28A:
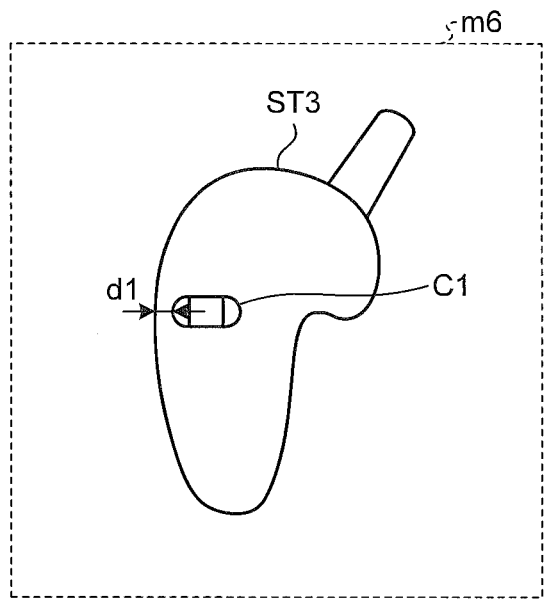
FIGS. 28A and 28B are schematic diagrams for describing a method of displaying body posture information in the fourth embodiment.
Figure 28B:
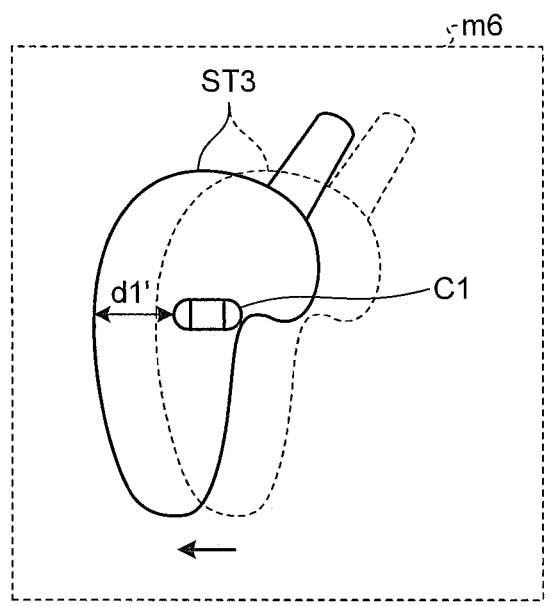

FIG. 27 is a block diagram illustrating a configuration of a control device included in a capsule endoscope system according to the fourth embodiment of the present invention. Further, FIGS. 28A and 28B are schematic diagrams for describing a method of displaying body posture information in the fourth embodiment.

A control device 30 illustrated in FIG. 27 includes a controller 180 in place of the controller 150 in comparison with the control device 20 illustrated in FIG. 18. Configurations of respective units of the control device 30 other than the controller 180 are similar to those in the third embodiment. Further, configurations of respective units of the capsule endoscope system other than the control device 20 are similar to those in the first embodiment (see FIG. 1).

The controller 180 further includes a distance information acquiring unit 181 that acquires a distance between a capsule endoscope 10 and an organ, in comparison with the controller 150 illustrated in FIG. 18. The distance information acquiring unit 181 acquires control information for controlling a light-emitting operation of an illuminating unit 114 included in the capsule endoscope 10, and acquires an actual distance between an organ in a subject 2 and imaging units 102 and 103 in an imaging optical axis, using the control information. That is, the fact that the distance to the organ and the length of an illumination emitting time are in a proportional relationship is used, and as the control information, light-emitting time information of the illuminating unit 114 is used. Alternatively, the distance between the capsule endoscope 10 and the organ may be calculated based on focusing information of the imaging units 102 and 103.

Note that, as a method of acquiring a distance between the capsule endoscope 10 and a wall of an organ, various known means are applicable, in addition to the above-described method. For example, a transmitting and receiving unit for ultrasonic waves or infrared rays is provided in the capsule endoscope 10, and transmission or reception timing data of the ultrasonic waves or the infrared rays by the transmitting and receiving unit is wirelessly transmitted together with image data, and the distance information acquiring unit 181 may calculate the distance between the capsule endoscope 10 and the wall of the organ based on the transmission or reception timing data received by a receiving device 15.

An operation of the capsule endoscope system according to the fourth embodiment is similar to that of the third embodiment as a whole, and is characterized in that a relative display position between a character and an organ model is adjusted according to the distance between the capsule endoscope 10 and the wall of the organ, in displaying the character of the capsule endoscope 10 in a body posture information display region m6 (see FIG. 9).

Here, display coordinates of the character superimposed on the organ model are calculated based on guiding operation information input from an operation input device 16 or position information calculated by a position calculation unit 132. However, there is a case where a relative positional relationship between the character and the organ model deviates with respect to an actual relative positional relationship between the capsule endoscope 10 and the organ, due to a guidance error or a position detection error. In the fourth embodiment, such deviation of the relative positional relationship can be corrected.

For example, as illustrated in FIG. 28A, when a distance d1 between a character C1 and an organ model ST3 is shorter than a distance d0 acquired by the distance information acquiring unit 181, a display control unit 154 shifts the organ model ST3 in a left direction in the drawing, and enlarges the distance between the organ model ST3 and the character C1. Alternatively, the display control unit 154 may shift the character C1 in a right direction in the drawing. Accordingly, as illustrated in FIG. 28B, a distance d1' between the character C1 and the organ model ST3 is caused to correspond to the distance d0 acquired by the distance information acquiring unit 181, and is set to the same distance as the distance d0.

As described above, according to the fourth embodiment, the relative display position between the character of the capsule endoscope 10 and the organ model is adjusted based on a measured value of the distance between the capsule endoscope 10 and the organ. Therefore, a user can more accurately grasp the relative positional relationship between the capsule endoscope 10 and the organ.

Modification 4

Next, a modification 4 of the fourth embodiment of the present invention will be described.

Figure 29A:
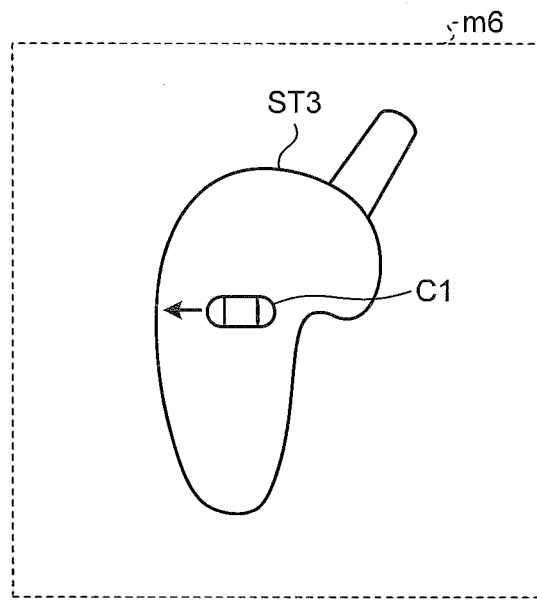
FIGS. 29A and 29B are schematic diagrams for describing a method of displaying body posture information in a modification 4.
Figure 29B:
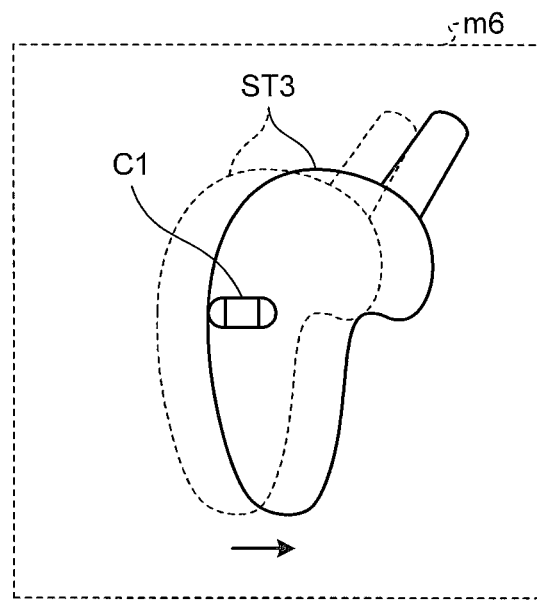

FIGS. 29A and 29B are schematic diagrams for describing a method of displaying body posture information in the modification 4. A relative display position between a character of a capsule endoscope 10 and an organ model may be adjusted based on a difference between an operation amount to an operation input device 16 and a displacement amount of the capsule endoscope 10.

For example, as illustrated in FIG. 29A, assume that a guiding operation to move the capsule endoscope 10 in a left direction in the drawing is performed using the operation input device 16 when a character C1 is displayed in a position separated from a wall surface of an organ model ST3. When a moving amount of the capsule endoscope 10 calculated by a position calculation unit 132 is smaller than a target moving amount of the capsule endoscope 10 corresponding to an operation amount to the operation input device 16, there is a possibility that the capsule endoscope 10 has already reached the inner wall of the organ in reality. In such a case, a display control unit 154 shifts the organ model ST3 in the right direction in the drawing until the organ model ST3 reaches the character C1, as illustrated in FIG. 29B. Alternatively, the display control unit 154 may shift the character C1 in a left direction in the drawing to reach the organ model ST3. Accordingly, the relative positional relationship between the character C1 and the organ model ST3 can accord with the actual relative positional relationship between the capsule endoscope 10 and the organ.

Fifth Embodiment

Next, a fifth embodiment of the present invention will be described.

Figure 30:
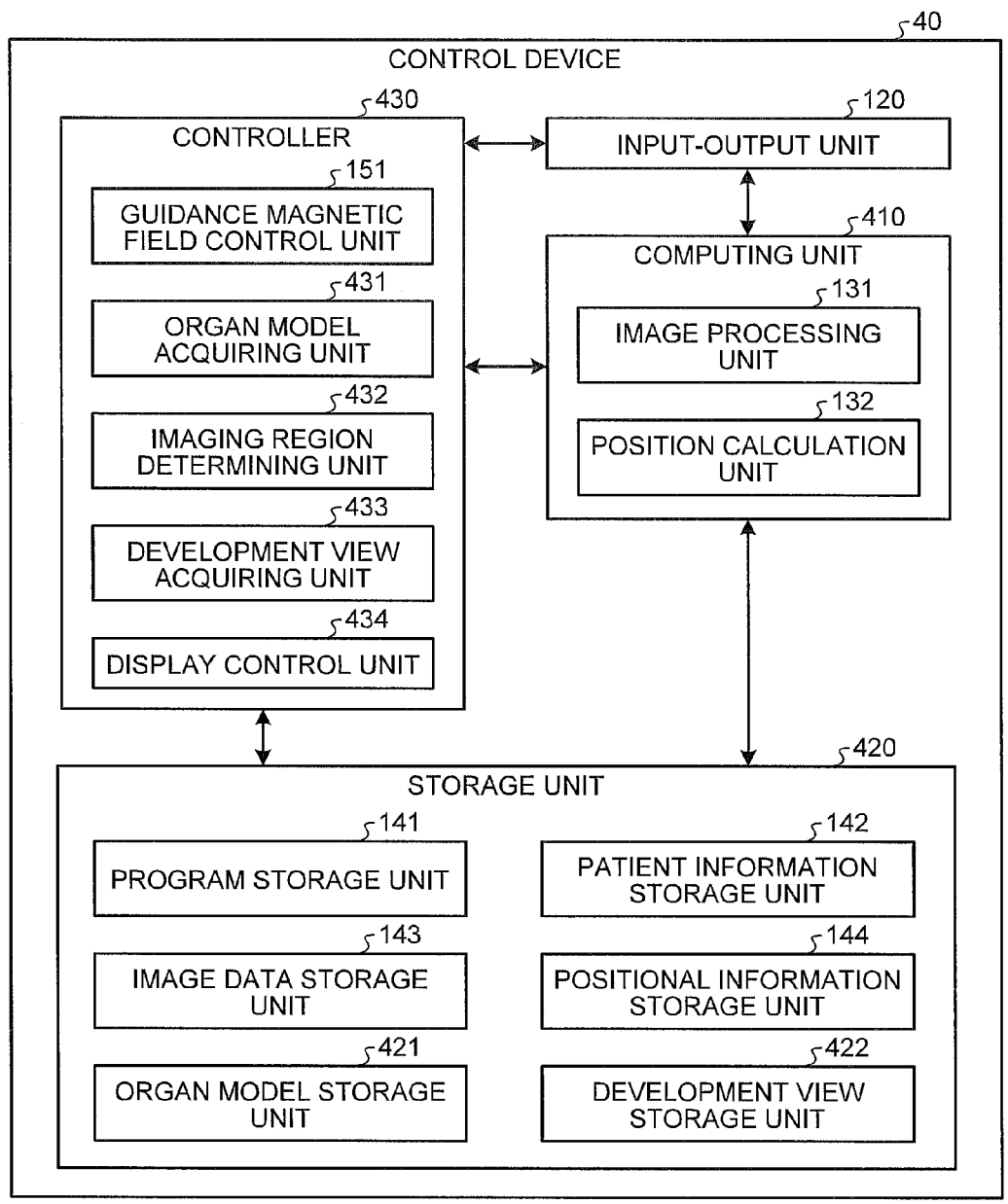
FIG. 30 is a block diagram illustrating a configuration example of a control device in a fifth embodiment of the present invention.
Figure 31:
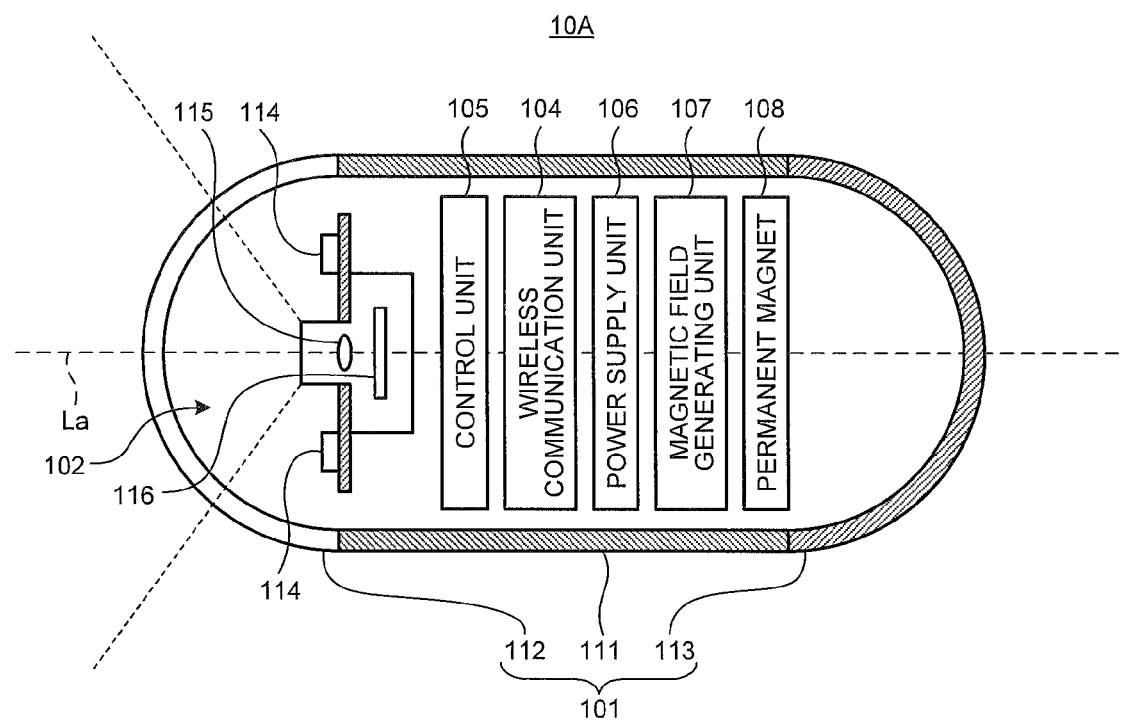
FIG. 31 is a schematic diagram illustrating an example of an internal structure of a capsule endoscope used in the fifth embodiment of the present invention.

FIG. 30 is a block diagram illustrating a configuration example of a control device included in a capsule endoscope system according to the fifth embodiment. A capsule endoscope system according to the fifth embodiment includes a control device 40 illustrated in FIG. 30, in place of the control device 17 illustrated in FIG. 1. Further, in the fifth embodiment, as illustrated in FIG. 31, a monocular capsule endoscope 10A from which one imaging unit 103 is omitted is used, in comparison with the capsule endoscope 10 illustrated in FIG. 2. Configurations and operations of respective units of the capsule endoscope system other than the capsule endoscope 10A and the control device 40 are similar to those in the first embodiment.

As illustrated in FIG. 30, the control device 40 according to the fifth embodiment includes an input-output unit 120, a computing unit 410, a storage unit 420, and a controller 430. Among them, a configuration and an operation of the input-output unit 120 is similar to those in the first embodiment (see FIG. 6).

The computing unit 410 includes an image processing unit 131 and a position calculation unit 132.
Configurations and operations of the image processing unit 131 and the position calculation unit 132 are similar to those in the first embodiment.

The storage unit 420 includes an organ model storage unit 421 and a development view storage unit 422, in place of the body posture model storage unit 145 and the organ model storage unit 146 illustrated in FIG. 6.

The organ model storage unit 421 stores three-dimensional data of a model of an organ (hereinafter, referred to as organ model), which is an imaging target of a capsule endoscope. In the fifth embodiment, the imaging target of the capsule endoscope is a stomach. Therefore, the organ model storage unit 421 stores a stomach model as the organ model. The stomach model stored in the organ model storage unit 421 is not limited to one type, and a plurality of stomach models having different shapes according to ages and sexes of subjects 2 may be stored. Stomach models having special shapes such as a cascade stomach and an hour-glass stomach may be stored, in addition to normal stomach models. Alternatively, stomach models may be created from images of stomach acquired in an X-ray examination, a CT examination, an MRI, or the like conducted for the subject 2, and stored in the organ model storage unit 421.

The development view storage unit 422 stores two-dimensional image data of a development view of a developed organ model stored in the organ model storage unit 421. When a plurality of types of organ models is stored in the organ model storage unit 421, the development view storage unit 422 may store development views corresponding to the organ models respectively. Further, a development view directly made from an image of stomach acquired in an X-ray examination, a CT examination, an MRI, or the like conducted for the subject 2 may be stored in the development view storage unit 422.

The controller 430 includes a guidance magnetic field control unit 151, an organ model acquiring unit 431 that acquires the organ model stored in the organ model storage unit 421, an imaging region determining unit 432 that determines a region in an organ (hereinafter, referred to as imaging region) imaged by an imaging unit 102 of the capsule endoscope, a development view acquiring unit 433 that acquires the development view of the organ model acquired by the organ model acquiring unit 431, and a display control unit 434 that controls a display operation in a display device 18. Among them, the operation of the guidance magnetic field control unit 151 is similar to that in the first embodiment.

The organ model acquiring unit 431 acquires the organ model stored in the organ model storage unit 421, and sets a direction of the organ model to a direction corresponding to a body posture of the subject 2. To be specific, the organ model acquiring unit 431 associates coordinates of points that configure a wall of the organ model and coordinates of a space region that includes the subject 2 based on the three-dimensional data of the organ model. Here, in performing an examination with the capsule endoscope 10A, the subject 2 takes a predetermined body posture according to an instruction of a user such as a doctor. At this time, the direction of the organ (for example, the stomach) of the subject 2 is changed according to the body posture of the subject 2. To be specific, when the subject 2 takes body postures in supine position, prone position, decubitus left position, and decubitus right position, on a bed 3, respectively, the stomach of the subject 2 faces directions as illustrated in FIGS. 8A to 8D. Note that FIGS. 8A to 8D illustrate states where the stomach ST of the subject 2 is projected on a horizontal plane (a placing surface of the bed 3).

Further, when a plurality of organ models is stored in the organ model storage unit 421, the organ model acquiring unit 431 selects and acquires the organ model corresponding to patient information (for example, an age or a sex) of the subject 2 stored in a patient information storage unit 142.

The imaging region determining unit 432 determines an imaging region based on a positional relationship between a position of a capsule endoscope 10A calculated by a position calculation unit 132 and the organ model acquired by an organ model acquiring unit 431, and a posture of the capsule endoscope 10A calculated by the position calculation unit 132.

The development view acquiring unit 433 acquires the development view stored in the development view storage unit 422, and sets a region on the development view corresponding to a region in the subject 2 (the organ) being currently imaged by the capsule endoscope 10A. Here, the coordinates of the points on the development view are associated with the three-dimensional coordinates of the points that configure a wall of the organ model in advance.

When a plurality of development views is stored in the development view storage unit 422, the development view acquiring unit 433 acquires the development view corresponding to the organ model acquired by the organ model acquiring unit 431.

The display control unit 434 displays an in-vivo image based on image data to which image processing has been applied by the image processing unit 131, the patient information, and related information such as the current imaging region in a display device 18 in a predetermined format in real time during the examination with the capsule endoscope 10A.

Figure 32:
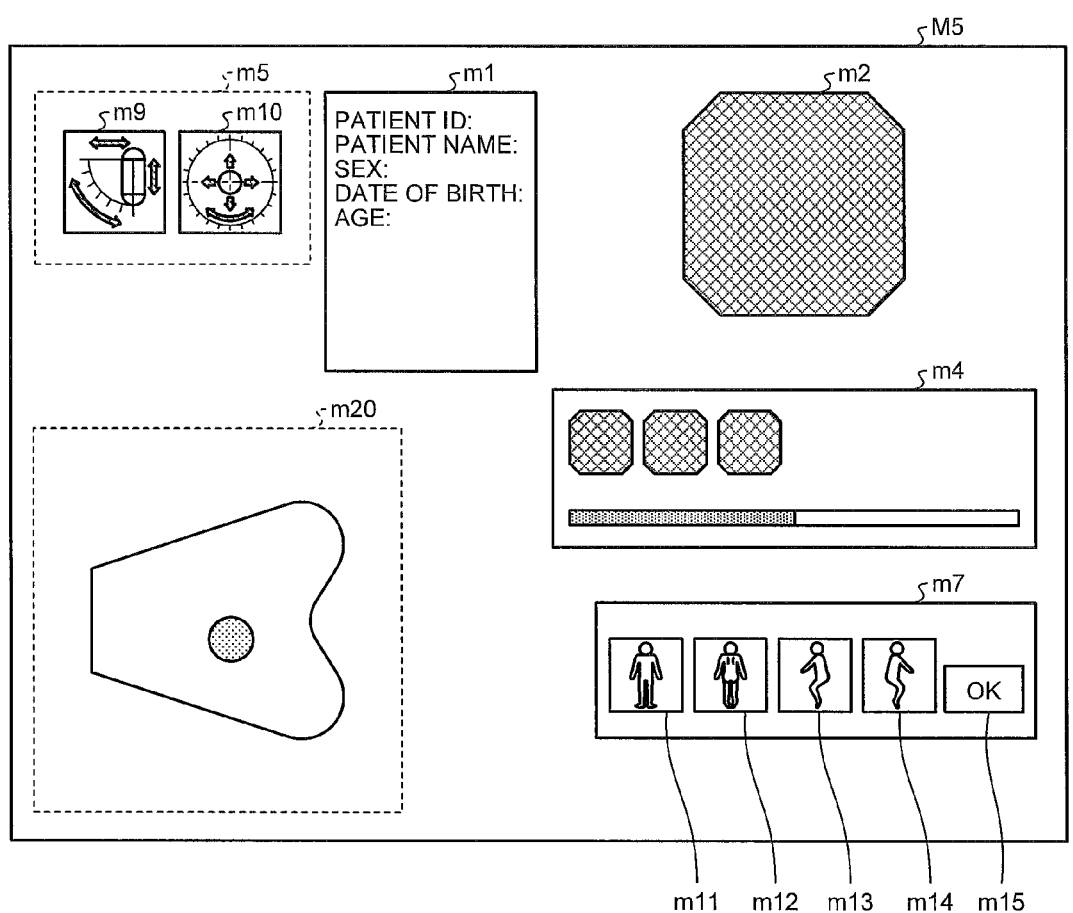
FIG. 32 is a schematic diagram illustrating an example of a screen on a display device.

FIG. 32 is a schematic diagram illustrating an example of a screen displayed on the display device 18 under control of the display control unit 434. As illustrated in FIG. 32, a screen M5 includes, similarly to the screen M1 illustrated in FIG. 9, a patient information display region m1 in which the patient information such as a patient ID, a patient name, a sex of the patient, a date of birth, and an age, an in-vivo image display region m2 that is a region in which the in-vivo image imaged by the imaging unit 102 is displayed, a captured image display region m4 in which the in-vivo image captured with a pressing operation to a capture button 16e is displayed, an operation information display region m5 in which operation information for the capsule endoscope 10A is displayed, and a body posture button display region m7 used to input the body posture of the subject 2. Further, an imaging region display region m20 in which the imaging region in the subject 2 is displayed is provided.

As described above, in the fifth embodiment, only one in-vivo image display region m2 is displayed on the screen M5 because the monocular capsule endoscope is used. Further, one image captured according to one pressing operation to the capture button 16e is displayed in the captured image display region m4. However, even in the fifth embodiment, a pantoscopic capsule endoscope 10 provided with imaging units 102 and 103 may be used, similarly to the first embodiment. In this case, an in-vivo image display region m3 is further provided on the screen M5, and two images captured according to one pressing operation to the capture button 16e are displayed in the captured image display region m4 (see FIG. 9).

Further, even in the fifth embodiment, a body posture information display region m6 (see FIG. 9) may be provided on the screen M5, similarly to the first embodiment.

Further, a special input button for allowing the user to select the body posture of the subject 2 may be provided in an operation input device 16, instead of providing the body posture button display region m7 on the screen M5.

The imaging region display region m20 is a region where the imaging region in the subject 2 imaged by the capsule endoscope 10A is displayed, that is, a region where a part of the body in the in-vivo image on the in-vivo image display region m2 is displayed. In the fifth embodiment, the imaging region is displayed on the development view of the organ (for example, the stomach) that is the imaging target of the capsule endoscope 10A.

The user operates the operation input device 16 while referring to such a screen M5, thereby to cause the capsule endoscope 10A to image a desired region in the subject 2.

Figure 33:
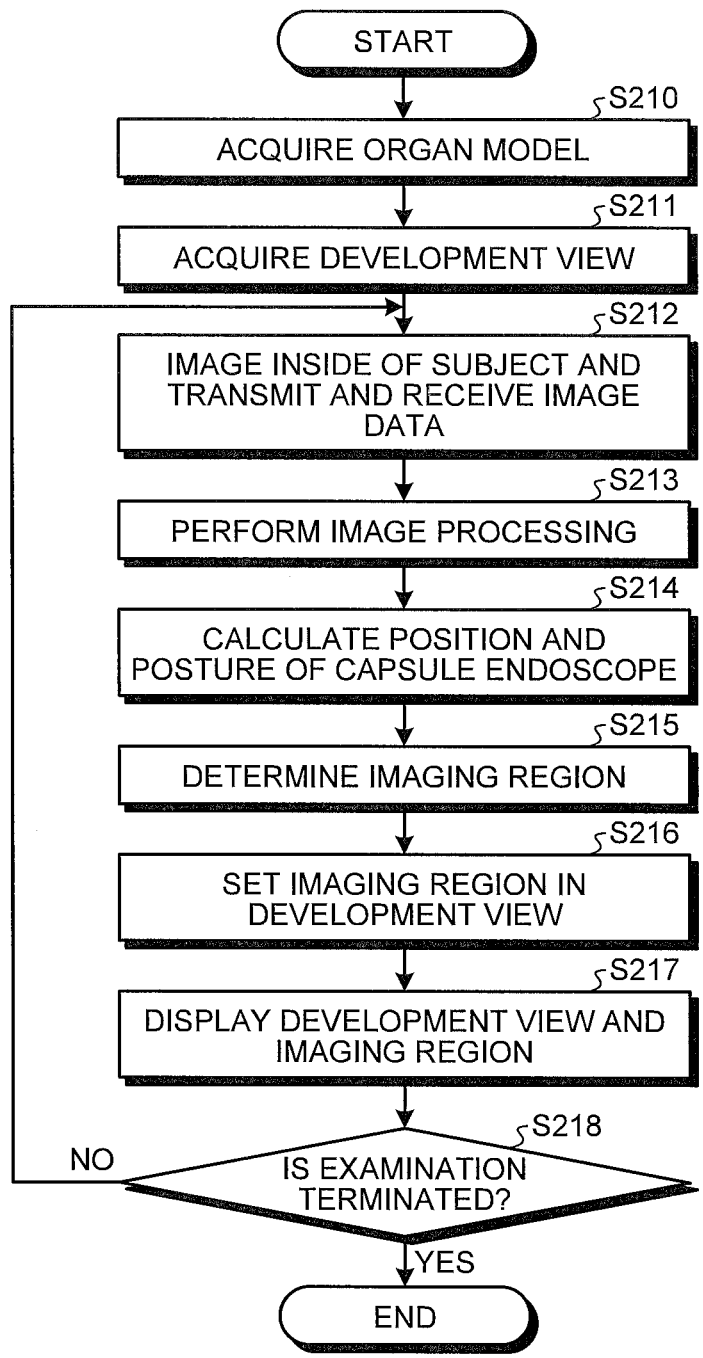
FIG. 33 is a flowchart illustrating a movement of the capsule endoscope system illustrated in FIG. 1.

Next, an operation of the capsule endoscope system 1 illustrated in FIG. 1 will be described with reference to FIG. 33. First, the user such as a doctor introduces a liquid W (see FIG. 3) into the subject 2 prior to an examination with the capsule endoscope 10A, and puts the subject 2 on the bed 3 in a predetermined body posture. Following that, the user selects any of icons m11 to m14 (see FIG. 32) displayed in the body posture button display region m7 using the operation input device 16 to input the body posture of the subject 2 to the control device 40. Then, the user turns ON a power supply of the capsule endoscope 10A, and inserts the capsule endoscope 10A into the subject 2.

In step S210, the organ model acquiring unit 431 acquires the organ model from the organ model storage unit 421, and sets the direction of the organ model to the direction corresponding to the body posture of the subject 2. To be specific, the organ model acquiring unit 431 discriminates the current body posture of the subject 2 based on a body posture selection signal input to the controller 430 by selection of any of the icons m11 to m14. Then, the organ model acquiring unit 431 associates the coordinates of the points that configure the wall of the organ model with the coordinates in the three-dimensional space according to the body posture of the subject 2.

In following step S211, the development view acquiring unit 433 acquires the development view of the organ model from the development view storage unit 422.

In following step S212, the capsule endoscope 10A wirelessly transmits the image data acquired by imaging an inside of the subject 2. In response to that, a receiving device 15 receives the image data wirelessly transmitted from the capsule endoscope 10A.

In step S213, the image processing unit 131 of the control device 40 generates the in-vivo image by applying predetermined image processing to the image data taken in from the receiving device 15. Note that image data for display that indicates the in-vivo image is sequentially stored in the image data storage unit 143.

In step S214, the position calculation unit 132 calculates a position and a posture of the capsule endoscope 10A. To be specific, a position detection device 11 detects an alternating magnetic field generated by a magnetic field generating unit 107 of the capsule endoscope 10A, and a signal processing device 13 applies predetermined signal processing to a detection signal of the alternating magnetic field to generate a digital position detection signal (position detection data). The position calculation unit 132 takes in the position detection data, calculates the position and the posture of the capsule endoscope 10A of that time, and stores the position and the posture in a position information storage unit 144 as position information.

Figure 34:
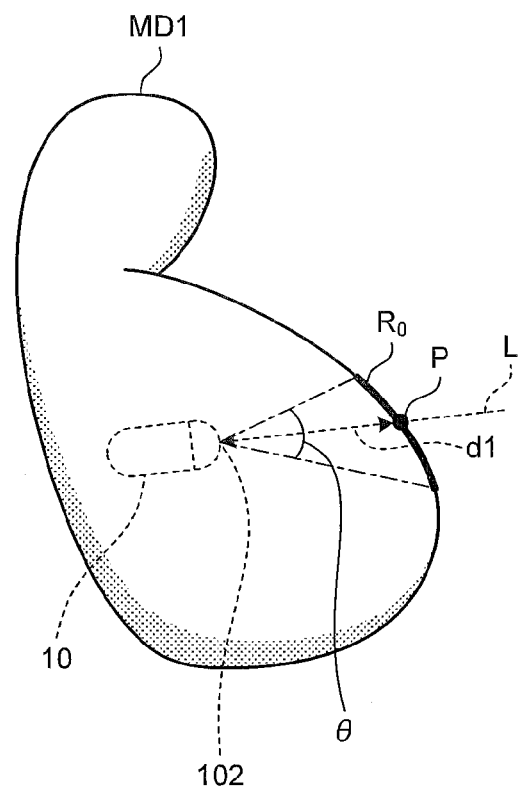
FIG. 34 is a schematic diagram for describing a method of determining an imaging region.

In step S215, the imaging region determining unit 432 determines the current imaging region by the capsule endoscope 10A. To be specific, as illustrated in FIG. 34, first, the imaging region determining unit 432 calculates the position and an imaging direction (a direction of an imaging optical axis L) of the imaging unit 102 from the position and the posture of the capsule endoscope 10A calculated in step S214. Following that, the imaging region determining unit 432 regards an organ model MD1 as the organ in the subject 2, and obtains coordinates of an intersection point P of the imaging optical axis L of the imaging unit 102 and a wall of the organ model MD1. Then, the imaging region determining unit 432 calculates a distance d1 from the imaging unit 102 to the intersection point P in a direction along the imaging optical axis L, and calculates an imaging region $R_0$ based on the distance d1 and a viewing angle θ of the imaging unit 102.

Figure 35:
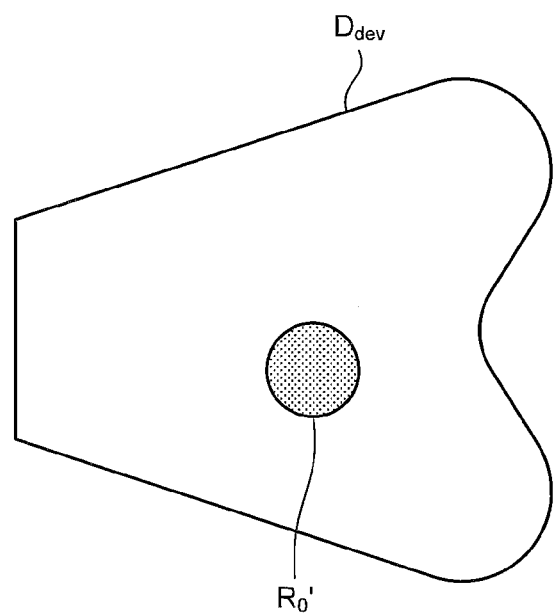
FIG. 35 is a schematic diagram illustrating an example of setting an imaging region on a development view of an organ model.

In step S216, the development view acquiring unit 433 acquires the development view of the organ model, and sets the imaging region in the development view. To be specific, a region $R_0'$ (see FIG. 35) on a development view $D_{dev}$ corresponding to the imaging region $R_0$ determined for the organ model MD1 (see FIG. 34) is set as the imaging region.

In step S217, the display control unit 434 causes the display device 18 to display the screen that includes the development view of the organ model and the imaging region. For example, the display device 18 displays the in-vivo image generated in step S213 in the in-vivo image display region m2 (see FIG. 32) under control of the display control unit 434, and displays the development view $D_{dev}$ acquired in step S211 in the imaging region display region m20 (see FIG. 32). Then, the display device 18 reduces the in-vivo image being displayed in the in-vivo image display region m2, that is, the image of the current imaging region in the subject 2, in accordance with the size of a region $R_0'$ on the development view $D_{dev}$, and superimposes the image on the region $R_0'$ and displays the superimposed image.

In step S218, the controller 430 determines whether to terminate the examination with the capsule endoscope 10A. When there is an operation input to terminate the examination by the user, or when the input of the image data from the receiving device 15 is stopped (that is, the wireless transmission of the image data from the capsule endoscope 10A is stopped), the controller 430 determines to terminate the examination (Yes in step S218). In this case, the operation of the capsule endoscope system is terminated.

When the examination with the capsule endoscope 10A is not terminated (No in step S218), the operation of the capsule endoscope system is returned to step S212.

As described above, according to the fifth embodiment, the imaging region is determined based on the positional relationship between the capsule endoscope 10A and the organ model, and the posture of the capsule endoscope 10A, and the in-vivo image is superimposed on the imaging region set on the development view of the organ and the superimposed image is displayed. Therefore, the user can accurately grasp the current imaging region by the capsule endoscope 10A in real time.

Modification 5-1

Next, a modification 5-1 of the fifth embodiment of the present invention will be described.

In the fifth embodiment, the development view acquiring unit 433 acquires the development view stored in the development view storage unit 422 in advance. However, the organ model acquiring unit 431 may directly create the development view from the organ model acquired from the organ model storage unit 421. In this case, even if the organ model storage unit 421 stores a plurality of organ models having different shapes and sizes, it is not necessary to prepare the development views corresponding to the respective organ models in advance.

Modification 5-2

Next, a modification 5-2 of the fifth embodiment of the present invention will be described.

Figure 36:
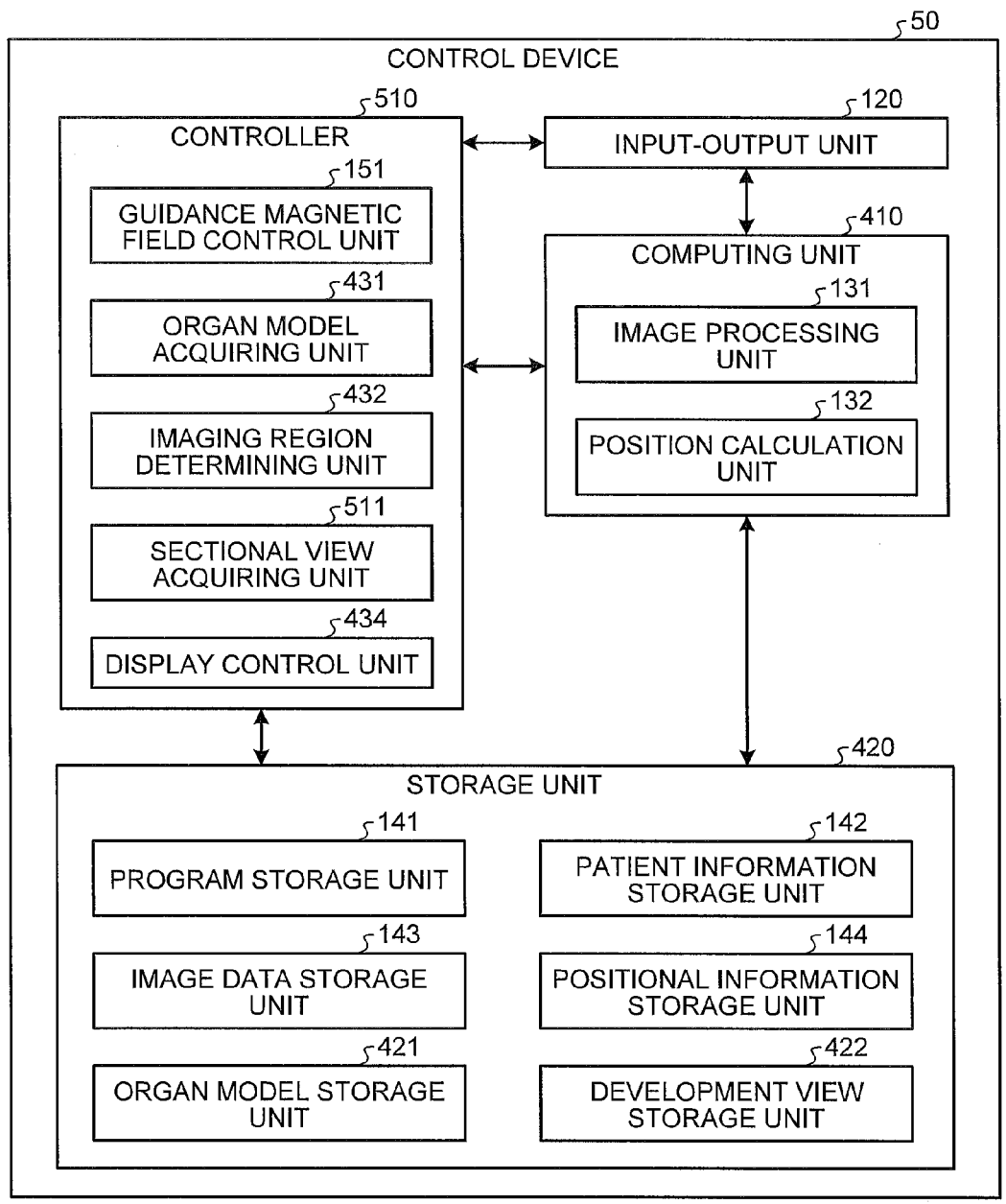
FIG. 36 is a block diagram illustrating a configuration example of a control device included in a capsule endoscope system according to a modification 5-2 of the fifth embodiment of the present invention.

FIG. 36 is a block diagram illustrating a configuration example of a control device included in a capsule endoscope system according to the modification 5-2 of the fifth embodiment. A control device 50 illustrated in FIG. 36 includes a controller 510 in place of the controller 430 in comparison with the control device 40 illustrated in FIG. 30. Configurations of respective units of the control device 50 other than the controller 510 are similar to those in the fifth embodiment. Further, configurations of respective units of the capsule endoscope system other than the control device 50 are also similar to those in the fifth embodiment (see FIGS. 1 and 31).

The controller 510 includes a sectional view acquiring unit 511, in place of the development view acquiring unit 433 illustrated in FIG. 30. The sectional view acquiring unit 511 creates a sectional view of the organ model acquired by the organ model acquiring unit 431, the sectional view being cut in a specific plane, and sets the imaging region to the sectional view. The plane in which the organ model is cut is not especially limited. When the organ model is a stomach model, for example, the stomach model is favorably cut in a plane that passes through a cardia and a pylorus and equally divides the stomach model. The stomach model is more favorably cut in a plane perpendicular to or parallel to the imaging direction of the capsule endoscope 10A. In this case, the sectional view created by the sectional view acquiring unit 511 is displayed in the imaging region display region m20 illustrated in FIG. 32.

Figure 37:
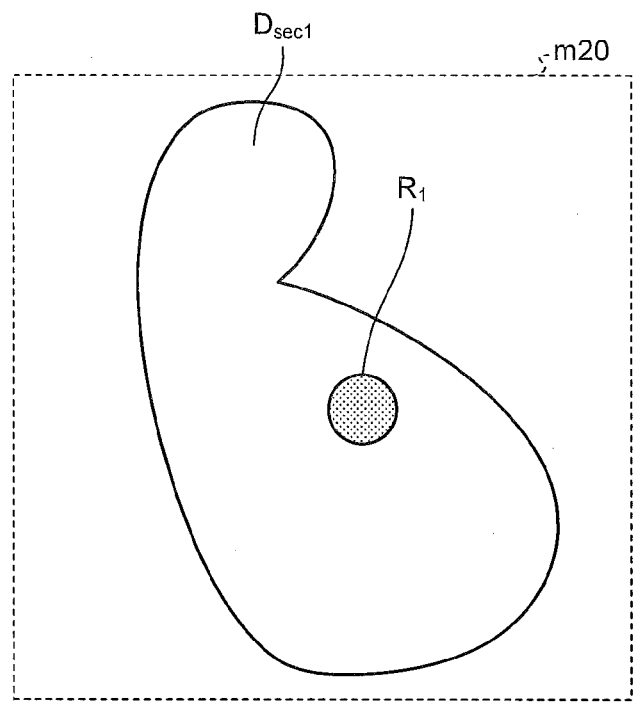
FIG. 37 is a schematic diagram illustrating an example of superimposing an imaging region on a cut surface of the organ model by a plane perpendicular to an imaging direction.

FIG. 37 is a schematic diagram illustrating an example of a sectional view of the organ model cut in a plane perpendicular to the imaging direction of the capsule endoscope 10A. When the cut surface is a sectional view $D_{sec1}$ perpendicular to the imaging direction, a reduced in-vivo image is superimposed and displayed on an imaging region $R_1$ set on the sectional view $D_{sec1}$.

Figure 38:
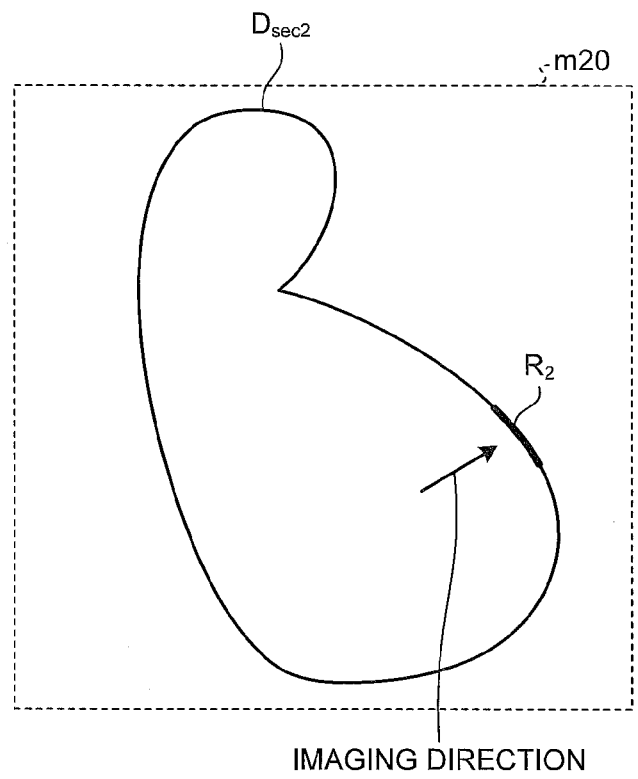
FIG. 38 is a schematic diagram illustrating an example of superimposing an imaging region on a cut surface of the organ model by a plane parallel to the imaging direction.

FIG. 38 is a schematic diagram illustrating an example of a sectional view of the organ model cut in a plane parallel to the imaging direction of the capsule endoscope 10A. When the cut surface is a sectional view $D_{sec2}$ parallel to the imaging direction, an imaging region $R_2$ set on the sectional view $D_{sec2}$ is filled with a specific color, or is provided with a pattern such as slant lines and displayed. Further, the imaging direction of the capsule endoscope 10A may be indicated by an arrow or the like.

Sixth Embodiment

Next, a sixth embodiment of the present invention will be described.

Figure 39:
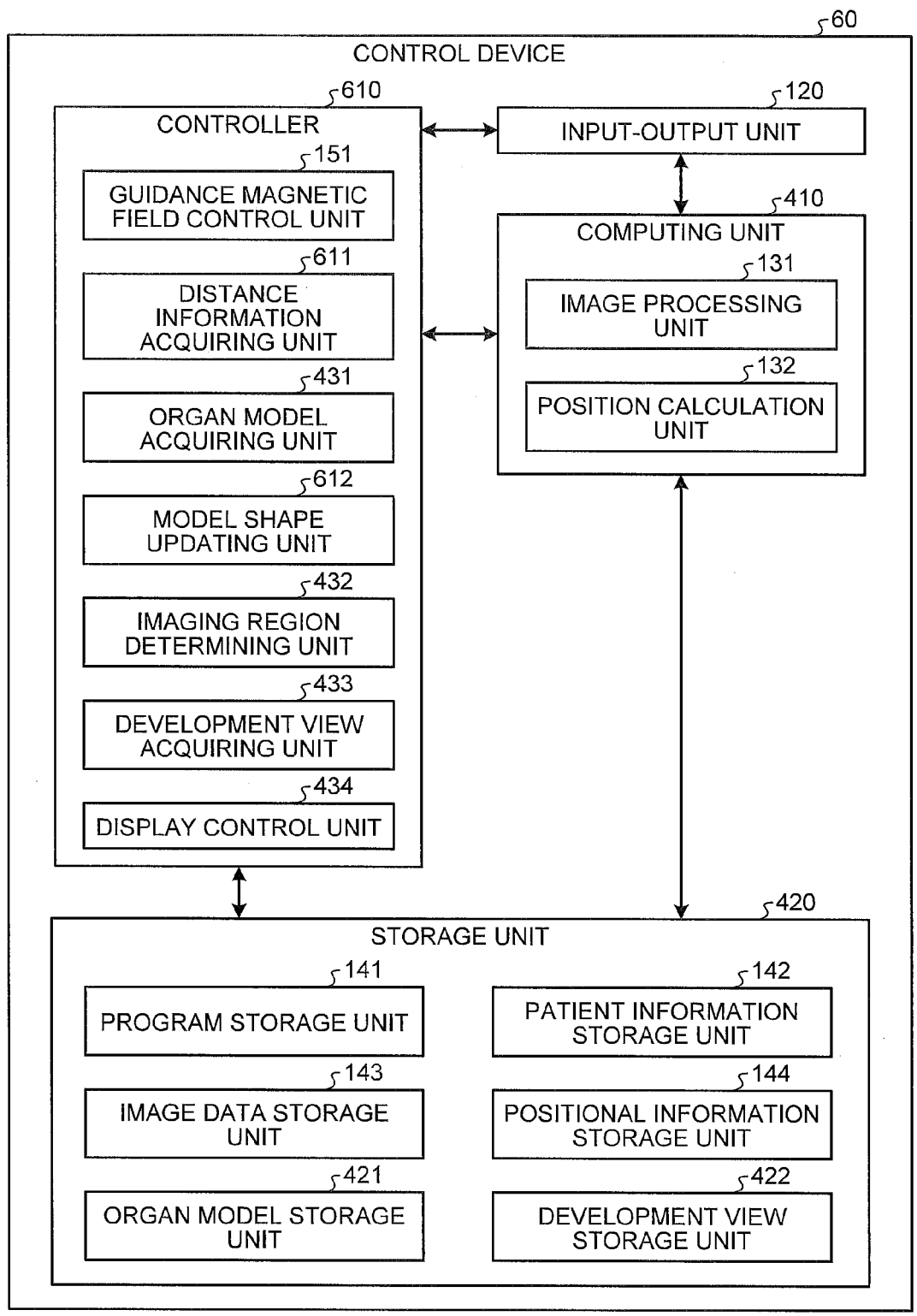
FIG. 39 is a block diagram illustrating a configuration example of a control device included in a capsule endoscope system according to a sixth embodiment of the present invention.

FIG. 39 is a block diagram illustrating a configuration example of a control device included in a capsule endoscope system according to the sixth embodiment. A control device 60 illustrated in FIG. 39 includes a controller 610 in place of the controller 430 in comparison with the control device 40 illustrated in FIG. 30. Configurations of respective units of the control device 60 other than the controller 610 are similar to those in the fifth embodiment. Further, configurations of respective units of the capsule endoscope system other than the control device 60 are also similar to those in the fifth embodiment (see FIGS. 1 and 31).

The controller 610 further includes a distance information acquiring unit 611 and a model shape updating unit 612, in comparison with the controller 430 illustrated in FIG. 30.

The distance information acquiring unit 611 acquires an actual distance between an organ in a subject 2 and an imaging unit 102. To be specific, the distance information acquiring unit 611 acquires control information that controls a light-emitting operation of an illuminating unit 114 included in a capsule endoscope 10A, and calculates a distance between the organ and the imaging unit 102 using the control information. That is, the fact that the distance to the organ and the length of an illumination emitting time are in a proportional relationship is used. As the control information, light-emitting time information of the illuminating unit 114 is used.

The model shape updating unit 612 updates a shape parameter of an organ model based on the distance acquired by the distance information acquiring unit 611.

Here, the shape of the organ model stored in the organ model storage unit 421 is determined in advance. However, there is a personal difference in the shape of the actual organ in the subject 2. Therefore, in the sixth embodiment, the distance between the capsule endoscope 10A and the organ in the subject 2 is acquired, and the shape of the organ model is updated based on the acquired value.

Next, an operation of the capsule endoscope system according to the sixth embodiment will be described with reference to FIG. 40. Note that steps S210 and S211 illustrated in FIG. 40 are similar to those in the fifth embodiment.

In step S220 following step S211, the capsule endoscope 10A wirelessly transmits the control information for controlling the operation of the illuminating unit 114 together with the image data acquired by imaging an inside of the subject 2. In response to that, a receiving device 15 receives the image data and the control information wirelessly transmitted from the capsule endoscope 10A.

Following steps S213 and S214 are similar to those in the fifth embodiment.

In step S221 following step S214, the distance information acquiring unit 611 acquires the distance between the imaging unit 102 of the capsule endoscope 10A and the organ based on the control information taken in from the receiving device 15, that is, the light-emitting time information.

Figure 41A:
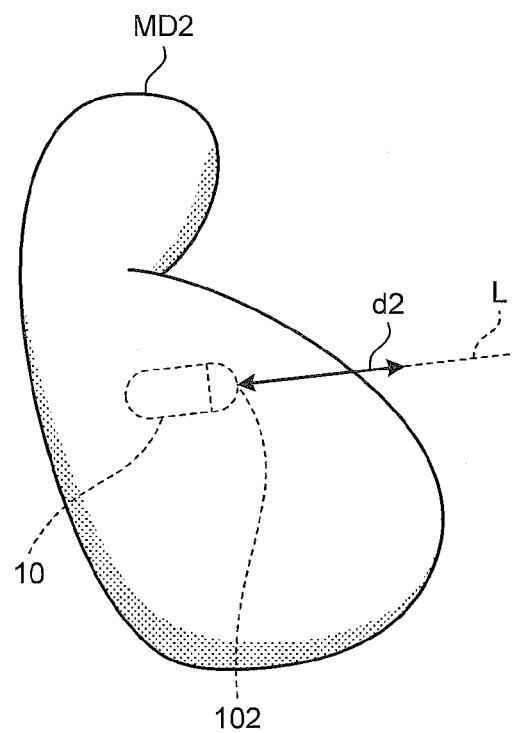
FIGS. 41A and 41B are schematic diagrams for describing a method of updating a shape parameter of an organ model in the sixth embodiment of the present invention.
Figure 41B:
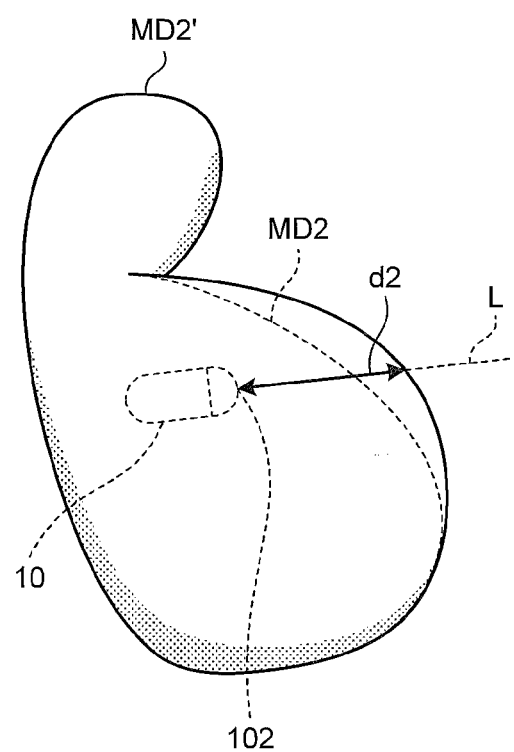

In step S222, the model shape updating unit 612 updates the shape parameter of the organ model based on the distance acquired in step S221. For example, as illustrated in FIG. 41A, assume that the positional relationship between the imaging unit 102 and an organ model MD2 is determined based on a position and a posture of the capsule endoscope 10A calculated in step S214. When an actual distance d2 between the imaging unit 102 and a wall of the organ acquired in step S221 is deviated from the distance between the imaging unit 102 and the wall of the organ model MD2, the model shape updating unit 612 causes the position of the wall of the organ model MD2 in an imaging direction L to conform to the distance d2, and updates the shape parameter such that surroundings of the position of the wall become continuous, as illustrated in FIG. 41B. Note that FIG. 41A indicates a case in which the distance d2 goes beyond the wall of the organ model MD2. In this case, as illustrated in FIG. 41B, the position of the wall of the organ model MD2 in the imaging direction is shifted in a right direction in the drawing. Accordingly, an updated organ model MD2' is created.

In step S223, the development view acquiring unit 433 re-acquires the development view of the organ model based on the updated shape parameter. For example, in the case of FIG. 41B, the development view corresponding to the updated organ model MD2' is created.

Following steps S215 to S218 are similar to those in the fifth embodiment.

As described above, in the sixth embodiment, the distance between the capsule endoscope 10A and the organ in the subject 2 is acquired, and the shape parameter of the organ model is updated based on the acquired value. Therefore, even if the shape of the organ stored in the organ model storage unit 421 in advance is different from the shape of the organ of the subject 2, the shape of the organ model gradually gets closer to the shape of the organ of the subject 2 while continuing to perform imaging with the capsule endoscope 10A. Therefore, the imaging region is determined for the updated organ model, and the imaging region is displayed on the development view of the updated organ model, whereby the user can more accurately grasp the current imaging region by the capsule endoscope 10A.

Modification 6-1

Next, a modification 6-1 of the sixth embodiment of the present invention will be described.

A method of acquiring a distance between a capsule endoscope 10A and an organ of a subject 2 is not limited to a method of calculating the distance based on an emitting time of an illuminating unit 114. For example, the distance may be calculated based on focusing information of an imaging unit 102, or the distance may be calculated based on a light-emitting amount (intensity) of the illuminating unit 114.

Alternatively, a distance measuring unit using ultrasonic waves or infrared rays may be further provided in the capsule endoscope 10A. In this case, a distance measurement result by the distance measuring unit is wirelessly transmitted together with image data, and a shape parameter of an organ model is updated in a control device 60 based on the distance measurement result received through a receiving device 15.

Further, characteristic points of a cardia are extracted from an acquired in-vivo image, and the shape parameter of the organ model may be updated based on position information of the in-vivo image including these characteristic points.

Further, an organ model of a stomach is created from an image of stomach acquired in an X-ray examination, a CT examination, an MRI, or the like conducted for the subject 2, and a development view and a sectional view to be displayed in an imaging region display region m20 (see FIG. 32) may be created based on the organ model.

Modification 6-2

Next, a modification 6-2 of the sixth embodiment of the present invention will be described.

Figure 42:
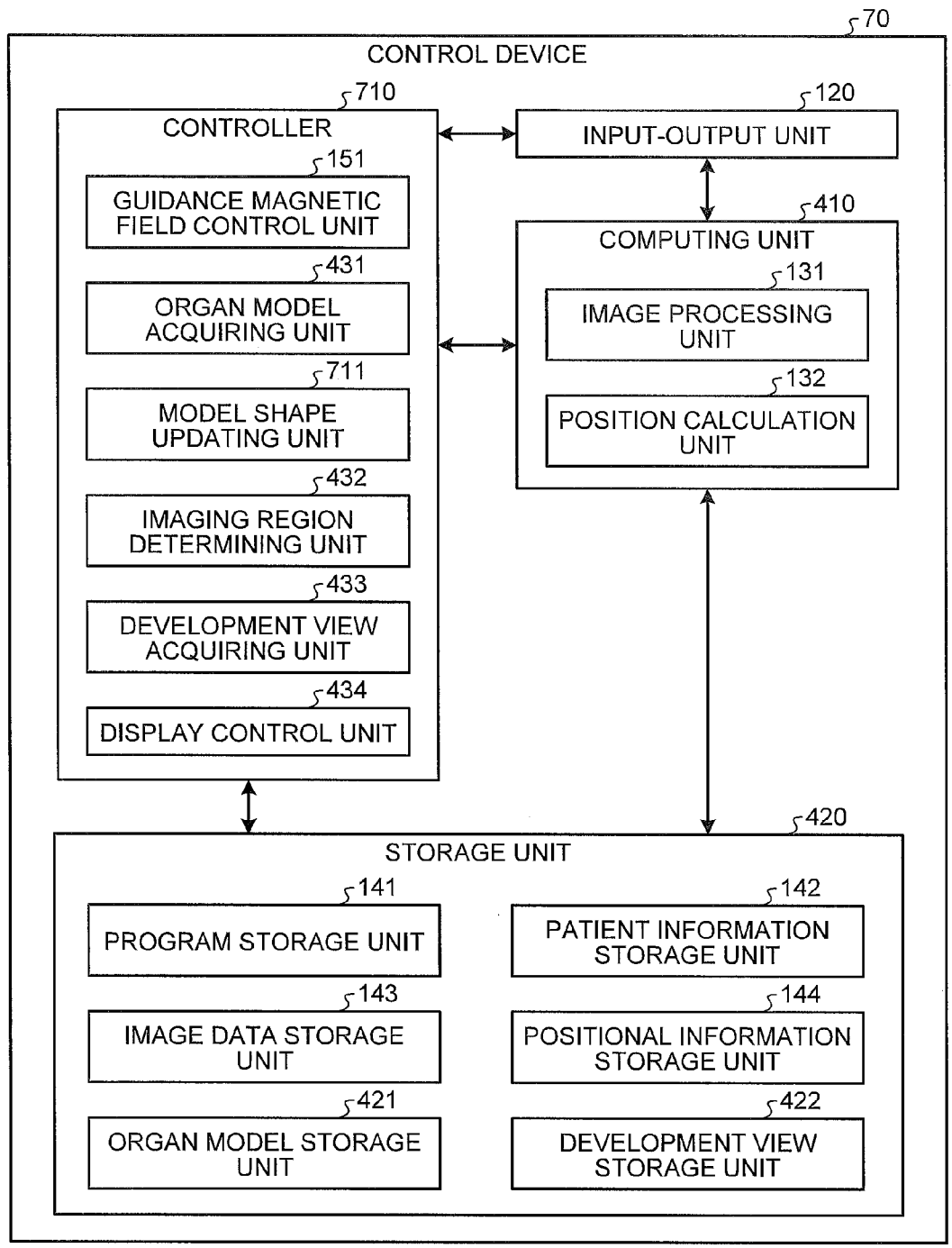
FIG. 42 is a block diagram illustrating a configuration example of a control device included in a capsule endoscope system according to a modification 6-2 of the sixth embodiment of the present invention.

FIG. 42 is a block diagram illustrating a configuration example of a control device included in a capsule endoscope system according to the modification 6-2. A control device 70 illustrated in FIG. 42 includes a controller 710 in place of the controller 430 in comparison with the control device 40 illustrated in FIG. 30. Configurations of respective units of the control device 70 other than the controller 710 are similar to those in the fifth embodiment. Further, configurations of respective units of the capsule endoscope system other than the control device 70 are also similar to those in the fifth embodiment (see FIGS. 1 and 31).

The controller 710 further includes a model shape updating unit 711, in comparison with the controller 430 illustrated in FIG. 30. The model shape updating unit 711 updates a shape parameter of an organ model based on a position and a posture of a capsule endoscope 10A calculated by a position calculation unit 132, and guidance instruction information input from an operation input device 16.

Figure 43:
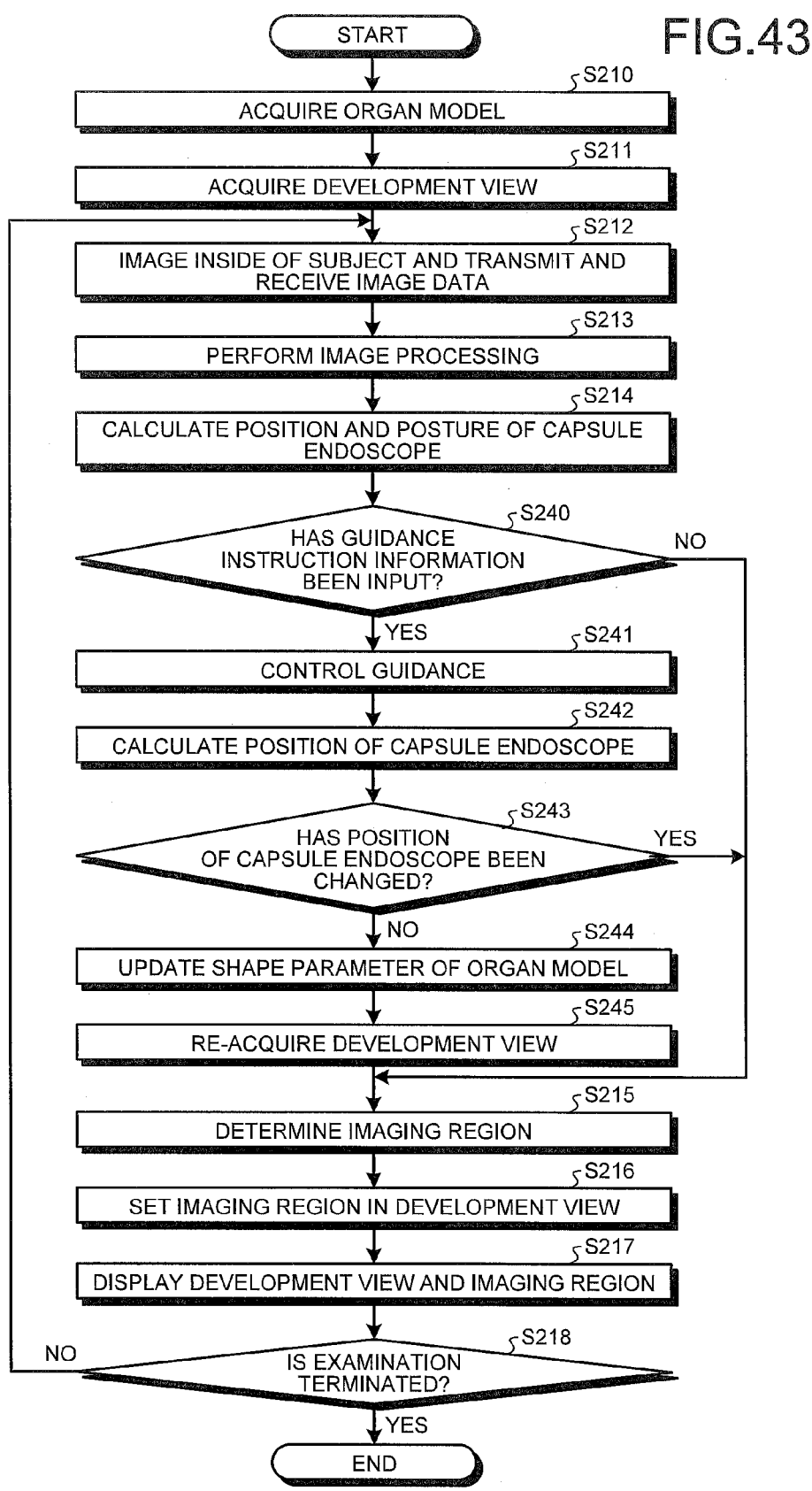
FIG. 43 is a flowchart illustrating a movement of the capsule endoscope system according to the modification 6-2 of the sixth embodiment of the present invention.

Next, an operation of the capsule endoscope system according to the modification 6-2 will be described with reference to FIG. 43. Note that steps S210 to S214 illustrated in FIG. 43 are similar to those in the fifth embodiment.

In step S240 following step S214, the model shape updating unit 711 determines whether guidance instruction information has been input from the operation input device 16 to the control device 70. When the guidance instruction information is not input (No in step S240), the operation of the capsule endoscope system proceeds to step S215.

Meanwhile, when the guidance instruction information has been input (Yes in step S240), a guidance magnetic field control unit 151 performs guidance control for the capsule endoscope 10A by outputting a control signal to a signal generating device 14 based on the guidance instruction information (step S241).

In following step S242, a position calculation unit 132 calculates a position of the capsule endoscope 10A again based on the position detection signal output from a signal processing device 13.

In step S243, the model shape updating unit 711 determines whether the position of the capsule endoscope 10A calculated in step S242 has been changed from the position of the capsule endoscope calculated in step S214. When the position of the capsule endoscope 10A has been changed (Yes in step S243), the operation of the capsule endoscope system is moved into step S215.

Figure 44A:
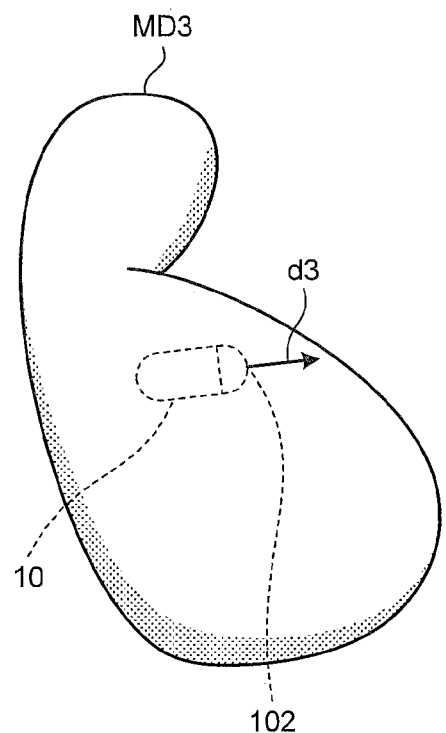
FIGS. 44A and 44B are schematic diagrams for describing a method of updating a shape parameter of an organ model in the modification 6-2 of the sixth embodiment of the present invention.
Figure 44B:
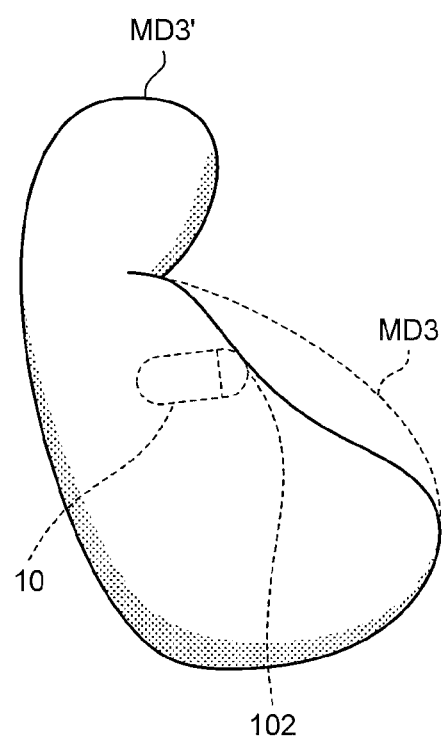

Meanwhile, when the position of the capsule endoscope is not changed (No in step S243), the model shape updating unit 711 updates the shape parameter of the organ model (step S244). For example, as illustrated in FIG. 44A, assume that a positional relationship between the capsule endoscope 10A and an organ model MD3 is determined based on the position and the posture of the capsule endoscope 10A calculated in step S214. It can be considered that the capsule endoscope 10A has already reached a wall of the organ in a subject 2 when the position of the capsule endoscope 10A is not changed even though the guidance magnetic field control unit 151 has performed control to move the capsule endoscope 10A by a distance d3 in the direction of the arrow in the drawing, according to the guidance instruction information. In such a case, the model shape updating unit 711 causes the position of the wall of the organ model MD3 to conform to an end portion of the capsule endoscope 10A, and updates the shape parameter such that surroundings of the position of the wall become continuous, as illustrated in FIG. 44B. Accordingly, an updated organ model MD3' is created.

In step S245, a development view acquiring unit 433 re-acquires a development view of the organ model based on the updated shape parameter. Accordingly, a development view corresponding to the updated organ model MD3' is created.

Following steps S215 to S218 are similar to those in the fifth embodiment.

As described above, according to the modification 6-2, the guidance instruction information and change of the position of the capsule endoscope 10A are changed, so that the shape of the organ model can be easily updated. Further, according to the modification 6-2, it is not necessary to perform an operation to calculate a distance between the capsule endoscope 10A and the organ and to provide a distance measuring unit in the capsule endoscope 10A. Therefore, configurations of the capsule endoscope 10A and the control device 70 can be simplified.

Further, according to the modification 6-2, even if the shape of the organ model stored in an organ model storage unit 421 in advance is different from the shape of the organ of the subject 2, the shape of the organ model is updated to gradually get closer to the shape of the organ of the subject 2 while continuing to perform a guiding operation of the capsule endoscope 10A. Therefore, an imaging region is determined in the organ model updated as described above, and the imaging region is displayed in a development view of the updated organ model, whereby a user can accurately grasp a current imaging region by the capsule endoscope 10A.

Seventh Embodiment

Next, a seventh embodiment of the present invention will be described.

Figure 45:
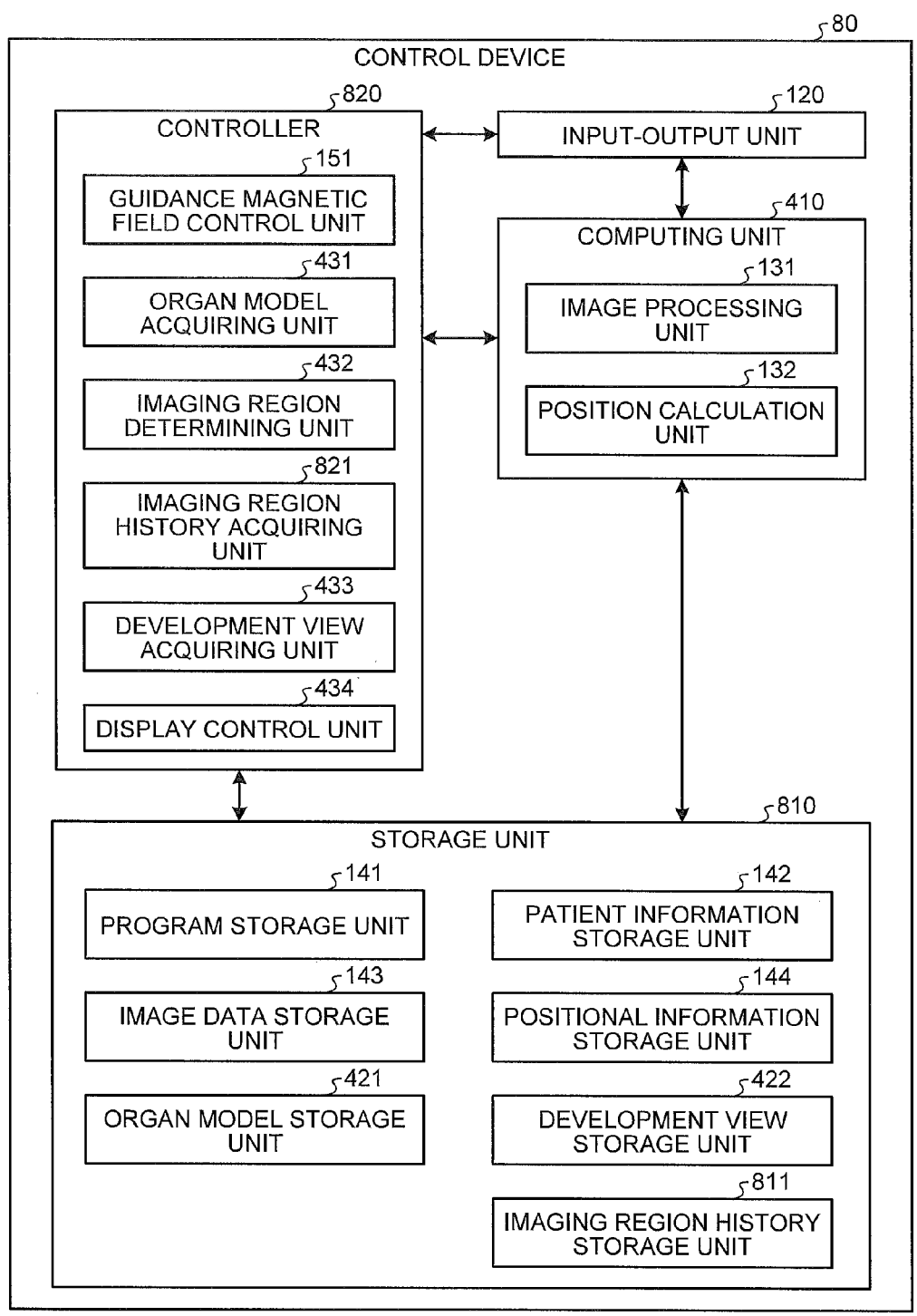
FIG. 45 is a block diagram illustrating a configuration example of a control device included in a capsule endoscope system according to a seventh embodiment of the present invention.

FIG. 45 is a block diagram illustrating a configuration example of a control device included in a capsule endoscope according to the seventh embodiment. A control device 80 illustrated in FIG. 45 includes a storage unit 810 and a controller 820, in place of the storage unit 420 and the controller 430 in comparison with the control device 40 illustrated in FIG. 30. Configurations of respective units of the control device 80 other than the storage unit 810 and the controller 820 are similar to those in the fifth embodiment.

Further, configurations of the capsule endoscope system other than the control device 80 are also similar to those in the fifth embodiment (see FIGS. 1 and 31).

The storage unit 810 further includes an imaging region history storage unit 811, in comparison with the storage unit 420 illustrated in FIG. 30. The imaging region history storage unit 811 sequentially stores a position and an imaging direction of an imaging unit 102 calculated when an imaging region determining unit 432 determines an imaging region as information related to an imaging region.

The controller 820 further includes an imaging region history acquiring unit 821, in comparison with the controller 430 illustrated in FIG. 30. The imaging region history acquiring unit 821 acquires an imaging region corresponding to an image (displayed image) already displayed on a display device 18 from the position and the imaging direction of the imaging unit 102 stored in the imaging region history storage unit 811 and three-dimensional data of an organ model.

Figure 46:
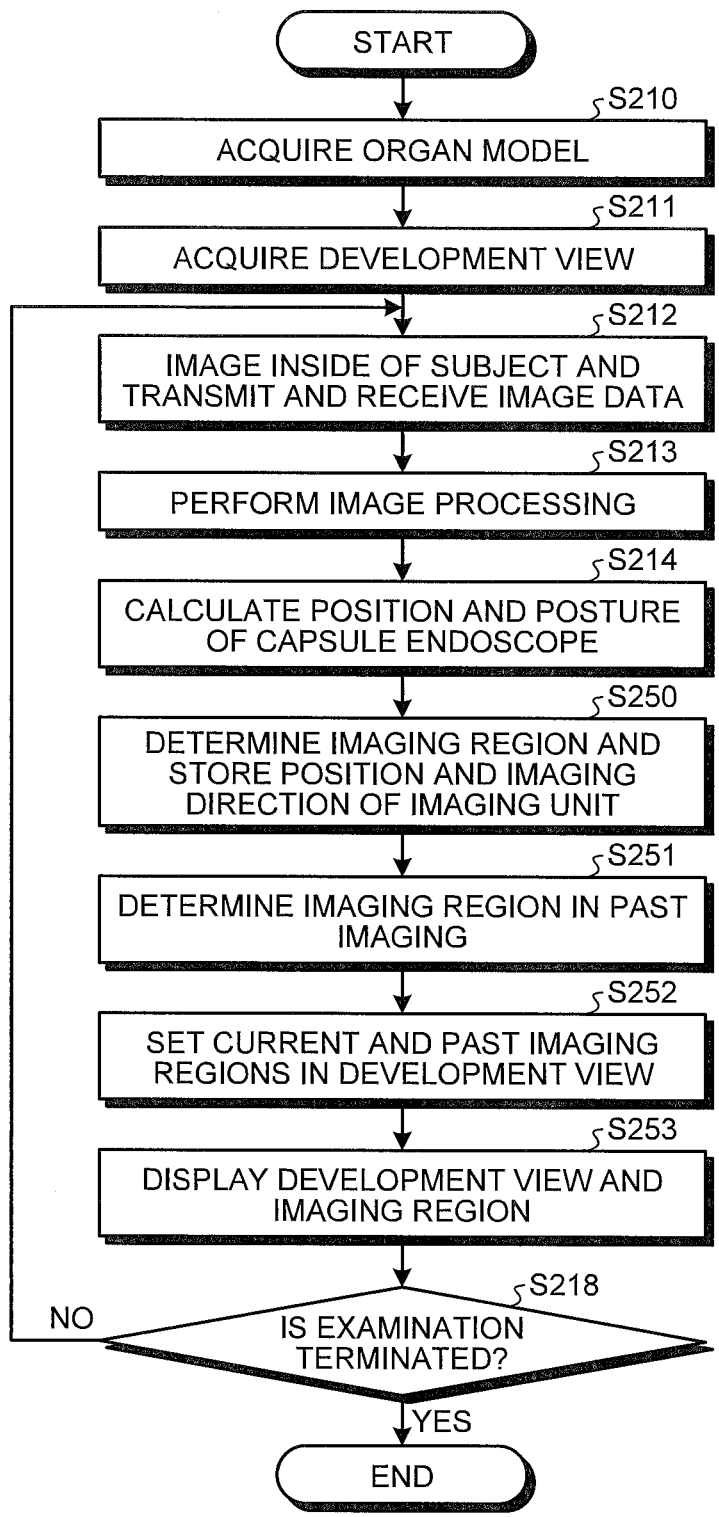
FIG. 46 is a flowchart illustrating a movement of the capsule endoscope system according to the seventh embodiment of the present invention.

Next, an operation of the capsule endoscope system according to the seventh embodiment will be described with reference to FIG. 46. Note that steps S210 and S214 illustrated in FIG. 46 are similar to those in the fifth embodiment.

In step S250 following step S214, the imaging region determining unit 432 determines a current imaging region by a capsule endoscope 10A. Note that the method of determining the imaging region is similar to step S215 (see FIG. 34). Further, the imaging region determining unit 432 stores the position and the imaging direction of the imaging unit 102 calculated in determining the imaging region in association with an in-vivo image of the imaging region in the imaging region history storage unit 811.

In step S251, the imaging region history acquiring unit 821 reads the position and the imaging direction of the imaging unit 102 at the time of past imaging stored in the imaging region history storage unit 811, and determines the imaging region at the time of past imaging based on a positional relationship between the imaging unit 102 and an organ model and the imaging direction of the imaging unit 102. The method of determining the imaging region is similar to step S215 (see FIG. 34).

Figure 47:
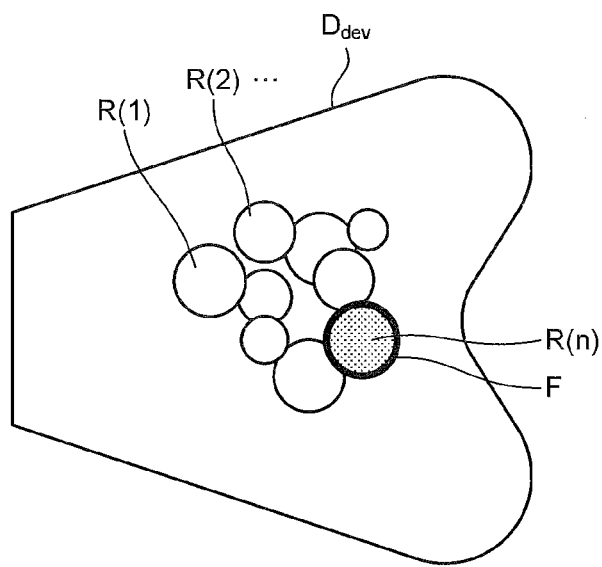
FIG. 47 is a schematic diagram illustrating an example of superimposing present and past imaging regions on a development view of an organ model.

In step S252, a development view acquiring unit 433 acquires a development view of the organ model, and sets current and past imaging regions in the development view. For example, the development view acquiring unit 433 sets a region on a development view $D_{dev}$ of the organ model corresponding to the imaging region determined in step S250 as an current imaging region R(n) (n is a natural number), and sets regions on the development view $D_{dev}$ corresponding to the imaging regions determined in step S251 as past imaging regions R(1) to R(n−1), as illustrated in FIG. 47.

In step S253, a display control unit 434 causes a display device 18 to display a screen including the development view of the organ model and the imaging regions. To be specific, the display device 18 displays the development view $D_{dev}$ (see FIG. 47) in an imaging region display region m20 (see FIG. 32) under control of the display control unit 434. Then, the display device 18 superimposes a latest in-vivo image generated in step S213 on the imaging region R(n) and displays the superimposed image, and superimposes past-acquired in-vivo images on the imaging regions R(1) to R(n−1), respectively and displays the superimposed images. At this time, a contour is enhanced by adding a predetermined picture frame F to the latest imaging region R(n) or the like so that the latest imaging region can be identified from the past imaging regions. Note that the past-acquired in-vivo images are read from an image data storage unit 143 based on information related to the imaging region stored in the imaging region history storage unit 811.

Alternatively, the in-vivo image may be superimposed only on the latest imaging region R(n), and as for the past imaging regions R(1) to R(n−1), the past imaging regions may be filled with a single color or a predetermined pattern is added to the past imaging regions so that the latest imaging region can be identified. Subsequent step S218 is similar to that in the fifth embodiment.

As described above, according to the seventh embodiment, the regions imaged by the capsule endoscope 10A so far are displayed in the development view of the organ model in real time. Therefore, a user can easily determine whether there is a region that has not yet been observed in the organ.

Modification 7-1

Next, a modification 7-1 of the seventh embodiment will be described.

In the seventh embodiment, a case in which the imaging region history storage unit 811 and the imaging region history acquiring unit 821 are applied to the control device 40 in the fifth embodiment has been described. However, the similar configuration may be provided to the control devices 50 to 70 described in the modification 5-2, the sixth embodiment, and the modification 6-2.

Figure 48:
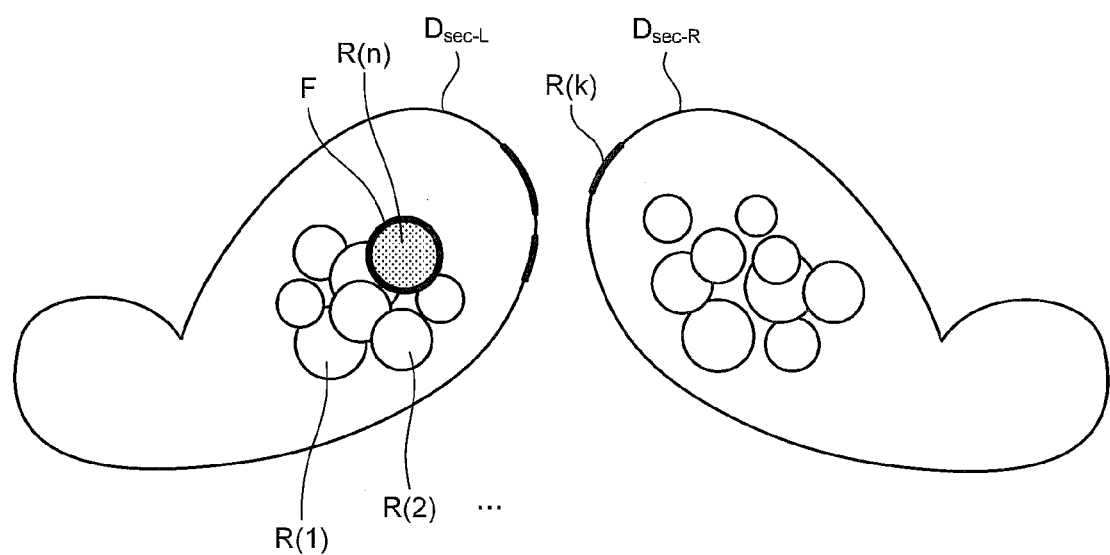
FIG. 48 is a schematic diagram illustrating an example of superimposing present and past imaging regions on a sectional view of an organ model.

When the imaging region history storage unit 811 and the imaging region history acquiring unit 821 are applied to the control device 50 in the modification 5-2, it is favorable to display both sectional views $D_{sec-R}$ and $D_{sec-L}$ of both ends that are equally-divided organ models, at the same time, as illustrated in FIG. 48. Note that the cut surface of the organ model may be one fixed plane, or a surface parallel to or perpendicular to a current imaging direction by an imaging unit 102 may be set as the cut surface and sequentially changed. Further, an imaging region positioned on the cut surface of the organ model (for example, an imaging region R(k)) may be displayed such that the imaging region is filled with a specific color or a pattern such as slant lines are added to the imaging region.

Further, when the imaging region history storage unit 811 and the imaging region history acquiring unit 821 are applied to the sixth embodiment or the modification 6-2, the imaging region history acquiring unit 821 determines the imaging region for an updated latest organ model. Accordingly, the past imaging region can be more accurately displayed.

Modification 7-2

Next, a modification 7-2 of the seventh embodiment will be described.

In the seventh embodiment, the development view (see FIG. 47) of the organ model is displayed such that the past imaging regions R(1) to R(n−1) are filled with a single color, or a predetermined pattern is added to the past imaging regions. However, the color and the pattern in displaying the past imaging regions R(1) to R(n−1) may be changed according to conditions.

For example, a display color of an imaging region may be changed according to the frequency of observation to the same imaging region. To be specific, the color of the imaging region on the development view $D_{dev}$ becomes thicker (or luminance becomes lower, or chroma becomes higher) as the frequency of observation in a region is higher, and the color of the imaging region on the development view $D_{dev}$ becomes thinner (or the luminance becomes higher, or the chroma becomes lower) as the frequency of observation in a region is lower. Alternatively, the display color of the imaging region may be changed according to an observation time for the same imaging region. To be specific, the color of the imaging region on the development view $D_{dev}$ becomes thicker as the observation time is longer in a region, and the color of the imaging region on the development view $D_{dev}$ becomes thinner as the frequency of observation is lower in a region. Further, the display color or the pattern of the imaging region on the development view $D_{dev}$ corresponding to the in-vivo image may be changed depending on an average color of the in-vivo image, a type of a characteristic point of a cardia appearing on the in-vivo image, or whether an operation to capture the in-vivo image has been performed.

As described above, according to the modification 7-2, the colors and the patterns with which the past imaging regions R(1) to R(n−1) are displayed are changed according to conditions, in the development view $D_{dev}$ of the organ model. Therefore, a user can easily grasp a region in the organ which has been displayed as the in-vivo image (observation has been done), and an observation state for the region.

Note that a display similar to the modification 7-2 may be performed for the sectional views $D_{sec-R}$ and $D_{sec-L}$ illustrated in FIG. 48.

Modification 7-3

Next, a modification 7-3 of the seventh embodiment will be described.

In displaying a development view $D_{dev}$ of an organ model such that colors or patterns are added to past imaging regions R(1) to R(n−1), the development view $D_{dev}$ may be divided into a plurality of sections, and colors or patterns that display imaging regions R(1) to R(n−1) may be changed for each divided section.

Figure 49:
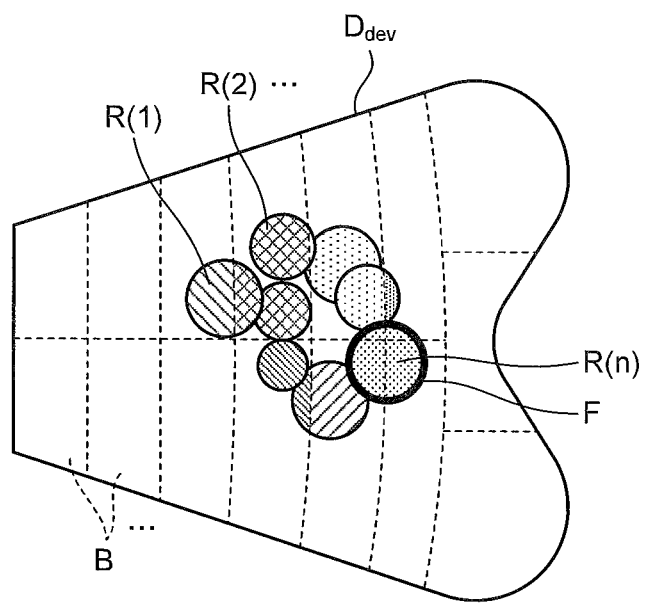
FIG. 49 is a schematic diagram illustrating a display example of a development view of an organ model in a modification 7-3 of the seventh embodiment of the present invention.

FIG. 49 is a schematic diagram illustrating a display example of a development view $D_{dev}$ of an organ model in the modification 7-3. In the modification 7-3, an example in which the development view $D_{dev}$ of the organ model is divided into fifteen sections B is illustrated. However, the number of division is not limited to fifteen. Note that, in FIG. 49, different patterns indicate different colors.

As described above, the past imaging regions R(1) to R(n−1) are displayed with different colors or patterns in each section B that is a divided development view $D_{dev}$ of the organ model, whereby a user can easily and intuitively grasp which portion (an upper portion, a lower portion, or the like) in the organ has been displayed as the in-vivo image (the observation has been done).

Note that a display similar to the modification 7-3 may be performed for the sectional views $D_{sec-R}$ and $D_{sec-L}$ illustrated in FIG. 48.

Modification 7-4

Next, a modification 7-4 of the seventh embodiment will be described.

In displaying an in-vivo image on past imaging regions R(1) to R(n−1) on a development view $D_{dev}$ of an organ model, colors or patterns may be added to surroundings of the imaging regions R(1) to R(n−1).

In this case, first, an imaging region history acquiring unit 821 divides a development view $D_{dev}$ of an organ model into a plurality of sections B (see FIG. 49), and calculates a sum of areas of the past imaging regions R(1) to R(n-1), for each of the divided sections B. Then, the imaging region history acquiring unit 821 calculates a ratio of the sum of the areas of the imaging regions R(1) to R(n-1) to an area of this section B, for each of the sections B.

A display control unit 434 displays regions other than the imaging regions R(1) to R(n-1) with a predetermined color or pattern, for the sections B with the ratio of the sum of the areas calculated by the imaging region history acquiring unit 821 being a predetermined value or more (for example, 80% or more). Alternatively, the color or the pattern in the regions other than the imaging regions R(1) to R(n-1) may be changed according to the ratio of the sum of the areas.

As described above, a display state of an in-vivo image (the ratio of the displayed regions) is discriminated for each section B that is a divided development view $D_{dev}$, and the background of the imaging regions R(1) to R(n-1) is displayed with the color or the pattern according to the display state. Therefore, a user can easily and intuitively grasp to what extent the region in an organ corresponding to each section B has been covered.

Note that a display similar to the modification 7-4 may be performed for the sectional views $D_{sec-R}$ and $D_{sec-L}$ illustrated in FIG. 48.

Modification 7-5

Next, a modification 7-5 of the seventh embodiment will be described.

In the seventh embodiment, the imaging region of the in-vivo image is determined based on the position and the posture of the capsule endoscope 10A and an imaging distance to the imaging target (stomach wall), and the in-vivo image and the specific color or pattern are added on the region on the development view $D_{dev}$ of the organ model corresponding to the imaging region, and the image is displayed. Therefore, the region on the development view $D_{dev}$ corresponding to the imaging region of each in-vivo image becomes larger as the imaging distance is shorter.

However, the size of the region on the development view $D_{dev}$ corresponding to the imaging region of the in-vivo image does not necessarily correspond to the imaging distance. For example, the size of the region on the development view $D_{dev}$ may be made constant without depending on the imaging distance, or the size of the region on the development view $D_{dev}$ may be made smaller as the imaging distance is shorter. Further, a central point of the region on the development view $D_{dev}$ corresponding to the imaging region of the in-vivo image is sequentially connected, so that a trajectory of the regions already displayed as the in-vivo images may be displayed. Further, a user may be able to select a desired display mode from these display modes.

In the above-described fifth to seventh embodiments, the development view $D_{dev}$ (see FIGS. 47 and 49) or the sectional views $D_{sec-R}$ and $D_{sec-L}$ (see FIG. 48) of the organ model is displayed on the imaging region display region m20. However, the organ model itself may be stereographically displayed. Further, the display mode (the development view, the sectional view, or a cubic diagram) on the imaging region display region m20 may be switched according to an operation to the operation input device 16.

In the above-described first to seventh embodiments and modifications thereof, the specific examples have been described using the stomach as an observation target. However, the embodiments and modifications can be applied to cases where other organs (digestive tract) such as an esophagus, a duodenum, a small intestine, a large intestine are observed.

According to some embodiments, the body posture of the subject is discriminated, and at least one of the body posture model according to the body posture of the subject and the organ model corresponding to the body posture model is displayed. Therefore, even if the body posture of the subject is changed during an examination, the user can easily grasp the position and the direction being imaged by the capsule endoscope.

Further, according to some embodiments, the imaging region is set on the development view or the sectional view of the model of the organ as the imaging target, and an image acquired by the capsule endoscope is superimposed on the imaging region and the superimposed image is displayed. Therefore, the user can accurately grasp the region being imaged by the capsule endoscope in real time.

The above-described first to seventh embodiments and modifications thereof are mere examples for implementing the present invention, and the present invention is not limited to these examples. Further, the present invention can form various inventions by appropriately combining the plurality of configuration elements disclosed in the first to seventh embodiments and the modifications. The present invention can be changed in various forms according to specifications and the like. Further, it is apparent that other various embodiments can be made within the scope of the present invention from the above description.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A capsule endoscope system comprising:
   a capsule endoscope configured to be introduced into an inside of a subject and to image the inside of the subject;
   a guiding unit configured to generate a magnetic field to guide the capsule endoscope;
   a guidance magnetic field control unit configured to switch between ON and OFF of the magnetic field generated by the guiding unit;
   a body posture discriminating unit configured to discriminate a body posture of the subject;
   a model extracting unit configured to extract a body posture model according to the body posture of the subject discriminated by the body posture discriminating unit, from among prepared body posture models, and to extract an organ model according to the body posture of the subject discriminated by the body posture discriminating unit, from among prepared organ models correlated with the body posture of the subject; and
   a display control unit configured to:
   distinguish between ON and OFF of the magnetic field generated by the guiding unit, based on switching by the guidance magnetic field control unit;
   superimpose the organ model according to the body posture of the subject extracted by the model extracting unit, on the body posture model extracted by the model extracting unit to produce a superimposed image, and to display the superimposed image when the magnetic field generated by the guiding unit is distinguished to be ON; and display the body posture model extracted by the model extracting unit and to hide the organ model when the magnetic field generated by the guiding unit is distinguished to be OFF.

2. The capsule endoscope system according to claim 1, further comprising an input unit configured to output a signal according to an operation by an operator, wherein
the body posture discriminating unit is configured to discriminate the body posture of the subject based on the signal output from the input unit.

3. The capsule endoscope system according to claim 1, wherein the display control unit is configured to display a dialogue to input the body posture of the subject when the guiding unit starts generation of the magnetic field.

4. The capsule endoscope system according to claim 1, further comprising an acceleration detecting unit configured to detect acceleration applied to the subject, wherein
the body posture discriminating unit is configured to discriminate the body posture of the subject based on a detection result of the acceleration.

5. The capsule endoscope system according to claim 1, wherein the display control unit is configured to enlarge the body posture model and the organ model when the magnetic field generated by the guiding unit is distinguished to be ON.

6. The capsule endoscope system according to claim 1, further comprising a detecting unit configured to detect a position and a posture of the capsule endoscope, wherein
when the magnetic field generated by the guiding unit is distinguished to be ON, the display control unit is configured to superimpose a prepared schematic image of the capsule endoscope on at least one of the body posture model and the organ model, based on the position and the posture of the capsule endoscope detected by the detecting unit to produce a superimposed image, and to display the superimposed image.

7. The capsule endoscope system according to claim 6, wherein when the magnetic field generated by the guiding unit is distinguished to be ON, the display control unit is configured to:
superimpose the schematic image on the body posture model and to display the superimposed image when the capsule endoscope is located outside a guidance region that is a region where guidance by the guiding unit is available; and
superimpose the schematic image on the body posture model and the organ model and to enlarge the superimposed image when the capsule endoscope is located inside the guidance region.

8. The capsule endoscope system according to claim 6, wherein the display control unit is configured to change a relative size of the schematic image with respect to at least one of the body posture model and the organ model according to a position of the capsule endoscope in a vertical direction in the subject.

9. The capsule endoscope system according to claim 6, further comprising a distance acquiring unit configured to acquire a distance between the capsule endoscope and a wall surface of an organ in the subject, wherein
the display control unit is configured to adjust a relative display position between the organ model and the schematic image according to the distance.

10. The capsule endoscope system according to claim 6, further comprising an input unit configured to output a signal according to an operation by an operator to the guiding unit, wherein
the guiding unit is configured to generate the magnetic field based on the operation to the input unit, and
the display control unit is configured to adjust a relative display position between the organ model and the schematic image based on an operation amount to the input unit and on a change amount of the position of the capsule endoscope detected by the detecting unit.

11. The capsule endoscope system according to claim 1, wherein the display control unit is configured to display an organ model according to characteristics of the subject, among the prepared organ models for one body posture.

* * * * *